United States Patent
Lane et al.

(10) Patent No.: US 11,718,580 B2
(45) Date of Patent: Aug. 8, 2023

(54) FLUORENE DERIVATIZED MONOMERS AND POLYMERS FOR VOLUME BRAGG GRATINGS

(71) Applicant: META PLATFORMS TECHNOLOGIES, LLC, Menlo Park, CA (US)

(72) Inventors: Austin Lane, Sammamish, WA (US); Matthew E. Colburn, Woodinville, WA (US); Lafe Purvis, Redmond, WA (US)

(73) Assignee: META PLATFORMS TECHNOLOGIES, LLC, Menlo Park, CA (US)

(*) Notice: Subject to any disclaimer, the term of this patent is extended or adjusted under 35 U.S.C. 154(b) by 0 days.

(21) Appl. No.: 16/865,073

(22) Filed: May 1, 2020

(65) Prior Publication Data

US 2020/0354311 A1 Nov. 12, 2020

Related U.S. Application Data

(60) Provisional application No. 62/845,258, filed on May 8, 2019.

(51) Int. Cl.
*G03H 1/02* (2006.01)
*C07C 69/54* (2006.01)
(Continued)

(52) U.S. Cl.
CPC ............ *C07C 271/48* (2013.01); *C07C 69/54* (2013.01); *C07C 323/62* (2013.01); *G03F 7/025* (2013.01);
(Continued)

(58) Field of Classification Search
CPC ...... C07C 271/48; C07C 69/54; C07C 323/62
See application file for complete search history.

(56) References Cited

U.S. PATENT DOCUMENTS 4,068,849 A 1/1978 DiSalvo et al.
4,180,673 A 12/1979 Burguette
(Continued)

FOREIGN PATENT DOCUMENTS

CN 1795166 A 6/2006
CN 1867566 A 11/2006
(Continued)

OTHER PUBLICATIONS

Machine translation of JP 2009079013 (2009).*
(Continued)

*Primary Examiner* — Martin J Angebranndt
(74) *Attorney, Agent, or Firm* — Morgan, Lewis & Bockius LLP

(57) ABSTRACT

The disclosure provides recording materials include fluorene derivatized monomers and polymers for use in volume Bragg gratings, including, but not limited to, volume Bragg gratings for holography applications. Several fluorene structures are disclosed: simply substituted fluorenes, cardo-fluorenes, and spiro-fluorenes. Fluorene derivatized polymers in Bragg gratings applications lead to materials with higher refractive index, low birefringence, and high transparency. Fluorene derivatized monomers/polymers can be used in any volume Bragg gratings materials, including two-stage polymer materials where a matrix is cured in a first step, and then the volume Bragg grating is written by way of a second curing step of a monomer.

7 Claims, 9 Drawing Sheets

(51) Int. Cl.
  *C07C 271/48* (2006.01)
  *C07C 323/62* (2006.01)
  *G03F 7/035* (2006.01)
  *G03F 7/027* (2006.01)
  *G03F 7/025* (2006.01)

(52) U.S. Cl.
  CPC ........... *G03F 7/027* (2013.01); *G03H 1/0248* (2013.01); *G03H 2001/0264* (2013.01); *G03H 2260/12* (2013.01)

(56) References Cited

U.S. PATENT DOCUMENTS

| | | | |
|---|---|---|---|
| 4,970,129 | A | 11/1990 | Ingwall et al. |
| 5,219,710 | A | 6/1993 | Horn et al. |
| 5,292,620 | A | 3/1994 | Booth et al. |
| 5,759,721 | A | 6/1998 | Dhal et al. |
| 5,858,614 | A * | 1/1999 | Sato .................... G03H 1/0248 430/1 |
| 5,874,187 | A | 2/1999 | Colvin et al. |
| 5,932,045 | A | 8/1999 | Campbell et al. |
| 6,103,454 | A | 8/2000 | Dhar et al. |
| 6,482,551 | B1 | 11/2002 | Dhar et al. |
| 6,650,447 | B2 | 11/2003 | Curtis et al. |
| 6,743,552 | B2 | 6/2004 | Setthachayanon et al. |
| 6,765,061 | B2 | 7/2004 | Dhar et al. |
| 6,780,546 | B2 | 8/2004 | Trentler et al. |
| 7,704,643 | B2 | 4/2010 | Cole et al. |
| 8,071,260 | B1 | 12/2011 | Cole et al. |
| 8,183,303 | B2 | 5/2012 | Jeong et al. |
| 8,202,468 | B2 | 6/2012 | Zhu et al. |
| 8,206,639 | B2 | 6/2012 | Zhu et al. |
| 8,282,381 | B1 | 10/2012 | Zhu et al. |
| 8,344,065 | B2 | 1/2013 | Zhu et al. |
| 8,574,822 | B2 | 11/2013 | Zhu et al. |
| 8,822,125 | B2 | 9/2014 | Kim |
| 2002/0142227 | A1 | 10/2002 | Dhar et al. |
| 2003/0053774 | A1 | 3/2003 | Blomquist et al. |
| 2003/0096172 | A1 | 5/2003 | Ichihashi et al. |
| 2003/0139486 | A1 | 7/2003 | Yamada et al. |
| 2003/0206320 | A1 | 11/2003 | Cole et al. |
| 2004/0027625 | A1 | 2/2004 | Trentler et al. |
| 2004/0038035 | A1 | 2/2004 | Johnson et al. |
| 2004/0197670 | A1* | 10/2004 | Takeyama ................ G03H 1/02 430/1 |
| 2005/0058911 | A1* | 3/2005 | Takeyama ............... G03F 7/029 430/1 |
| 2005/0064333 | A1 | 3/2005 | Crivello |
| 2006/0069222 | A1 | 3/2006 | Chisholm et al. |
| 2006/0223921 | A1 | 10/2006 | Bauer et al. |
| 2007/0078198 | A1* | 4/2007 | Otsuji .................... C07C 323/20 523/120 |
| 2008/0312403 | A1 | 12/2008 | Stockel et al. |
| 2009/0023879 | A1 | 1/2009 | Wanders et al. |
| 2009/0185470 | A1 | 7/2009 | Stoeckel et al. |
| 2009/0195847 | A1 | 8/2009 | Mikoshiba et al. |
| 2009/0247660 | A1 | 10/2009 | Park et al. |
| 2009/0295041 | A1 | 12/2009 | Petrucci-Samija et al. |
| 2009/0310196 | A1 | 12/2009 | Shimizu et al. |
| 2010/0086860 | A1 | 4/2010 | Roelle et al. |
| 2010/0086861 | A1 | 4/2010 | Weiser et al. |
| 2010/0087564 | A1 | 4/2010 | Weiser et al. |
| 2010/0112459 | A1 | 5/2010 | Weiser et al. |
| 2010/0197821 | A1 | 8/2010 | Jeong et al. |
| 2010/0197824 | A1 | 8/2010 | Bissinger et al. |
| 2010/0197876 | A1 | 8/2010 | Lyu et al. |
| 2010/0203241 | A1* | 8/2010 | Weiser .................... C08G 18/48 522/7 |
| 2010/0221646 | A1 | 9/2010 | Kawamonzen et al. |
| 2011/0065827 | A1 | 3/2011 | Fäcke et al. |
| 2011/0092612 | A1* | 4/2011 | Miki ....................... G11B 7/244 522/154 |
| 2011/0207029 | A1 | 8/2011 | Hagen et al. |
| 2011/0311906 | A1 | 12/2011 | Rölle et al. |
| 2012/0010315 | A1 | 1/2012 | Rhee et al. |
| 2012/0161088 | A1 | 6/2012 | Choi et al. |
| 2012/0219884 | A1 | 8/2012 | Weiser et al. |
| 2012/0219885 | A1 | 8/2012 | Facke et al. |
| 2013/0038939 | A1 | 2/2013 | Walker, Jr. et al. |
| 2013/0241092 | A1 | 9/2013 | Takeuchi et al. |
| 2013/0252140 | A1* | 9/2013 | Facke .................... G03C 1/733 430/2 |
| 2013/0270535 | A1 | 10/2013 | Pillow et al. |
| 2014/0072720 | A1 | 3/2014 | Watkins et al. |
| 2014/0170345 | A1 | 6/2014 | Aoshima et al. |
| 2014/0349218 | A1 | 11/2014 | Shimizu et al. |
| 2015/0050479 | A1 | 2/2015 | Nakamura et al. |
| 2015/0050480 | A1 | 2/2015 | Suzuki et al. |
| 2015/0057422 | A1* | 2/2015 | Kondo ............. C08F 222/1006 526/280 |
| 2015/0118601 | A1* | 4/2015 | Rolle ................... G03H 1/0244 430/2 |
| 2015/0212487 | A1* | 7/2015 | Azakami ................ B32B 27/08 359/3 |
| 2016/0046551 | A1* | 2/2016 | Shiota .................... C07C 57/50 558/46 |
| 2016/0046552 | A1* | 2/2016 | Shiota .................... C08F 16/12 430/288.1 |
| 2016/0109618 | A1 | 4/2016 | Hunt et al. |
| 2016/0252808 | A1 | 9/2016 | Berneth et al. |
| 2017/0045816 | A1 | 2/2017 | Facke et al. |
| 2017/0303957 | A1 | 10/2017 | Vidal et al. |
| 2017/0362165 | A1 | 12/2017 | Facke et al. |
| 2017/0363957 | A1 | 12/2017 | Roelle et al. |
| 2017/0369783 | A1 | 12/2017 | Horiguchi et al. |
| 2018/0079925 | A1 | 3/2018 | Lyon et al. |
| 2018/0208531 | A1 | 7/2018 | Yen et al. |
| 2018/0217311 | A1 | 8/2018 | Hiraoka et al. |
| 2018/0217312 | A1 | 8/2018 | Hiraoka et al. |
| 2018/0223107 | A1 | 8/2018 | Monickam et al. |
| 2020/0247073 | A1 | 8/2020 | Rao et al. |
| 2020/0249568 | A1 | 8/2020 | Rao et al. |
| 2020/0355997 | A1 | 11/2020 | Lane et al. |
| 2021/0155581 | A1 | 5/2021 | Purvis et al. |
| 2021/0155584 | A1 | 5/2021 | Purvis et al. |
| 2021/0155585 | A1 | 5/2021 | Purvis et al. |
| 2021/0155599 | A1 | 5/2021 | Purvis et al. |
| 2022/0153693 | A1 | 5/2022 | Purvis, II et al. |
| 2022/0153895 | A1 | 5/2022 | Purvis, II et al. |

FOREIGN PATENT DOCUMENTS

| | | | |
|---|---|---|---|
| CN | 102850622 | A | 1/2013 |
| CN | 102854746 | A | 1/2013 |
| CN | 103153948 | A | 6/2013 |
| CN | 103254083 | A | 8/2013 |
| CN | 103755742 | A | 4/2014 |
| CN | 104003907 | * | 8/2014 |
| CN | 104395960 | A | 3/2015 |
| CN | 105418674 | A | 3/2016 |
| DE | 2365631 | A1 | 10/1975 |
| EP | 0320954 | A2 | 6/1989 |
| EP | 0415729 | A2 | 3/1991 |
| EP | 0775591 | A2 | 5/1997 |
| EP | 1512704 | A1 | 3/2005 |
| EP | 1627867 | A1 | 2/2006 |
| EP | 1708180 | A2 | 10/2006 |
| EP | 1792923 | A1 | 6/2007 |
| EP | 1873174 | A1 | 1/2008 |
| EP | 2065890 | A2 | 6/2009 |
| EP | 2172504 | A1 | 4/2010 |
| EP | 2221664 | A1 | 8/2010 |
| EP | 2228846 | A1 | 9/2010 |
| EP | 2330173 | A2 | 6/2011 |
| EP | 2354845 | A1 | 8/2011 |
| EP | 2735903 | A1 | 5/2014 |
| EP | 1984318 | B1 | 8/2015 |
| EP | 3107522 | B1 | 10/2018 |
| EP | 3747861 | A1 | 12/2020 |
| IT | AN20070022 | A1 | 10/2008 |
| JP | H02150410 | A | 6/1990 |
| JP | H06123858 | A | 5/1994 |

(56) References Cited

FOREIGN PATENT DOCUMENTS

| | | | |
|---|---|---|---|
| JP | H06301322 A | | 10/1994 |
| JP | H07145138 A | | 6/1995 |
| JP | 08-016077 | * | 1/1996 |
| JP | H10259219 A | | 9/1998 |
| JP | H1114801 A | | 1/1999 |
| JP | 2000-344716 | * | 12/2000 |
| JP | 2000356702 A | | 12/2000 |
| JP | 2001125474 A | | 5/2001 |
| JP | 2001-288177 | * | 10/2001 |
| JP | 2003029400 A | | 1/2003 |
| JP | 2003029604 A | | 1/2003 |
| JP | 2003167124 A | | 6/2003 |
| JP | 2005129139 A | | 5/2005 |
| JP | 2005263988 A | | 9/2005 |
| JP | 2006-208772 | * | 8/2006 |
| JP | 2007-084815 | * | 4/2007 |
| JP | 2008179777 A | | 8/2008 |
| JP | 2008-266632 | * | 11/2008 |
| JP | 2008285468 A | | 11/2008 |
| JP | 2009047871 A | | 3/2009 |
| JP | 2009-079013 | * | 4/2009 |
| JP | 2009091459 A | | 4/2009 |
| JP | 2009256275 A | | 11/2009 |
| JP | 2010077274 A | | 4/2010 |
| JP | 2010096942 A | | 4/2010 |
| JP | 2010150462 A | | 7/2010 |
| JP | 2010208911 A | | 9/2010 |
| JP | 2011168526 A | | 9/2011 |
| JP | 2011170073 A | | 9/2011 |
| JP | 2011-225469 | * | 11/2011 |
| JP | 2012-082387 | * | 4/2012 |
| JP | 2012224569 A | | 11/2012 |
| JP | 2013014533 A | | 1/2013 |
| JP | 2013043383 A | | 3/2013 |
| JP | 5257805 B | * | 5/2013 |
| JP | 2013122643 A | | 6/2013 |
| JP | 2014-001215 | * | 1/2014 |
| JP | 2014-063104 | * | 4/2014 |
| JP | 2014-132000 | * | 7/2014 |
| JP | 2015-117358 | * | 8/2015 |
| JP | 2016109983 A | | 6/2016 |
| JP | 2016-160420 | * | 9/2016 |
| JP | 2017062343 A | | 3/2017 |
| JP | 2018188372 A | | 11/2018 |
| KR | 100727871 B1 | | 6/2007 |
| KR | 20090097120 A | | 9/2009 |
| KR | 20110100974 A | | 9/2011 |
| KR | 20140117220 A | | 10/2014 |
| TW | 201311639 A | | 3/2013 |
| TW | I480695 B | | 4/2015 |
| TW | I494327 B | | 8/2015 |
| WO | 03101955 A2 | | 12/2003 |
| WO | 2005016919 A1 | | 2/2005 |
| WO | WO-2005101466 A2 | | 10/2005 |
| WO | 2005114331 A1 | | 12/2005 |
| WO | 2008125199 A1 | | 10/2008 |
| WO | 2008125229 A1 | | 10/2008 |
| WO | 2010027676 A2 | | 3/2010 |
| WO | 2011054792 A1 | | 5/2011 |
| WO | WO-2012070833 A2 | | 5/2012 |
| WO | WO-2013011893 A1 | | 1/2013 |
| WO | 2015161969 A1 | | 10/2015 |
| WO | 2018041132 A1 | | 3/2018 |
| WO | 2018071920 A1 | | 4/2018 |
| WO | 2019151463 A1 | | 8/2019 |
| WO | 2019237117 A1 | | 12/2019 |
| WO | 2021108191 A1 | | 6/2021 |
| WO | 2021108232 A1 | | 6/2021 |

OTHER PUBLICATIONS

Machine translation of JP 2012082387 (2012).*
Machine translation of JP 2014001215 (2014).*
Machine translatino of CN 104003907 (.*
Machine transation of JP 2016-160420 (2016).*
Machine translation of JP 5257805B (Aug. 2013).*
Machine translation of JP 2000-344716 (Dec. 2000).*
Alim M.D., et al., "High Dynamic Range (Δn) Two-Stage Photopolymers via Enhanced Solubility of a High Refractive Index Acrylate Writing Monomer," Applied Materials and Interfaces, 2018, vol. 10 (1), pp. 1217-1224.
"AMONIL & AMOPRIME—Low Viscosity Imprint Resist and Adhesion Promoter," AMO GmBH [online], May 15, 2020, 2 Pages, XP055696154, Retrieved from the Internet: URL: https://www.amo.de/wp-content/uploads/2017/04/FactSheetAMONIL.pdf.
Bier F., et al., "DOPO-Based Phosphorus-Containing Methacrylic (Co) Polymers: Glass Transition Temperature Investigation," Macro Molecular Materials and Engineering, Jan. 11, 2019, vol. 304, pp. 1-11.
Chodkiewicz W., et al., "Stereochemistry of Meso-Dihydroanthracene Quinols," Chemical Abstracts Service, Jan. 1, 1962, pp. 954-956.
Christian P., "Some Ethers and Esters from Meso-Dichlorodiphenylanthracene.Stereoisomerism of the Meso Ethers," Chemical Abstracts Service, Jan. 1, 1948, pp. 503-505.
Clark K.J., "84. The Preparation of 9 : 10-Di-(4-Carboxybutyl)Anthracene and Related Reactions," Journal Of The Chemical Society, Jan. 1, 1957, pp. 463-466.
Co-pending U.S. Appl. No. 17/515,194, inventors Austin; Lane et al., filed Oct. 29, 2021.
Co-pending U.S. Appl. No. 17/515,208, inventors Austin; Lane et al., filed Oct. 29, 2021.
Co-pending U.S. Appl. No. 16/779,446, filed Jan. 31, 2020, 141 Pages.
Devlin N.R., et al., "Patterning Decomposable Polynorbornene with Electron Beam Lithography to Create Nanochannels," Journal of Vacuum Science and Technology, vol. 27, No. 6, Dec. 1, 2009, pp. 2508-2511.
Dong J., et al., "Self-Assembly of Highly Stable Zirconium(IV) Coordination Cages with Aggregation Induced Emission Molecular Rotors for Live-Cell Imaging," Angewandte Chemie International Edition, vol. 59, No. 25, Jun. 15, 2020, 10 pages.
Final Office Action dated Jul. 28, 2022 for U.S. Appl. No. 17/098,130, filed Nov. 13, 2020, 14 pages.
Final Office Action dated Nov. 29, 2021 for U.S. Appl. No. 16/865,066, filed May 1, 2020, 13 pages.
Gadwal I., et al., "A New Approach for the Synthesis of Miktoarm Star Polymers Through a Combination of Thioi-Epoxy "Click" Chemistry and ATRP/Ring-Opening Polymerization Techniques," Journal of Polymer Science Part A: Polymer Chemistry, Oct. 31, 2018, vol. 57, No. 2, 11 pages.
Gadwal I., et al., "Multiply Functionalized Dendrimers: Protectivegroup-Free Synthesis Through Sequential Thiol-Epoxy 'click' Chemistry and Esterification Reaction," RSC Advances, May 4, 2015, vol. 5, No. 55, 5 pages.
Goldenberg L.M., et al., "Very Efficient Surface Relief Holographic Materials Based on Azobenzene-Containing Epoxy Resins Cured in Films," Journal Of Materials Chemistry, Jan. 1, 2010, vol. 20, No. 41, pp. 9161-9171.
Greene T.W., et al., "Protective Groups in Organic Synthesis," Third Edition, 1999, 799 pages.
Inan T.Y., et al "Preparation and Characterization of Novel UV-Curable Urethane Methacrylate Difunctional Monomers and their Structure-Property Relationships, 1," Macromolecular Chemistry and Physics, 2001, vol. 202, No. 4, pp. 532-540.
International Preliminary Report on Patentability for International Application No. PCT/US2020/016584, dated Aug. 19, 2021, 9 Pages.
International Preliminary Report on Patentability for International Application No. PCT/US2020/061120, dated Jun. 9, 2022, 9 pages.
International Preliminary Report on Patentability for International Application No. PCT/US2020/061218, dated Jun. 9, 2022, 9 pages.
International Preliminary Report on Patentability for International Application No. PCT/US2020/061396, dated Jun. 9, 2022, 13 pages.
International Preliminary Report on Patentability for International Application No. PCT/US2020/061714, dated Jun. 9, 2022, 11 pages.

(56) References Cited

OTHER PUBLICATIONS

International Preliminary Report on Patentability for International Application No. PCT/US2020/062284, dated Jun. 9, 2022, 7 pages.
International Search Report and Written Opinion for International Application No. PCT/US2020/016584, dated May 27, 2020, 11 Pages.
International Search Report and Written Opinion for International Application No. PCT/US2020/031445, dated Jun. 29, 2020, 10 Pages.
International Search Report and Written Opinion for International Application No. PCT/US2020/061120, dated Feb. 19, 2021, 12 pages.
International Search Report and Written Opinion for International Application No. PCT/US2020/061218, dated Feb. 16, 2021, 11 pages.
International Search Report and Written Opinion for International Application No. PCT/US2020/061714 dated Feb. 19, 2021, 17 pages.
International Search Report and Written Opinion for International Application No. PCT/US2021/059208, dated Apr. 19, 2022, 15 pages.
International Search Report and Written Opinion for International Application No. PCT/US2021/059241, dated Apr. 19, 2022, 15 pages.
International Search Report and Written Opinion for International Application PCT/US2022/022929, dated Aug. 30, 2022, 8 pages.
Kothari R., et al., "Direct Imprint Patterning of 2-D and 3-D Nanoparticle/Polymer Hybrid and Crystalline Metal Oxide Structures for Printed Optical, Electronic, and Energy Devices," 2016 6th Electronic System-Integration Technology Conference (ESTC), 2016, pp. 1-2.
Liu H.Y., et al., "A Comparative Study of Amorphous, Anatase, Rutile, and Mixed Phase TiO2 Films by Mist Chemical Vapor Deposition and Ultraviolet Photodetectors Applications," IEEE Sensors Journal, May 15, 2018, vol. 18, No. 10, pp. 4022-4029.
Liu Y., et al., "Influence of Chemical Structure of Monomers on Thermo-Stability of Holographic Polymer Dispersed Liquid Crystal Gratings," Acta Polymerica Sinica, Apr. 21, 2010, vol. 10, No. 4, pp. 408-415.
Non-Final Office Action dated Feb. 16, 2022 for U.S. Appl. No. 17/098,130, filed Nov. 13, 2020, 16 pages.
Non-Final Office Action dated May 12, 2022 for U.S. Appl. No. 16/865,066, filed May 1, 2020, 14 pages.
Non-Final Office Action dated Aug. 17, 2022 for U.S. Appl. No. 16/779,446, filed Jan. 31, 2020, 9 pages.
Non-Final Office Action dated May 19, 2021 for U.S. Appl. No. 16/865,066, filed May 1, 2020, 13 Pages.
Non-Final Office Action dated Jun. 22, 2022 for U.S. Appl. No. 17/098,146, filed Nov. 13, 2020, 13 pages.
Non-Final Office Action dated Oct. 3, 2022 for U.S. Appl. No. 17/386,280, filed Jul. 27, 2021, 11 pages.
Notice of Allowance dated Oct. 4, 2022 for U.S. Appl. No. 16/865,066, filed May 1, 2020, 10 pages.
Pradana A., et al., "Tailoring the Refractive Index of Nanoimprint Resist by Blending With TiO2 Nanoparticles," Optical Materials Express, Jan. 24, 2014, vol. 4, No. 2, 9 pages.
Saccone M., et al., "Halogen-Bonded Photoresponsive Materials," Top Curr. Chem., vol. 359, Jan. 1, 2015, pp. 147-166.
Sigma-Aldrich: "Pentaerythritol Triacrylate," May 15, 2020, 4 Pages, XP055696130, Retrieved from the Internet: URL https://www.sigmaaldrich.com/IN/en/product/aldrich/246794.
Sigma-Aldrich: "Poly (Ethylene Glycol) Methacrylate," May 15, 2020, 3 Pages, XP055696050, Retrieved from the Internet: URL: https://www.sigmaaldrich.com/IN/en/substance/polyethyleneglycolmethacrylate1234525736861?context=product.
Vita F., et al., "Effects of Resin Addition on Holographic Polymer Dispersed Liquid Crystals," Journal of Optics. A: Pure and Applied Optics, Institute of Physics Publishing, 2009, vol. 11, No. 2, 5 pages.
Yan L., et al., "Copolytnerization of (10-oxo-10-hydro-9-oxa-10Lamda5-Phosphaphenanthrene-10-yl)-Methyl Acrylate with Styrene," Chinese Chemical Letters, 2009, vol. 20, pp. 881-884.
Yoon H., et al., "Effect of Acrylate Monomers on the Diffraction Behavior of Photopolymers Fabricated with Cellulose Ester Polymer Binder," Optical Materials, Nov. 6, 2004, vol. 27, No. 6, pp. 1190-1196.
You N-H., et al., "Highly Refractive Polymer Resin Derived from Sulfur-Containing Aromatic Acrylate," Journal of Polymer Science, Part A: Polymer Chemistry, vol. 48 (12), Jun. 15, 2010, XP055704696, pp. 2604-2609.
Brinke et al., "The thermal characterization of multi-component systems by enthalpy relaxation," Thermochimica Acta., 238, (1994), 75-98, 24 pgs.
Colburn and Haines, "Volume Hologram Formation in Photopolymer Materials," Appl. Opt. 10, 1636-1641, 1971, 6 pgs.
Cruz et al., The Basis for Miscibility in Polyester-Polycarbonate Blends, (Macromolecules), American Chemical Society, vol. 12, No. 4, Jul.-Aug. 1979, 726, 1979, 6 pgs.
Facebook Technologies, LLC, International Search Report and Written Opinion, PCT/US20/31433, dated Jul. 20, 2020, 12 pgs.
Kelts et al., Two-Dimensional NMR of Synthetic Polymers: Polymer Blend Miscibility at the Molecular Level, Macromolecules, vol. 26, 2941-2949, 1993, 9 pgs.
Kim Joosung et al., "Synthesis of Fluorene-containing Photosensitive Polymer and Its Application to the Carbon Black-based Photoresist for LCD Color-Filter," Polymer (Korea), vol. 25, No. 1, 2011, 8 pgs.
Kerker, "The Scattering of Light and Other Electromagnetic Radiation," Academic Press, San Diego, 1969, at 38, 686 pgs.
Klein and Cook, "Unified approach to ultrasonic light diffraction," IEEE Transaction on Sonics and Ultrasonics, SU-14, 123-134, 1967, 12 pgs.
Koji Arimitsu et al., "Preparation of Base-Amplifying Microcapsules and Their Application to Photoreactive Materials," Journal of Polymer Science, Part A: Polymer Chemistry, vol. 53, No. 21, Nov. 1, 2015, 4 pgs.
Landry et al., Novel Miscible Blends of Etheric Polyphosphazenes with Acidic Polymers, Macromolecules, vol. 26, 35-46, 1993, 12 pgs.
Lesnichii et al., "Study of diffusion in bulk polymer films below glass transition: evidences of dynamical heterogeneities," J. Phys.: Conf. Ser. 1062 012020, 2018, 6 pgs.
Ludman et al., "Very thick holographic nonspatial filtering of laser beams," Optical Engineering, vol. 36, No. 6, 1700-1705, Jun. 1997, 6 pgs.
Murali and Eisenberg, Ionic Miscibility Enhancement in Poly(tetrafluoroethylene) / Poly(ethyl acrylate) Blends. I. Dynamic Mechanical Studies, Journal of Polymer Science, Part B: Polymer, Physics, vol. 26, 1385-1396, 1988, 12 pgs.
Nakawaga, Yu, Synthesis of Highly Refractive Poly(phenylene thioether) Derived from 2,4-Dicloro-6-alkylthio-1,3,5-triazines and Aromatic Dithiols, Macromolecules, ACS Publications, © 2011 American Chemical Society, 7 pgs.
Natansohn et al., Miscibility Enhancement in Polymers Via Ionic Interactions: Dynamic Mechanical and NMR Studies, Makromol. Chem., Macromol. Symp., 16, 175-193, 1988, 19 pgs.
Olabisi et al., "Polymer-Polymer Miscibility," Academic Press, New York, 1979, 384 pgs.
Piton and Natansohn, Charge-Transfer Interactions in Copolymer Blends. 3.Poly[(N-ethylcarbazol-3-yl)methyl] methacrylate-co-styrene] Blended with Poly[2-[(3,5-dinitrobenzoyl)oxy]ethyl methacrylate-co-methyl methacrylate], Macromolecules, vol. 28, No. 5, 1995, 4 pgs.
Nakabayashi, Poly(phenylene thioether)s with Fluorene-Based Cardo Structure toward High Transparency, High Refractive Index, and Low Birefringence, Macromolecules, 2016, 49 (16), pp. 5849-5856, 7 pgs.
Sigma-Aldrich, "Controlled Radical Polymerization Guide: ATRP, RAFT, NMP," Aldrich, 2012, 52 pgs.
Smothers et al., "Photopolymers for Holography," SPIE OE/Laser Conference, 1212-03, Los Angeles, Calif., 1990, 10 pgs.

(56) References Cited

OTHER PUBLICATIONS

Taylor-Smith and Register, Probing Interdomain Mixing Effects via Specific Interactions: A Model System Approach, Macromolecules, vol. 26, No. 11, 1993, pp. 2802-2809, 8 pgs.
White and Mirau, Heteronuclear Correlation in Solid Polymers: Identification of Hydrogen Bond Donors and Acceptors in Miscible Polymer Blends, Macromolecules, vol. 27, No. 6, 1994, pp. 1648-1650, 3 pgs.
White and Mirau, Probin Miscibility and Intermolecular Interactions in Solid Polymer Blends Using the Nuclear Overhauser Effect, Macromolecules, vol. 26, No. 12, 1993, pp. 3049-3054, 6 pgs.
Zhou and Eisenberg, Ionomeric Blends, II. Compatibility and Dynamic Mechanical Properties of Sulfonated cis-1, 4-Polyisoprenes and Styrene/4-Vinylpyridine Copolymer Blends, Journal of Polymer Science, Polymer Physics Edition, vol. 21, 595-603, (1983), 9 pgs.
Zhao X., et al., "Synthesis and Charcterization of Thianthrene-Based Epoxy with High Refractive Index Over 1.7," Phosphorus, Sulfur and Silicon and the Related Elements, Sep. 5, 2017, vol. 193 (1), XP055704972, pp. 33-40.
Clark K.J., "A New Method for the Preparation of 9:10 Disubstituted Anthracenes," Journal of the Chemical Society, 1956, pp. 1511-1515.
Corrected Notice of Allowability dated Jan. 9, 2023 for U.S. Appl. No. 17/098,130, filed Nov. 13, 2020, 6 pages.
Final Office Action dated Feb. 17, 2023 for U.S. Appl. No. 16/779,446, filed Jan. 31, 2020, 8 pages.
Hailer., et al., "Action of o- and p-anisyl Magnesium Bromide on Anthraquinone and 13-methylanthraquinone", Comptes Rendus, 1910, vol. 150, pp. 1290-1295.
Non-Final Office Action dated Dec. 9, 2022 for U.S. Appl. No. 16/778,492, filed Jan. 31, 2020, 11 pages.
Non-Final Office Action dated Jan. 12, 2023 for U.S. Appl. No. 17/098,166, filed Nov. 13, 2020, 15 pages.
Non-Final Office Action dated Jan. 19, 2023 for U.S. Appl. No. 17/098,187, filed Nov. 13, 2020, 23 pages.
Non-Final Office Action dated Dec. 22, 2022 for U.S. Appl. No. 17/375,874, filed Jul. 14, 2021, 17 pages.
Non-Final Office Action dated Jan. 23, 2023 for U.S. Appl. No. 17/098,173, filed Nov. 13, 2020, 17 pages.
Non-Final Office Action dated Jan. 24, 2023 for U.S. Appl. No. 16/865,066, filed May 1, 2020, 10 pages.
Notice of Allowance dated Dec. 21, 2022 for U.S. Appl. No. 17/098,130, filed Nov. 13, 2020, 9 pages.
Notice of Allowance dated Jan. 26, 2023 for U.S. Appl. No. 17/386,280, filed Jul. 27, 2021, 9 pages.
Office Action dated Dec. 8, 2022 for Chinese Application No. 202080033443.4, filed May 5, 2020, 17 pages.
Final Office Action dated Oct. 28, 2022 for U.S. Appl. No. 17/098,146, filed Nov. 13, 2020, 17 pages.
International Preliminary Report on Patentability for International Application No. PCT/US2021/059208, dated May 25, 2023, 10 pages.
International Preliminary Report on Patentability for International Application No. PCT/US2021/059241, dated May 25, 2023, 10 pages.
Non-Final Office Action dated May 16, 2023 for U.S. Appl. No. 17/515,208, filed Oct. 29, 2021, 19 pages.
Notice of Allowance dated May 18, 2023 for U.S. Appl. No. 17/386,280, filed Jul. 27, 2021, 4 pages.
Office Action dated May 4, 2023 for Chinese Patent Application No. 202080031926.0, filed on Oct. 27, 2021, 10 pages.
Corrected Notice of Allowance dated Mar. 15, 2023 for U.S. Appl. No. 17/386,280, filed Jul. 27, 2021, 4 pages.
Final Office Action dated Apr. 3, 2023 for U.S. Appl. No. 16/778,492, filed Jan. 31, 2020, 16 pages.
Final Office Action dated May 5, 2023 for U.S. Appl. No. 17/098,173, filed Nov. 13, 2020, 12 pages.
Lan H., et al., "UV-Nanoimprint Lithography: Structure, Materials and Fabrication of Flexible Molds," Journal of Nanoscience and Nanotechnology, May 2013, vol. 13 (5), pp. 3145-3172.
Non-Final Office Action dated Mar. 17, 2023 for U.S. Appl. No. 17/098,146, filed Nov. 13, 2020, 16 pages.
Non-Final Office Action dated Apr. 21, 2023 for U.S. Appl. No. 17/098,166, filed Nov. 13, 2020, 10 pages.
Notice of Allowance dated May 2, 2023 for U.S. Appl. No. 17/375,874, filed Jul. 14, 2021, 10 pages.
Notice of Allowance dated May 8, 2023 for U.S. Appl. No. 17/386,280, filed Jul. 27, 2021, 10 pages.
Notice of Allowance dated Mar. 31, 2023 for U.S. Appl. No. 17/098,130, filed Nov. 13, 2020, 7 pages.
Patel M., et al, "Novel Catechol-Derived Phosphorus-Based Precursors for Coating Applications," Polymer Bulletin, Jun. 21, 2019, vol. 77, pp. 2183-2203.
Zhu Z., et al., "UV-Based Nanoimprinting Lithography with a Fluorinated Flexible Stamp," Journal of Vacuum Science & Technology B, Mar. 2011, vol. 29, No. 2, 7 pages.

* cited by examiner

FLUORENE DERIVATIZED MONOMERS AND POLYMERS FOR VOLUME BRAGG GRATINGS

RELATED APPLICATION

This application claims the benefit of, and priority to, U.S. Provisional Patent Application Ser. No. 62/845,258, filed May 8, 2019, which is incorporated by reference herein in its entirety.

FIELD

Described herein are recording materials for volume holograms, volume holographic elements, volume holographic gratings, and the like, as well as the volume holograms, volume holographic elements, volume holographic gratings produced by writing or recording such recording materials.

BACKGROUND

Polymeric substrates are disclosed in the art of holographic recording media, including for example photosensitive polymer films. See, e.g., Smothers et al., "Photopolymers for Holography," SPIE OE/Laser Conference, 1212-03, Los Angeles, Calif., 1990. The holographic recording media described in this article contain a photoimageable system containing a liquid monomer material (the photoactive monomer) and a photoinitiator (which promotes the polymerization of the monomer upon exposure to light), where the photoimageable system is in an organic polymer host matrix that is substantially inert to the exposure light. During writing (recording) of information into the material (by passing recording light through an array representing data), the monomer polymerizes in the exposed regions. Due to the lowering of the monomer concentration caused by the polymerization, monomer from the dark, unexposed regions of the material diffuses to the exposed regions. See, e.g., Colburn and Haines, "Volume Hologram Formation in Photopolymer Materials," Appl. Opt. 10, 1636-1641, 1971. The polymerization and resulting diffusion create a refractive index change, referred to as Δn, thus forming the hologram (holographic grating) representing the data.

Chain length and degree of polymerization are usually maximized and driven to completion in photopolymer systems used in conventional applications such as coatings, sealants, adhesives, etc., usually by using high light intensities, multifunctional monomers, high concentrations of monomers, heat, etc. Similar approaches were used in holographic recording media known in the art by using organic photopolymer formulations high in monomer concentration. See, for example, U.S. Pat. Nos. 5,874,187 and 5,759,721, disclosing "one-component" organic photopolymer systems. However, such one-component systems typically have large Bragg detuning values if they are not precured with light to some extent.

Improvements in holographic photopolymer media have been made by separating the formation of a polymeric matrix from the photochemistry used to record holographic information. See, for example, U.S. Pat. Nos. 6,103,454 and 6,482,551, disclosing "two-component" organic photopolymer systems. Two-component organic photopolymer systems allow for more uniform starting conditions (e.g., regarding the recording process), more convenient processing and packaging options, and the ability to obtain higher dynamic range media with less shrinkage or Bragg detuning.

Such two-component systems have various issues that need improvement. For example, the performance of a holographic photopolymer is determined strongly by how species diffuse during polymerization. Usually, polymerization and diffusion are occurring simultaneously in a relatively uncontrolled fashion within the exposed areas. This leads to several undesirable effects: for example, polymers that are not bound to the matrix after polymerization initiation or termination reactions are free to diffuse out of exposed regions of the film into unexposed areas, which "blurs" the resulting fringes, reducing Δn and diffraction efficiency of the final hologram. The buildup of Δn during exposure means that subsequent exposures can scatter light from these gratings, leading to the formation of noise gratings. These create haze and a loss of clarity in the final waveguide display. As described herein, for a series of multiplexed exposures with constant dose/exposure, the first exposures will consume most of the monomer, leading to an exponential decrease in diffraction efficiency with each exposure. A complicated "dose scheduling" procedure is required to balance the diffraction efficiency of all of the holograms.

Generally, the storage capacity of a holographic medium is proportional to the medium's thickness. Deposition onto a substrate of a pre-formed matrix material containing the photoimageable system typically requires use of a solvent, and the thickness of the material is therefore limited, e.g., to no more than about 150 μm, to allow enough evaporation of the solvent to attain a stable material and reduce void formation. Thus, the need for solvent removal inhibits the storage capacity of a medium.

In contrast, in volume holography, the media thickness is generally greater than the fringe spacing, and the Klein-Cook Q parameter is greater than 1. See Klein and Cook, "Unified approach to ultrasonic light diffraction," IEEE Transaction on Sonics and Ultrasonics, SU-14, 123-134, 1967. Recording mediums formed by polymerizing matrix material in situ from a fluid mixture of organic oligomer matrix precursor and a photoimageable system are also known.

Because little or no solvent is typically required for deposition of these matrix materials, greater thicknesses are possible, e.g., 200 μm and above. However, while useful results are obtained by such processes, the possibility exists for reaction between the precursors to the matrix polymer and the photoactive monomer. Such reaction would reduce the refractive index contrast between the matrix and the polymerized photoactive monomer, thereby affecting to an extent the strength of the stored hologram.

SUMMARY

The disclosure provides a compound of Formula I:

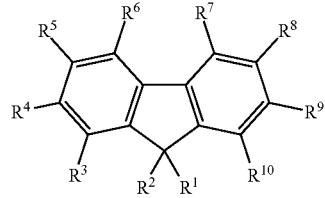

Formula I where in Formula I each $R^1$ to $R^{10}$ is independently hydrogen or a substituent including one or more groups selected from optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, hydroxy, halo, cyano, trifluoromethyl, trifluoromethoxy, nitro, trimethylsilanyl, optionally substituted epoxide, optionally substituted glycidyl, optionally substituted acrylate, optionally substituted methacrylate, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$, —S(O)$_t$OR$^a$, —S(O)$_t$N(R$^a$)$_2$, —S(O)$_t$N(R$^a$)C(O)R$^a$, —O(O)P(OR$^a$)$_2$, and —O(S)P(OR$^a$)$_2$; t is 1 or 2; each R$^a$ is independently selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, and optionally substituted heteroarylalkyl; and wherein at least one of R$^1$ to R$^{10}$ includes a polymerizable or crosslinkable group. In some embodiments, the compound has Formula I(a):

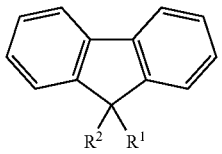

Formula I(a)

In some embodiments, the disclosure provides a compound of Formula I, or a compound of Formula I(a), wherein a substituent includes one or more linking groups selected from —C$_{1-10}$ alkyl-, —O—C$_{1-10}$ alkyl-, —C$_{1-10}$ alkenyl-, —O—C$_{1-10}$ alkenyl-, —C$_{1-10}$ cycloalkenyl-, —O—C$_{1-10}$ cycloalkenyl-, —C$_{1-10}$ alkynyl-, —O—C$_{1-10}$ alkynyl-, —C$_{1-10}$ aryl-, —O—C$_{1-10}$ aryl-, —O—, —S—, —C(O)—, —C(O)O—, —OC(O)—, —OC(O)O—, —N(R$^b$)—, —C(O)N(R$^b$)—, —N(R$^b$)C(O)—, —OC(O)N(R$^b$)—, —N(R$^b$)C(O)O—, —N(R$^b$)C(O)N(R$^b$)—, —N(R$^b$)C(NR$^b$)N(R$^b$)—, —N(R$^b$)S(O)$_w$—, —S(O)$_w$N(R$^b$)—, —S(O)$_w$O—, —OS(O)$_w$—, —OS(O)O—, —O(O)P(OR$^b$)O—, (O)P(O—)$_3$, —O(S)P(OR$^b$)O—, and (S)P(O—)$_3$, wherein w is 1 or 2, and R$^b$ is independently hydrogen, optionally substituted alkyl, or optionally substituted aryl. In some embodiments, the substituent includes one or more linking groups selected from —(CH$_2$)—, 1,2 disubstituted phenyl, 1,3 disubstituted phenyl, 1,4 disubstituted phenyl, disubstituted glycidyl, trisubstituted glycidyl, —CH=CH—, —C≡C—, —O—, —S—, —S(O)$_2$—, —C(O)—, —C(O)O—, —OC(O)—, —OC(O)O—, —NH—, —C(O)NH—, —NHC(O)—, —OC(O)NH—, —NHC(O)O—, —SC(O)NH—, —NHC(O)S—, —NHC(O)NH—, —NHC(NH)NH—, —NHS(P)$_2$—, —S(O)$_2$NH—, —S(O)$_2$O—, —OS(O)$_2$—, —OS(O)O—, (O)P(O—)$_3$, and (S)P(O—)$_3$, wherein n is an integer from 1 to 12. In some embodiments, the substituent includes one or more linking groups selected from —(CH$_2$)$_2$—, 1,4 disubstituted phenyl, —CH=CH—, —O—, —C(O)—, —C(O)O—, —OC(O)—, —NH—, —C(O)NH—, —NHC(O)—, —OC(O)NH—, —NHC(O)O—, and (S)P(O—)$_3$. In some embodiments, the substituent includes one or more linking groups selected from —(CH$_2$)—, —(CH$_2$)$_2$—, —(CH$_2$)$_3$—, —(CH$_2$)$_4$—, —(CH$_2$)—, —(CH$_2$)$_6$—, 1,4 disubstituted phenyl, disubstituted glycidyl, trisubstituted glycidyl, —CH=CH—, —O—, —C(O)—, —C(O)O—, —OC(O)—, —NH—, —C(O)NH—, —NHC(O)—, —OC(O)NH—, —NHC(O)O—, —SC(O)NH—, —NHC(O)S—, and (S)P(O—)$_3$. In some embodiments, the substituent includes one or more terminal groups selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, optionally substituted acrylate, optionally substituted methacrylate, optionally substituted styrene, optionally substituted epoxide, optionally substituted thiirane, optionally substituted glycidyl, optionally substituted lactone, optionally substituted carbonate, hydroxy, halo, cyano, trifluoromethyl, trifluoromethoxy, nitro, and trimethylsilanyl. In some embodiments, the substituent includes one or more terminal groups selected from alkenyl and cycloalkenyl. In some embodiments, the substituent includes one or more terminal groups selected from optionally substituted acrylate, optionally substituted methacrylate, optionally substituted vinyl, and optionally substituted allyl. In some embodiments, the one or more terminal groups are selected from alkenyl, cycloalkenyl, optionally substituted aryl, and optionally substituted heteroaryl. In some embodiments, the one or more terminal groups are selected from optionally substituted acrylate, optionally substituted methacrylate, optionally substituted vinyl, optionally substituted allyl, optionally substituted epoxide, optionally substituted thiirane, optionally substituted glycidyl, and optionally substituted allyl. In some embodiments, the one or more terminal groups are selected from vinyl, allyl, epoxide, thiirane, glycidyl, acrylate, and methacrylate. In some embodiments, the one or more terminal groups are selected from optionally substituted thiophenyl, optionally substituted thiopyranyl, optionally substituted thienothiophenyl, and optionally substituted benzothiophenyl. In some embodiments, the substituent includes one or more terminal groups selected from acrylate and methacrylate. In some embodiments, the polymerizable or crosslinkable group is selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted thiirane, optionally substituted glycidyl, optionally substituted lactone, optionally substituted lactam, and optionally substituted carbonate. In some embodiments, the polymerizable or crosslinkable group is selected from vinyl, allyl, epoxide, thiirane, glycidyl, acrylate and methacrylate. In some embodiments, the disclosure provides a compound comprising a substituent comprising at least an aryl group Ar, wherein Ar is selected from substituted phenyl, substituted naphthyl, substituted anthracenyl, substituted phenanthrenyl, substituted phenalenyl, substituted tetracenyl, substituted chrysenyl, substituted triphenylenyl, and substituted pyrenyl. In some embodiments, Ar is selected from 1,2-substituted phenyl, 1,3-substituted phenyl, and 1,4-substituted phenyl. In some embodiments, Ar is 1,4-substituted phenyl.

In some embodiments, the substituent comprises one or more groups selected from
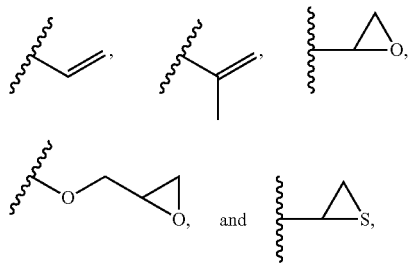
In some embodiments, the substituent comprises one or more groups selected from
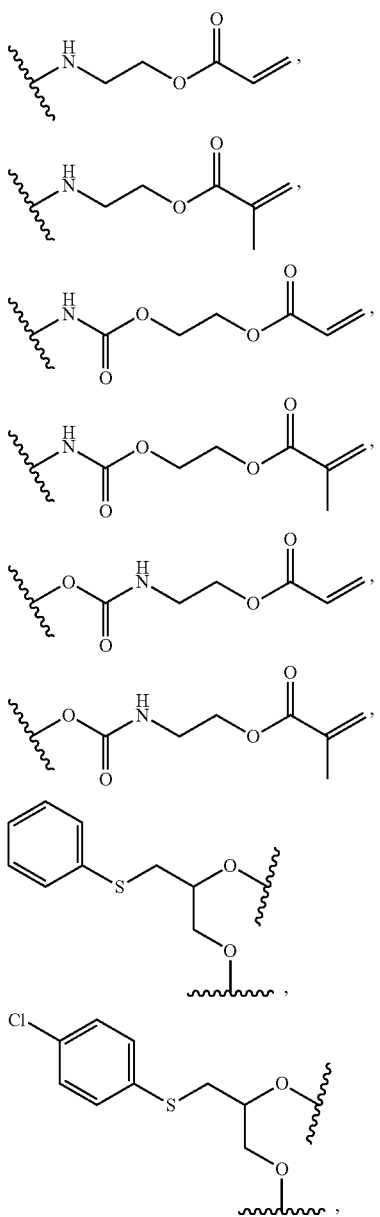
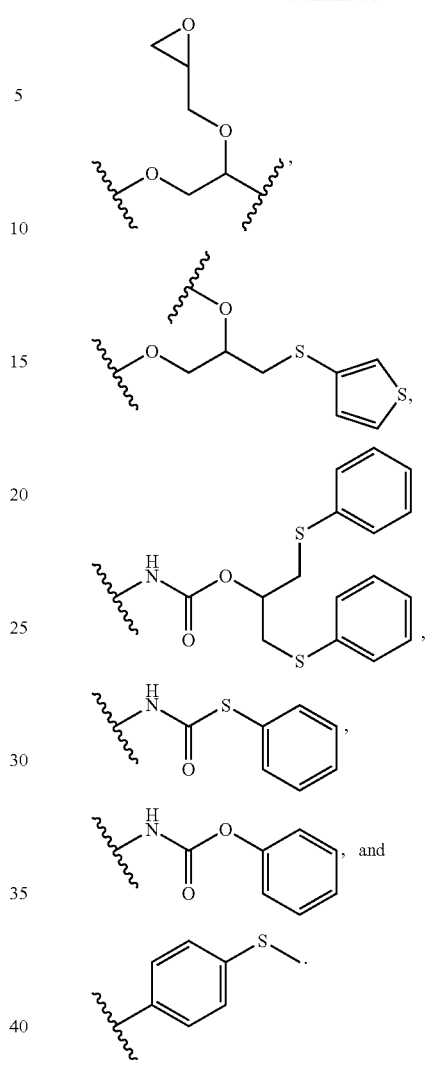
In some embodiments the substituent comprises one or more groups selected from:
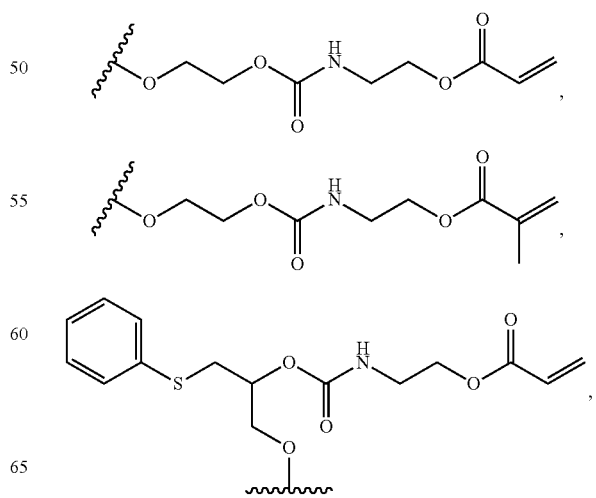

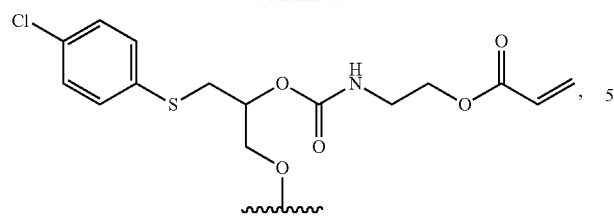,
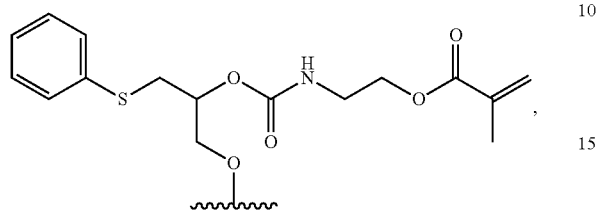,
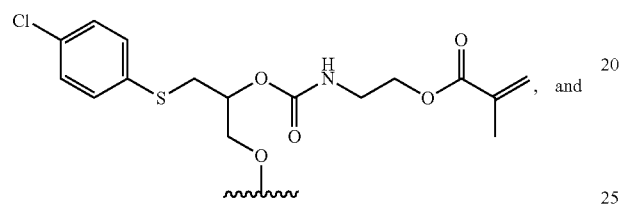, and
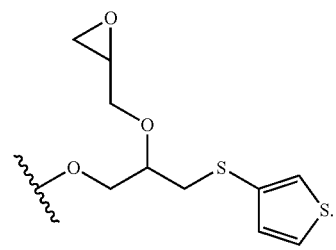.
In some embodiments, the disclosure provides a compound comprising one or more groups selected from:
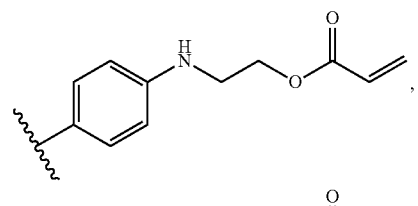,
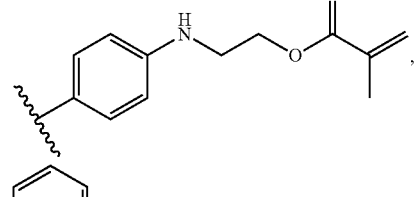,
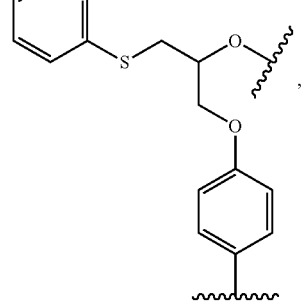,
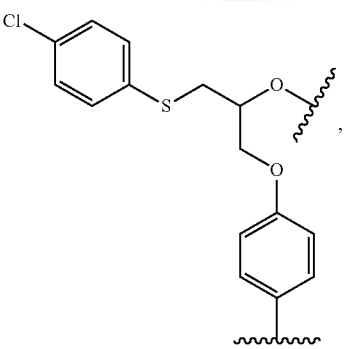,
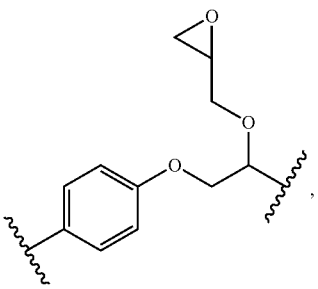,
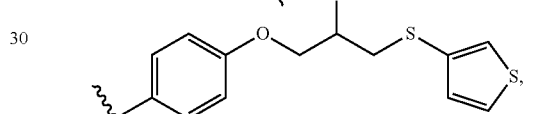,
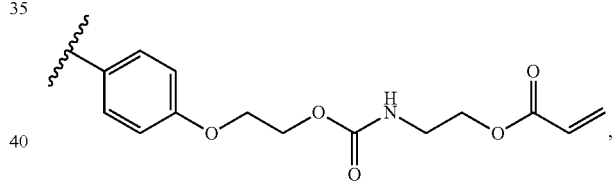,
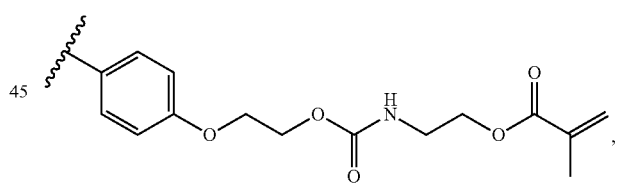,
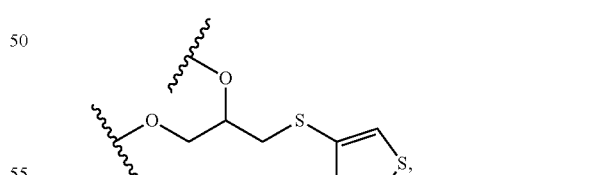,
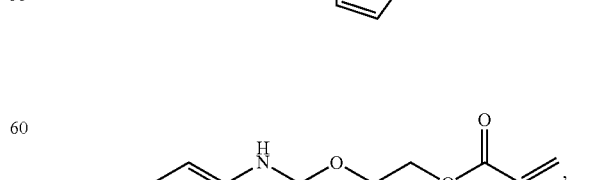,
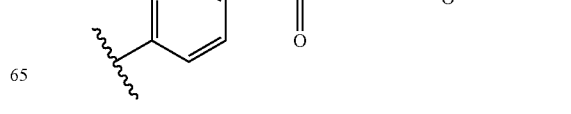, -continued
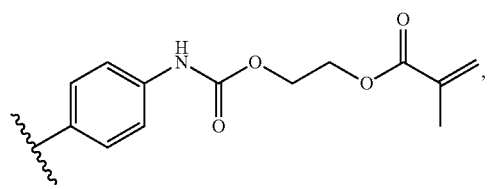,
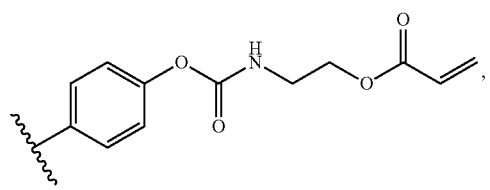,
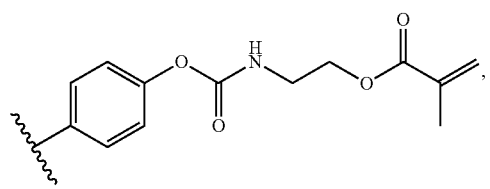,
,
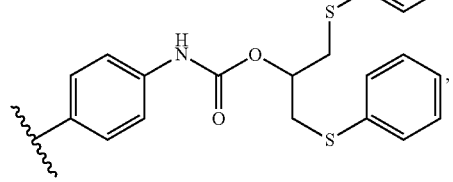, and
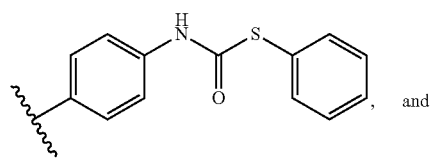.
In some embodiments, the compound comprises one or more groups selected from:
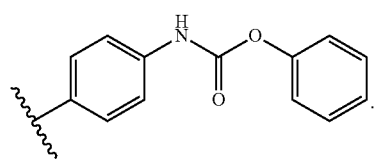,
-continued
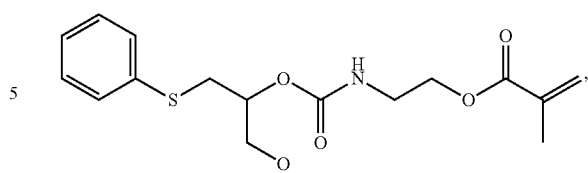,
,
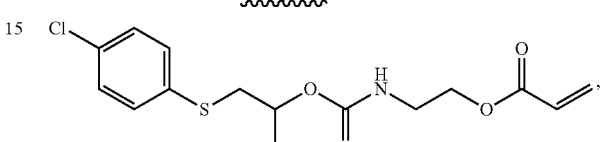,
,
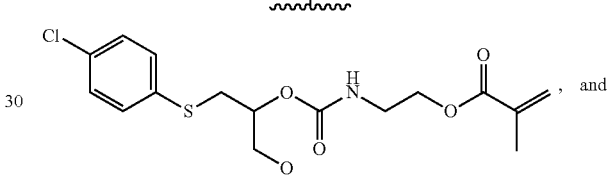, and
,
,
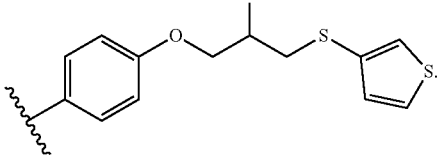.
In some embodiments, the substituent is selected from:
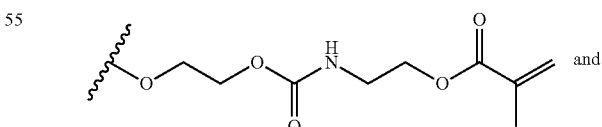 and
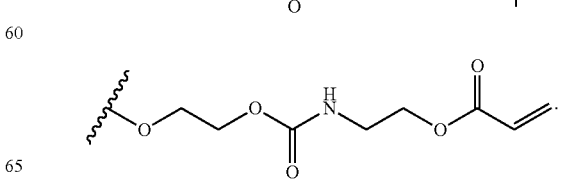.

The disclosure also provides a compound of Formula II:

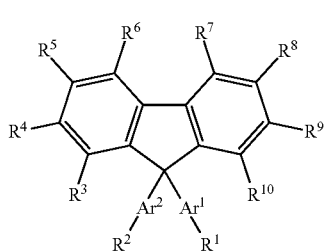

Formula II where in Formula II $Ar^1$ and $Ar^2$ are independently selected from a bond, optionally substituted alkyl, optionally substituted aryl, optionally substituted arylalkyl, optionally substituted heteroaryl, and optionally substituted heteroarylalkyl; each $R^1$ to $R^{10}$ is independently hydrogen or a substituent including one or more groups selected from optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, hydroxy, halo, cyano, trifluoromethyl, trifluoromethoxy, nitro, trimethylsilanyl, optionally substituted epoxide, optionally substituted glycidyl, optionally substituted acrylate, optionally substituted methacrylate, —$OR^a$, —$SR^a$, —OC(O)—$R^a$, —$N(R^a)_2$, —$C(O)R^a$, —$C(O)OR^a$, —$C(O)SR^a$, —$SC(O)R^a$, —OC(O)$OR^a$, —OC(O)N($R^a$)$_2$, —C(O)N($R^a$)$_2$, —N($R^a$)C(O)$OR^a$, —N($R^a$)C(O)$R^a$, —N($R^a$)C(O)N($R^a$)$_2$, N($R^a$)C(N$R^a$)N($R^a$)$_2$, —N($R^a$)S(O)$_t R^a$—S(O)$OR^a$, —S(O)$_t$N($R^a$)$_2$, —S(O)$_t$N($R^a$)C(O)$R^a$, —O(O)P(O$R^a$)$_2$, and —O(S)P(O$R^a$)$_2$; t is 1 or 2; each R is independently selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, and optionally substituted heteroarylalkyl; and wherein at least one of $R^1$ to $R^{10}$ includes a polymerizable or crosslinkable group. In some embodiments, the compound has Formula II(a) or Formula II(b):

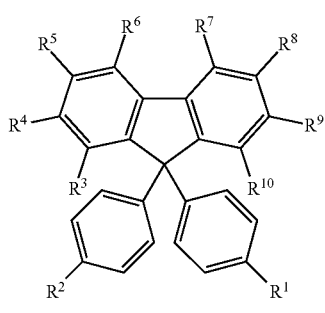

Formula II(a)

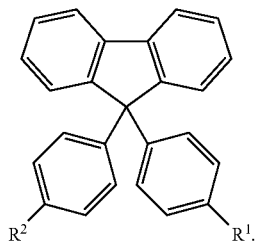

Formula II(b)

In some embodiments, in a compound of Formula I, Formula II(a), or Formula II(b), a substituent includes one or more linking groups selected from —$C_{1-10}$ alkyl-, —O—$C_{1-10}$ alkyl-, —$C_{1-10}$ alkenyl-, —O—$C_{1-10}$ alkenyl-, —$C_{1-10}$ cycloalkenyl-, —O—$C_{1-10}$ cycloalkenyl-, —$C_{1-10}$ alkynyl-, —O—$C_{1-10}$ alkynyl-, —$C_{1-10}$ aryl-, —O—$C_{1-10}$ aryl-, —O—, —S—, —C(O)—, —C(O)O—, —OC(O)—, —OC(O)O—, —N($R^b$)—, —C(O)N($R^b$)—, —N($R^b$)C(O)—, —OC(O)N($R^b$)—, —N($R^b$)C(O)O—, —N($R^b$)C(O)N($R^b$)—, —N($R^b$)C(N$R^b$)N($R^b$)—, —N(R)S(O)$_w$—, —S(O)$_w$N($R^b$)—, —S(O)$_w$O—, —OS(O)$_w$—, —OS(O)O$_w$—, —O(O)P(O$R^b$)O—, (O)P(O—)$_3$, —O(S)P(O$R^b$)O—, and (S)P(O—)$_3$, wherein w is 1 or 2, and $R^b$ is independently hydrogen, optionally substituted alkyl, or optionally substituted aryl. In some embodiments, the substituent includes one or more linking groups selected from —(CH$_2$)$_n$—, 1,2 disubstituted phenyl, 1,3 disubstituted phenyl, 1,4 disubstituted phenyl, —CH=CH—, —C≡C—, —O—, —S—, —C(O)—, —C(O)O—, —OC(O)—, —OC(O)O—, —NH—, —C(O)NH—, —NHC(O)—, —OC(O)NH—, —NHC(O)O—, —NHC(O)NH—, —NHC(NH)NH—, —NHS(O)$_2$—, —S(O)$_2$NH—, —S(O)$_2$O—, —OS(O)$_2$—, —OS(O)O—, (O)P(O—)$_3$, and (S)P(O—)$_3$, wherein n is an integer from 1 to 12. In some embodiments, the substituent includes one or more linking groups selected from —(CH$_2$)$_2$—, 1,4 disubstituted phenyl, —CH=CH—, —O—, —C(O)—, —C(O)O—, —OC(O)—, —NH—, —C(O)NH—, —NHC(O)—, —OC(O)NH—, —NHC(O)O—, and (S)P(O—)$_3$. In some embodiments, the substituent includes one or more linking groups selected from —(CH$_2$)—, —(CH$_2$)$_2$—, —(CH$_2$)$_3$—, —(CH$_2$)$_4$—, —(CH$_2$)$_5$—, —(CH$_2$)$_6$—, 1,4 disubstituted phenyl, disubstituted glycidyl, trisubstituted glycidyl, —CH=CH—, —O—, —C(O)—, —C(O)O—, —OC(O)—, —NH—, —C(O)NH—, —NHC(O)—, —OC(O)NH—, —NHC(O)O—, —SC(O)NH—, —NHC(O)S—, and (S)P(O—)$_3$. In some embodiments, the substituent includes one or more terminal groups selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, optionally substituted acrylate, optionally substituted methacrylate, optionally substituted styrene, optionally substituted epoxide, optionally substituted lactone, optionally substituted carbonate, hydroxy, halo, cyano, trifluoromethyl, trifluoromethoxy, nitro, and trimethylsilanyl. In some embodiments, the substituent includes one or more terminal groups selected from alkenyl and cycloalkenyl. In some embodiments, the substituent includes one or more terminal groups selected from optionally substituted acrylate, optionally substituted methacrylate, optionally substituted vinyl, and optionally substituted allyl. In some embodiments, the substituent includes one or more terminal groups selected from acrylate and methacrylate. In some embodiments, the polymerizable or crosslinkable group is selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted thiirane, optionally substituted glycidyl, optionally substituted lactone, and optionally substituted carbonate. In some embodiments, the polymerizable or crosslinkable group is selected from acrylate and methacrylate. In some embodiments, the substituent is selected from:
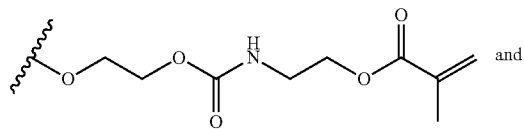 and
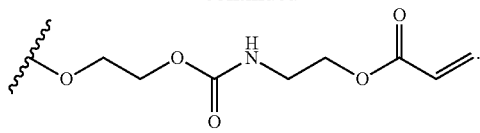
The disclosure also provides a compound of Formula II(c), Formula II(d), Formula II(e), Formula II(f), Formula II(g), Formula II(h), Formula II(i), or Formula II(j):
Formula II(c)
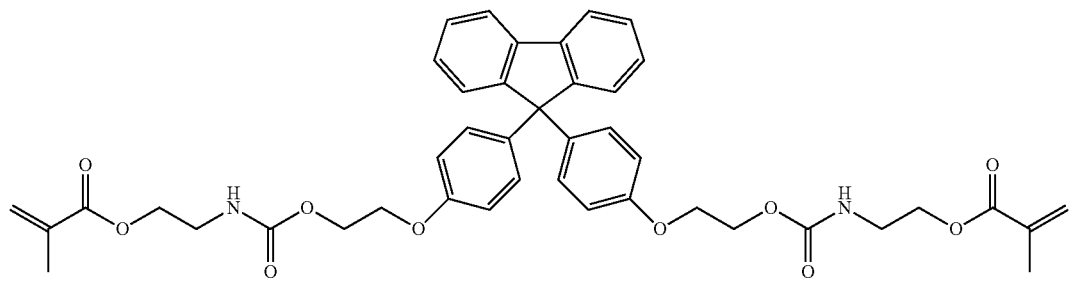
Formula II(d)
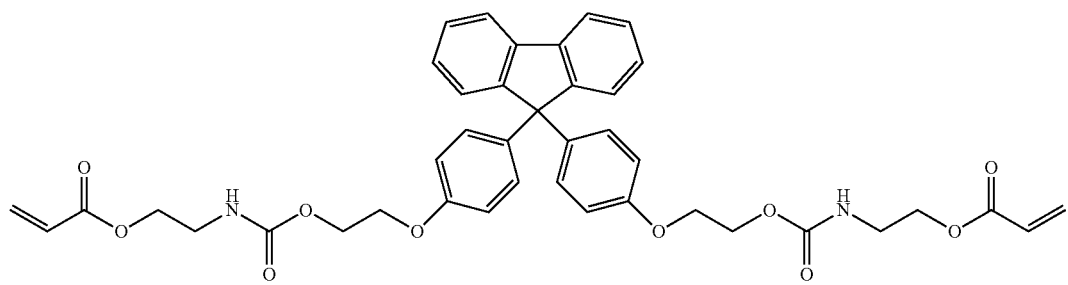
Formula II(e)
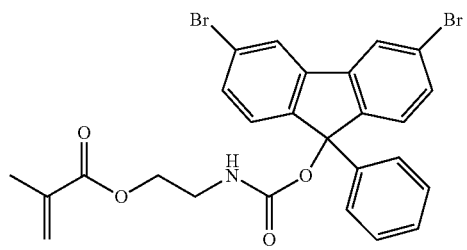
Formula II(f)
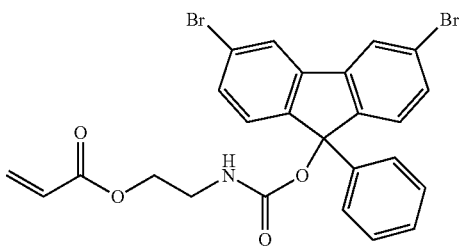
Formula II(g)
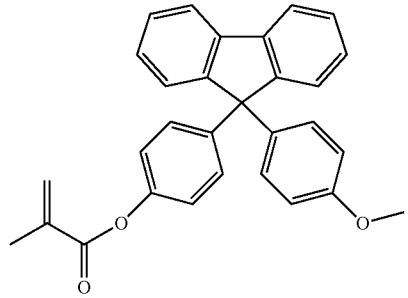
Formula II(h)
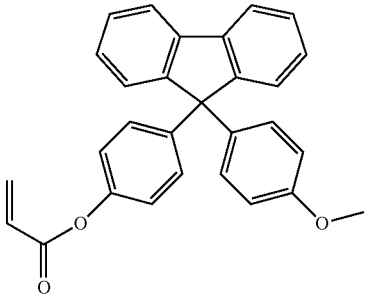

Formula II(i)

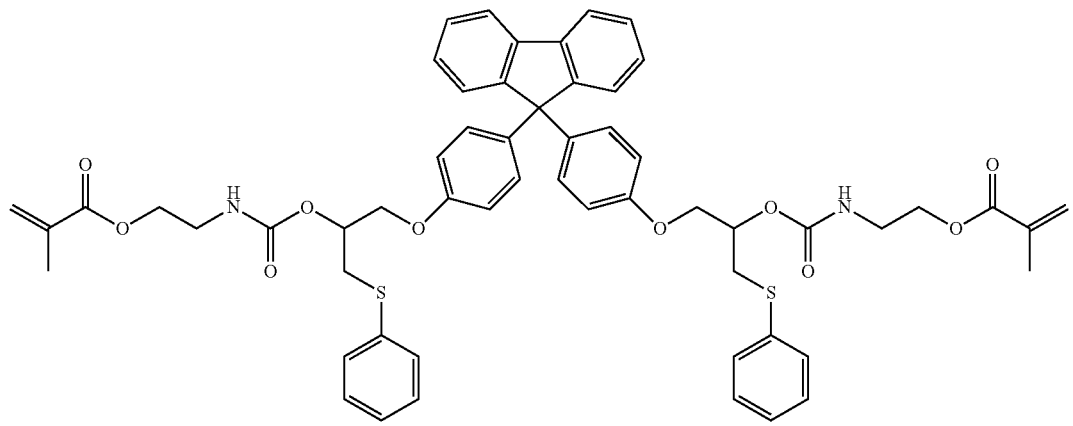

Formula II(j)

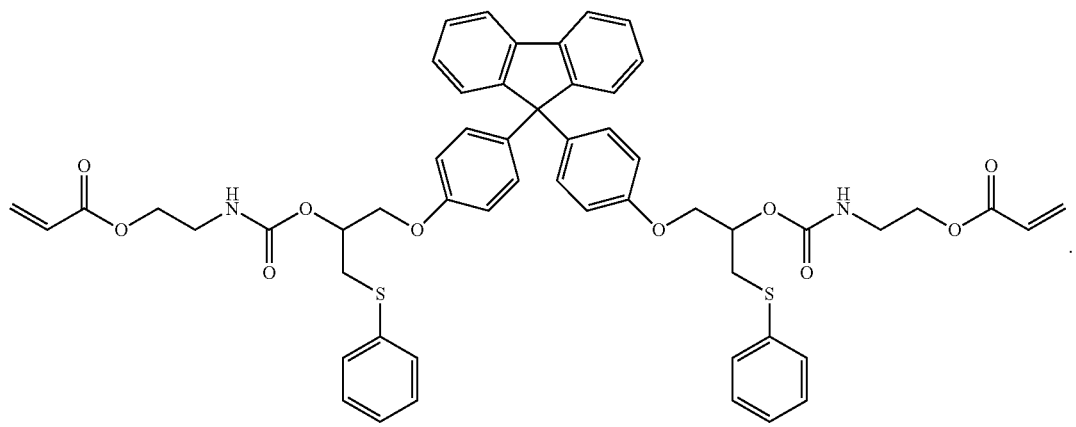

The disclosure also provides a compound of Formula III:

Formula III

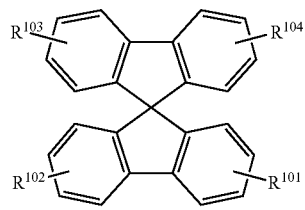

where in Formula III each $R^{101}$ to $R^{104}$ is independently a group of one, two, three, or four independently selected substituents, or no substituent, each substituent independently including one or more groups selected from optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, hydroxy, halo, cyano, trifluoromethyl, trifluoromethoxy, nitro, trimethylsilanyl, optionally substituted epoxide, optionally substituted glycidyl, optionally substituted acrylate, optionally substituted methacrylate, —$OR^a$, —$SR^a$, —OC(O)—$R^a$, —N($R^a$)$_2$, —C(O)$R^a$, —C(O)O$R^a$, —C(O)S$R^a$, —SC(O)$R^a$, —OC(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$, —S(O)$_t$O$R^a$, —S(O)$_t$N($R^a$)$_2$, —S(O)$_t$N($R^a$)C(O)$R^a$, (O)P(O$R^a$)$_3$, (S)P(OR)$_3$, and —(O)P(O$R^a$)$_2$; t is 1 or 2; each $R^a$ is independently selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, and optionally substituted heteroarylalkyl; and wherein at least one of $R^{101}$ to $R^{104}$ includes at least one substituent, the at least one substituent including a polymerizable or crosslinkable group.

In some embodiments, in the compound of Formula III, a substituent includes one or more linking groups selected from —$C_{1-10}$ alkyl-, —O—$C_{1-10}$ alkyl-, —$C_{1-10}$ alkenyl-, —O—$C_{1-10}$ alkenyl-, —$C_{1-10}$ cycloalkenyl-, —O—$C_{1-10}$ cycloalkenyl-, —$C_{1-10}$ alkynyl-, —O—$C_{1-10}$ alkynyl-, —$C_{1-10}$ aryl-, —O—$C_{1-10}$ aryl-, —O—, —S—, —C(O)—, —C(O)O—, —OC(O)—, —OC(O)O—, —N($R^a$)—, —C(O)N($R^b$), —N($R^b$)C(O)—, —OC(O)N($R^b$)—, —N($R^b$)C(O)O—, —N($R^b$)C(O)N($R^b$)—, —N($R^b$)C(N$R^b$)N($R^b$)—, —N($R^b$)S(O)$_w$—, —S(O)$_w$N($R^b$)—, —S(O)$_w$O—, —OS(O)$_w$—, —OS(O)$_w$O—, —O(O)P(O$R^b$)O—, (O)P(O—)$_3$, —O(S)P(O$R^b$)O—, and (S)P(O—)$_3$, wherein w is 1 or 2, and R is independently hydrogen, optionally substituted alkyl, or optionally substituted aryl. In some embodiments, the substituent includes one or more linking groups selected from —(CH$_2$)$_n$—, 1,2 disubstituted phenyl, 1,3 disubstituted phenyl, 1,4 disubstituted phenyl, —CH═CH—, —C≡C—, —O—, —S—, —C(O)—, —C(O)O—, —OC(O)—, —OC(O)O—, —NH—, —C(O)NH—, —NHC(O)—, —OC(O)NH—, —NHC(O)O—, —NHC(O)NH—, —NHC(NH)NH—, —NHS(O)$_2$—, —S(O)$_2$NH—, —S(O)$_2$O—, —OS(O)$_2$—, —OS(O)O—, (O)P(O—)$_3$, and (S)P(O—)$_3$, wherein n is an integer from 1 to 12. In some embodiments, the substituent includes one or more linking groups selected from —(CH$_2$)$_2$—, 1,4 disubstituted phenyl, —CH═CH—, —O—, —C(O)—, —C(O)O—, —OC(O)—, —NH—, —C(O)NH—, —NHC(O)—, —OC(O)NH—, —NHC(O)O—, and (S)P(O—)$_3$. In some embodiments, the substituent includes one or more linking groups selected from —(CH$_2$)—, —(CH$_2$)$_2$—, —(CH$_2$)$_3$—, —(CH$_2$)$_4$—, —(CH$_2$)$_5$—, —(CH$_2$)$_6$—, 1,4 disubstituted phenyl, disubstituted glycidyl, trisubstituted glycidyl, —CH═CH—, —O—, —C(O)—, —C(O)O—, —OC(O)—, —NH—, —C(O)NH—, —NHC(O)—, —OC(O)NH—, —NHC(O)O—, —SC(O)NH—, —NHC(O)S—, and (S)P(O—)$_3$. In some embodiments, the substituent includes one or more terminal groups selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, optionally substituted acrylate, optionally substituted methacrylate, optionally substituted styrene, optionally substituted epoxide, optionally substituted thiirane, optionally substituted glycidyl, optionally substituted lactone, optionally substituted carbonate, hydroxy, halo, cyano, trifluoromethyl, trifluoromethoxy, nitro, and trimethylsilanyl. In some embodiments, the substituent includes one or more terminal groups selected from alkenyl and cycloalkenyl. In some embodiments, the substituent includes one or more terminal groups selected from optionally substituted acrylate, optionally substituted methacrylate, optionally substituted vinyl, and optionally substituted allyl. In some embodiments, the one or more terminal groups are selected from alkenyl, cycloalkenyl, optionally substituted aryl, and optionally substituted heteroaryl. In some embodiments, the one or more terminal groups are selected from optionally substituted acrylate, optionally substituted methacrylate, optionally substituted vinyl, optionally substituted allyl, optionally substituted epoxide, optionally substituted thiirane, optionally substituted glycidyl, and optionally substituted allyl. In some embodiments, the one or more terminal groups are selected from vinyl, allyl, epoxide, thiirane, glycidyl, acrylate, and methacrylate. In some embodiments, the one or more terminal groups are selected from optionally substituted thiophenyl, optionally substituted thiopyranyl, optionally substituted thienothiophenyl, and optionally substituted benzothiophenyl. In some embodiments, the substituent includes one or more terminal groups selected from acrylate and methacrylate. In some embodiments, the polymerizable or crosslinkable group is selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted thiirane, optionally substituted glycidyl, optionally substituted lactone, optionally substituted lactam, and optionally substituted carbonate. In some embodiments, the polymerizable or crosslinkable group is selected from acrylate and methacrylate. In some embodiments, the disclosure provides a compound comprising a substituent comprising at least an aryl group Ar, wherein Ar is selected from substituted phenyl, substituted naphthyl, substituted anthracenyl, substituted phenanthrenyl, substituted phenalenyl, substituted tetracenyl, substituted chrysenyl, substituted triphenylenyl, and substituted pyrenyl. In some embodiments, Ar is selected from 1,2-substituted phenyl, 1,3-substituted phenyl, and 1,4-substituted phenyl. In some embodiments, Ar is 1,4-substituted phenyl. In some embodiments, the substituent is selected from:

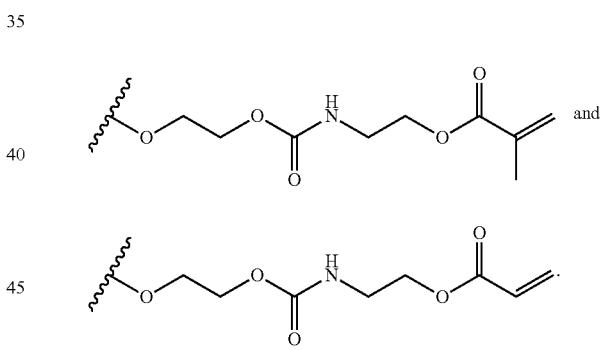

The disclosure also provides a compound of Formula III(a) and Formula III(b):

Formula III(a)

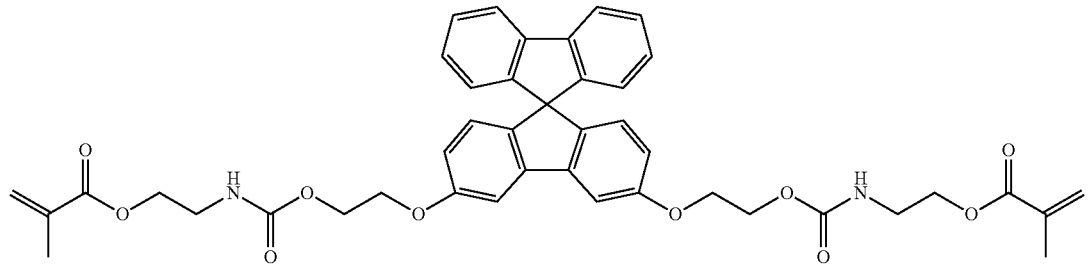

Formula III(b)

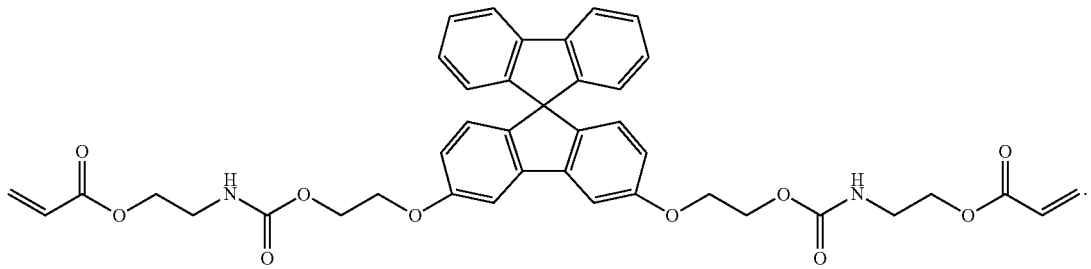

The disclosure also provides a resin mixture including a first polymer precursor including a compound of Formula I, Formula I(a), Formula II, Formula I(a), Formula II(b), Formula II(c), Formula II(d), Formula II(e), Formula II(f), Formula II(g), Formula II(h), Formula II(i), Formula II(j), Formula III, or Formula III(a), having any and all corresponding limitations described herein, and a second polymer precursor including a different compound including a polymerizable or crosslinkable group. In some embodiments, the different compound is selected from an alcohol and an isocyanate.

The disclosure also provides a polymeric material including a resin mixture including a first polymer precursor including a compound of Formula I, Formula I(a), Formula II, Formula II(a), Formula II(b), Formula II(c), Formula II(d), Formula I(e), Formula II(f), Formula (g), Formula II(h), Formula II(i), Formula II(j), Formula III, Formula III(a), or Formula III(b), having any and all corresponding limitations described herein, and a second polymer precursor including a different compound including a polymerizable or crosslinkable group, wherein the second polymer precursor is partially or totally polymerized or crosslinked. In some embodiments, the different compound is selected from an alcohol and an isocyanate. In some embodiments, the first polymer precursor is partially or totally polymerized or crosslinked.

The disclosure also provides a recording material for writing a volume Bragg grating, the material including a transparent support and a resin mixture including a first polymer precursor including a compound of Formula I, Formula I(a), Formula II, Formula (a), Formula II(b), Formula II(c), Formula II(d), Formula II(e), Formula II(f), Formula I(g), Formula II(h), Formula II(i), Formula II(j), Formula III, Formula III(a), or Formula III(b), having any and all corresponding limitations described herein, and a second polymer precursor including a different compound including a polymerizable or crosslinkable group. In some embodiments, the different compound is selected from an alcohol and an isocyanate. In some embodiments, the material has a thickness of between 1 μm and 500 μm.

The disclosure also provides a recording material for writing a volume Bragg grating, the material including a polymeric material including a resin mixture including a first polymer precursor including a compound of Formula I, Formula I(a), Formula II, Formula (a), Formula II(b), Formula II(c), Formula II(d), Formula II(e), Formula II(f), Formula (g), Formula II(h), Formula II(i), Formula II(j), Formula III, Formula III(a), or Formula III(b), having any and all corresponding limitations described herein, and a second polymer precursor including a different compound including a polymerizable or crosslinkable group, wherein the second polymer precursor is partially or totally polymerized or crosslinked. In some embodiments, the different compound is selected from an alcohol and an isocyanate. In some embodiments, the first polymer precursor is partially or totally polymerized or crosslinked. In some embodiments, the material has a thickness of between 1 μm and 500 μm.

The disclosure also provides a volume Bragg grating recorded on any recording material described herein, the grating characterized by a Q parameter equal to or greater than 5, wherein $$Q = \frac{2\pi\lambda_0 d}{n_0 \Lambda^2},$$

and wherein $\lambda_0$ is a recording wavelength, d is the thickness of the recording material, $n_0$ is a refractive index of the recording material, and $\Lambda$ is a grating constant.

BRIEF DESCRIPTION OF THE DRAWINGS

The foregoing summary, as well as the following detailed description of the present disclosure, will be better understood when read in conjunction with the appended drawings.

DETAILED DESCRIPTION

Figure 1:
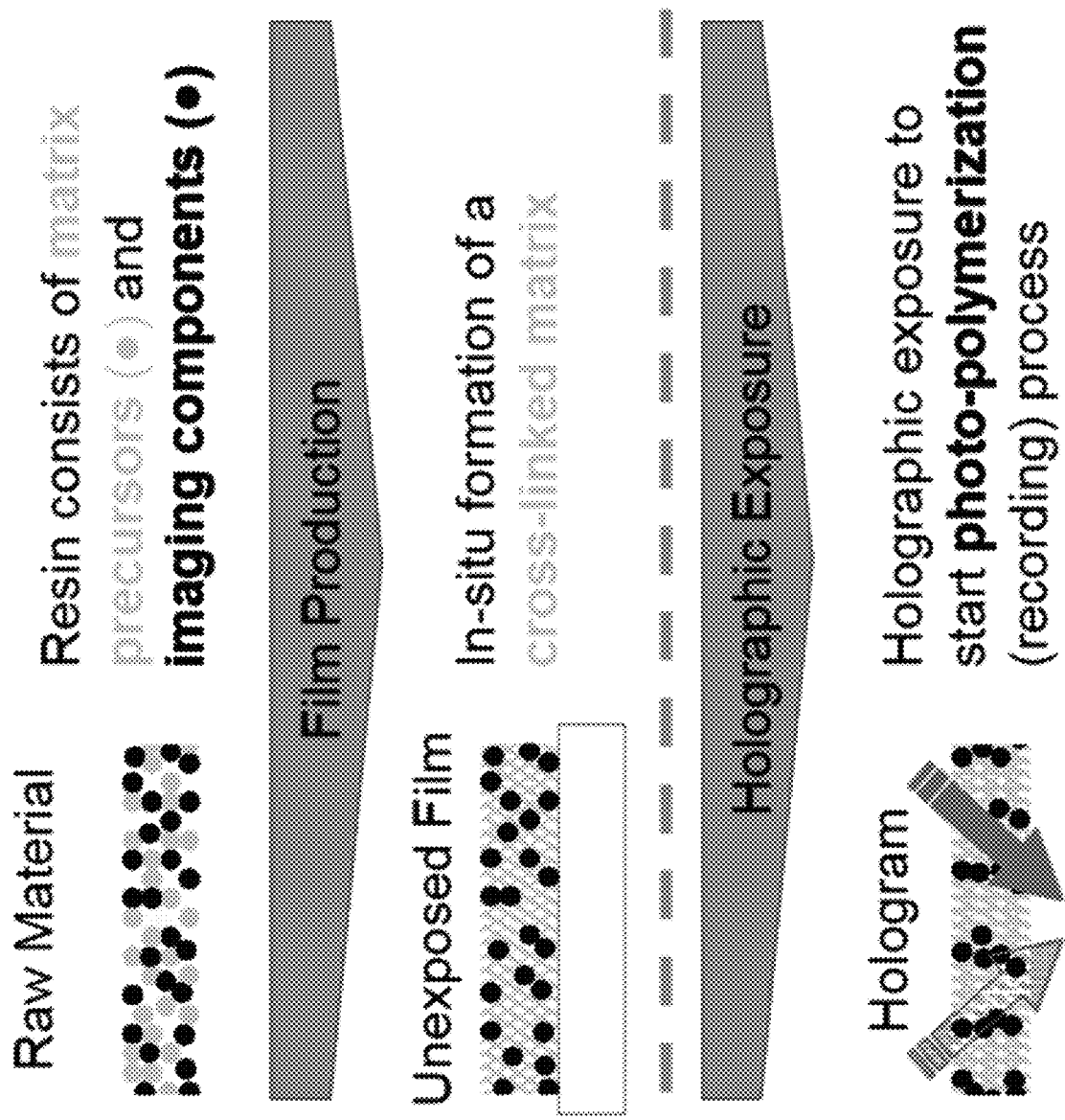
FIG. 1 illustrates generic steps for forming a volume Bragg grating (VBG). A raw material can be formed by mixing two different of precursors, e.g., a matrix precursor, and a photopolymerizable imaging precursor. The raw material can be formed into a film by curing or crosslinking, or partially curing or crosslinking the matrix precursor. Finally, holographic exposure initiates the curing or crosslinking of the photopolymerizable precursor which is the main step of the holographic recording process of making a VBG.

Volume gratings, usually produced by holographic technique and known as volume holographic gratings (VHG), volume Bragg gratings (VBG), or volume holograms, are diffractive optical elements based on material with periodic phase or absorption modulation throughout the entire volume of the material. When an incident light satisfies Bragg condition, it is diffracted by the grating. The diffraction occurs within a range of wavelength and incidence angles. In turn, the grating has no effect on the light from the off-Bragg angular and spectral range. These gratings also have multiplexing ability. Due to these properties, VHG/VBG are of great interest for various applications in optics such as data storage and diffractive optical elements for displays, fiber optic communication, spectroscopy, etc.

Achieving of the Bragg regime of a diffraction grating is usually determined by Klein parameter Q:

$$Q = \frac{2\pi\lambda d}{n\Lambda^2},$$

where d is a thickness of the grating, λ is the wavelength of light, Λ is the grating period, and n is the refractive index of the recording medium. As a rule, Bragg conditions are achieved if Q>>1, typically, Q≥10. Thus, to meet Bragg conditions, thickness of diffraction grating should be higher than some value determined by parameters of grating, recording medium and light. Because of this, VBG are also called thick gratings. On the contrary, gratings with Q<1 are considered thin, which typically demonstrates many diffraction orders (Raman-Nath diffraction regime).

Definitions

Unless defined otherwise, all technical and scientific terms used herein have the same meaning as is commonly understood by one of skill in the art to which this disclosure belongs. All patents and publications referred to herein are incorporated by reference in their entireties.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, or from 0% to 10%, or from 0% to 5% of the stated number or numerical range. The term "including" (and related terms such as "comprise" or "comprises" or "having" or "including") includes those embodiments such as, for example, an embodiment of any composition of matter, method or process that "consist of" or "consist essentially of" the described features.

As used herein, the term "light source" refers to any source of electromagnetic radiation of any wavelength. In some embodiments, a light source can be a laser of a particular wavelength.

As used herein, the term "photoinitiating light source" refers to a light source that activates a photoinitiator, a photoactive polymerizable material, or both. Photoiniating light sources include recording light, but are not so limited.

As used herein, the term "spatial light intensity" refers to a light intensity distribution or patterns of varying light intensity within a given volume of space.

As used herein, the terms "volume Bragg grating," "volume holographic grating," "holographic grating," and "hologram," are interchangeably used to refer to a recorded interference pattern formed when a signal beam and a reference beam interfere with each other.

In some embodiments, and in cases where digital data is recorded, the signal beam is encoded with a spatial light modulator.

As used herein, the term "holographic recording" refers to a holographic grating after it is recorded in the holographic recording medium.

As used herein, the term "holographic recording medium" refers to an article that is capable of recording and storing, in three dimensions, one or more holographic gratings. In some embodiments, the term refers to an article that is capable of recording and storing, in three dimensions, one or more holographic gratings as one or more pages as patterns of varying refractive index imprinted into an article.

As used herein, the term "diffraction efficiency" refers to the peak diffraction efficiency of a hologram measured in transmission.

As used herein, the term "data page" or "page" refers to the conventional meaning of data page as used with respect to holography. For example, a data page may be a page of data, one or more pictures, etc., to be recorded in a holographic recording medium, such as an article described herein.

As used herein, the term "recording light" refers to a light source used to record into a holographic medium. The spatial light intensity pattern of the recording light is what is recorded. Thus, if the recording light is a simple noncoherent beam of light, then a waveguide may be created, or if it is two interfering laser beams, then interference patterns will be recorded.

As used herein, the term "recording data" refers to storing holographic representations of one or more pages as patterns of varying refractive index.

As used herein, the term "reading data" refers to retrieving data stored as holographic representations.

As used herein, the term "exposure" refers to when a holographic recording medium was exposed to recording light, e.g., when the holographic grating was recorded in the medium.

As used herein, the terms "time period of exposure" and "exposure time" refer interchangeably to how long the holographic recording medium was exposed to recording light, e.g., how long the recording light was on during the recording of a holographic grating in the holographic recording medium. "Exposure time" can refer to the time required to record a single hologram or the cumulative time for recording a plurality of holograms in a given volume.

As used herein, the term "schedule" refers to the pattern, plan, scheme, sequence, etc., of the exposures relative to the cumulative exposure time in recording holographic gratings in a medium. In general, the schedule allows one to predict the time (or light energy) needed for each single exposure, in a set of plural exposures, to give a predetermined diffraction efficiency.

As used herein, the term "function" when used with the term "schedule" refers to a graphical plot or mathematical expression that defines or describes a schedule of exposures versus cumulative exposure time in recording plural holographic gratings.

As used herein, the term "substantially linear function" when used with the term "schedule" refers to a graphical plot of the schedule of exposures versus exposure time that provides a straight line or substantially a straight line.

As used herein, the term "support matrix" refers to the material, medium, substance, etc., in which the polymerizable component is dissolved, dispersed, embedded, enclosed, etc. In some embodiments, the support matrix is typically a low $T_g$ polymer. The polymer may be organic, inorganic, or a mixture of the two. Without being particularly limited, the polymer may be a thermoset or thermoplastic.

As used herein, the term "different form" refers to an article of the present disclosure being processed to form a product having a different form such as processing an article comprising a block of material, powder of material, chips of material, etc., into a molded product, a sheet, a free flexible film, a stiff card, a flexible card, an extruded product, a film deposited on a substrate, etc.

As used herein, the term "particle material" refers to a material that is made by grinding, shredding, fragmenting or otherwise subdividing an article into smaller components or to a material that is comprised of small components such as a powder.

As used herein, the term "free flexible film" refers to a thin sheet of flexible material that maintains its form without being supported on a substrate. Examples of free flexible films include, without limitation, various types of plastic wraps used in food storage.

As used herein, the term "stiff article" refers to an article that may crack or crease when bent. Stiff articles include, without limitation, plastic credit cards, DVDs, transparencies, wrapping paper, shipping boxes, etc.

As used herein, the term "volatile compound" refers to any chemical with a high vapor pressure and/or a boiling point below about 150° C. Examples of volatile compounds include: acetone, methylene chloride, toluene, etc. An article, mixture or component is "volatile compound free" if the article, mixture or component does not include a volatile compound.

As used herein, the term "oligomer" refers to a polymer having a limited number of repeating units, for example, but without limitation, approximately 30 repeat units or less, or any large molecule able to diffuse at least about 100 nm in approximately 2 minutes at room temperature when dissolved in an article of the present disclosure. Such oligomers may contain one or more polymerizable groups whereby the polymerizable groups may be the same or different from other possible monomers in the polymerizable component. Furthermore, when more than one polymerizable group is present on the oligomer, they may be the same or different. Additionally, oligomers may be dendritic. Oligomers are considered herein to be photoactive monomers, although they are sometimes referred to as "photoactive oligomer(s)".

As used herein, the term "photopolymerization" refers to any polymerization reaction caused by exposure to a photoinitiating light source.

As used herein, the term "resistant to further polymerization" refers to the unpolymerized portion of the polymerizable component having a deliberately controlled and substantially reduced rate of polymerization when not exposed to a photoinitiating light source such that dark reactions are minimized, reduced, diminished, eliminated, etc. A substantial reduction in the rate of polymerization of the unpolymerized portion of the polymerizable component according to the present disclosure can be achieved by any suitable composition, compound, molecule, method, mechanism, etc., or any combination thereof, including using one or more of the following: (1) a polymerization retarder; (2) a polymerization inhibitor; (3) a chain transfer agent; (4) metastable reactive centers; (5) a light or heat labile photo-terminator; (6) photo-acid generators, photo-base generators or photogenerated radicals; (7) polarity or solvation effects; (8) counter ion effects; and (9) changes in monomer reactivity.

As used herein, the term "substantially reduced rate" refers to a lowering of the polymerization rate to a rate approaching zero, and ideally a rate of zero, within seconds after the photoinitiating light source is off or absent. The rate of polymerization should typically be reduced enough to prevent the loss in fidelity of previously recorded holograms.

As used herein, the term "dark reaction" refers to any polymerization reaction that occurs in absence of a photoinitiating light source. In some embodiments, and without limitation, dark reactions can deplete unused monomer, can cause loss of dynamic range, can cause noise gratings, can cause stray light gratings, or can cause unpredictability in the scheduling used for recording additional holograms.

As used herein, the term "free radical polymerization" refers to any polymerization reaction that is initiated by any molecule comprising a free radical or radicals.

As used herein, the term "cationic polymerization" refers to any polymerization reaction that is initiated by any molecule comprising a cationic moiety or moieties.

As used herein, the term "anionic polymerization" refers to any polymerization reaction that is initiated by any molecule comprising an anionic moiety or moieties.

As used herein, the term "photoinitiator" refers to the conventional meaning of the term photoinitiator and also refers to sensitizers and dyes. In general, a photoinitiator causes the light initiated polymerization of a material, such as a photoactive oligomer or monomer, when the material containing the photoinitiator is exposed to light of a wavelength that activates the photoinitiator, e.g., a photoinitiating light source. The photoinitiator may refer to a combination of components, some of which individually are not light sensitive, yet in combination are capable of curing the photoactive oligomer or monomer, examples of which include a dye/amine, a sensitizer/iodonium salt, a dye/borate salt, etc.

As used herein, the term "photoinitiator component" refers to a single photoinitiator or a combination of two or more photoinitiators. For example, two or more photoinitiators may be used in the photoinitiator component of the present disclosure to allow recording at two or more different wavelengths of light.

As used herein, the term "polymerizable component" refers to one or more photoactive polymerizable materials, and possibly one or more additional polymerizable materials, e.g., monomers and/or oligomers, that are capable of forming a polymer.

As used herein, the term "polymerizable moiety" refers to a chemical group capable of participating in a polymerization reaction, at any level, for example, initiation, propagation, etc. Polymerizable moieties include, but are not limited to, addition polymerizable moieties and condensation polymerizable moieties. Polymerizable moieties include, but are not limited to, double bonds, triple bonds, and the like.

As used herein, the term "photoactive polymerizable material" refers to a monomer, an oligomer and combinations thereof that polymerize in the presence of a photoinitiator that has been activated by being exposed to a photoinitiating light source, e.g., recording light. In reference to the functional group that undergoes curing, the photoactive polymerizable material comprises at least one such functional group. It is also understood that there exist photoactive polymerizable materials that are also photoinitiators, such as N-methylmaleimide, derivatized acetophenones, etc., and that in such a case, it is understood that the photoactive monomer and/or oligomer of the present disclosure may also be a photoinitiator.

As used herein, the term "photopolymer" refers to a polymer formed by one or more photoactive polymerizable materials, and possibly one or more additional monomers and/or oligomers.

As used herein, the term "polymerization retarder" refers to one or more compositions, compounds, molecules, etc., that are capable of slowing, reducing, etc., the rate of polymerization while the photoinitiating light source is off or absent, or inhibiting the polymerization of the polymerizable component when the photoinitiating light source is off or absent. A polymerization retarder is typically slow to react with a radical (compared to an inhibitor), thus while the photoinitiating light source is on, polymerization continues at a reduced rate because some of the radicals are effectively terminated by the retarder. In some embodiments, at high enough concentrations, a polymerization retarder can potentially behave as a polymerization inhibitor. In some embodiments, it is desirable to be within the concentration range that allows for retardation of polymerization to occur, rather than inhibition of polymerization.

As used herein, the term "polymerization inhibitor" refers to one or more compositions, compounds, molecules, etc., that are capable of inhibiting or substantially inhibiting the polymerization of the polymerizable component when the photoinitiating light source is on or off. Polymerization inhibitors typically react very quickly with radicals and effectively stop a polymerization reaction. Inhibitors cause an inhibition time during which little to no photopolymer forms, e.g., only very small chains. Typically, photopolymerization occurs only after nearly 100% of the inhibitor is reacted.

As used herein, the term "chain transfer agent" refers to one or more compositions, compounds, molecules, etc. that are capable of interrupting the growth of a polymeric molecular chain by formation of a new radical that may react as a new nucleus for forming a new polymeric molecular chain. Typically, chain transfer agents cause the formation of a higher proportion of shorter polymer chains, relative to polymerization reactions that occur in the absence of chain transfer agents. In some embodiments, certain chain transfer agents can behave as retarders or inhibitors if they do not efficiently reinitiate polymerization.

As used herein, the term "metastable reactive centers" refers to one or more compositions, compounds, molecules, etc., that have the ability to create pseudo-living radical polymerizations with certain polymerizable components. It is also understood that infrared light or heat may be used to activate metastable reactive centers towards polymerization.

As used herein, the term "light or heat labile phototerminators" refers to one or more compositions, compounds, components, materials, molecules, etc., capable of undergoing reversible termination reactions using a light source and/or heat.

As used herein, the terms "photo-acid generators," "photo-base generators," and "photogenerated radicals," refer to one or more compositions, compounds, molecules, etc., that, when exposed to a light source, generate one or more compositions, compounds, molecules, etc., that are acidic, basic, or a free radical.

As used herein, the term "polarity or solvation effects" refers to an effect or effects that the solvent or the polarity of the medium has on the polymerization rate. This effect is most pronounced for ionic polymerizations where the proximity of the counter ion to the reactive chain end influences the polymerization rate.

As used herein, the term "counter ion effects" refers to the effect that counter ion, in ionic polymerizations, has on the kinetic chain length. Good counter ions allow for very long kinetic chain lengths, whereas poor counter ions tend to collapse with the reactive chain end, thus terminating the kinetic chain (e.g., causing smaller chains to be formed).

As used herein, the term "plasticizer" refers to the conventional meaning of the term plasticizer. In general, a plasticizer is a compound added to a polymer both to facilitate processing and to increase the flexibility and/or toughness of a product by internal modification (solvation) of a polymer molecule.

As used herein, the term "thermoplastic" refers to the conventional meaning of thermoplastic, e.g., a composition, compound, substance, etc., that exhibits the property of a material, such as a high polymer, that softens when exposed to heat and generally returns to its original condition when cooled to room temperature. Examples of thermoplastics include, but are not limited to: poly(methyl vinyl ether-alt-maleic anhydride), poly(vinyl acetate), poly(styrene), poly (propylene), poly(ethylene oxide), linear nylons, linear polyesters, linear polycarbonates, linear polyurethanes, etc.

As used herein, the term "room temperature thermoplastic" refers to a thermoplastic that is solid at room temperature, e.g., will not cold flow at room temperature.

As used herein, the term "room temperature" refers to the commonly accepted meaning of room temperature.

As used herein, the term "thermoset" refers to the conventional meaning of thermoset, e.g., a composition, compound, substance, etc., that is crosslinked such that it does not have a melting temperature. Examples of thermosets are crosslinked poly(urethanes), crosslinked poly(acrylates), crosslinked poly(styrene), etc.

Unless otherwise stated, the chemical structures depicted herein are intended to include compounds which differ only in the presence of one or more isotopically enriched atoms. For example, compounds where one or more hydrogen atoms is replaced by deuterium or tritium, or where one or more carbon atoms is replaced by $^{3}$C- or $^{14}$C-enriched carbons, are within the scope of this disclosure.

"Alkyl" refers to a straight or branched hydrocarbon chain radical consisting solely of carbon and hydrogen atoms, containing no unsaturation, having from one to ten carbon atoms (e.g., ($C_{1-10}$)alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), or PO$_3$(R$^a$)$_2$ where each R$^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocyclyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (e.g., ($C_{2-10}$)alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (e.g., vinyl), prop-1-enyl (e.g., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (e.g., ($C_{2-10}$)alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (e.g. (C$_{3-10}$)cycloalkyl or C$_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy where the alkyl constituent is substituted (e.g., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon where the alkoxy group has the indicated number of carbon atoms. Thus a (C$_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group where the alkoxy group is a lower alkoxy group.

The term "substituted alkoxycarbonyl" refers to the group (substituted alkyl)-O—C(O)— where the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, where the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R)C(O)R (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical where R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), —S(O)$_t$N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (e.g., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)N(R)C(O)R (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. It is understood that a substituent R attached to an aromatic ring at an unspecified position, (e.g.:

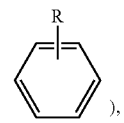

includes one or more, and up to the maximum number of possible substituents.

The term "aryloxy" refers to the group —O-aryl.

The term "substituted aryloxy" refers to aryloxy where the aryl substituent is substituted (e.g., —O-(substituted aryl)). Unless stated otherwise specifically in the specification, the aryl moiety of an aryloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., C$_1$-C$_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., C$_5$-C$_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofuranzanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (e.g., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O) SR$^a$, —SC(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)$_t$N(R$^a$)$_2$ (where t is 1 or 2), —S(O)$_t$N(R$^a$)C(O)R$^a$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, where the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R, —N(R$^a$)$_2$, —C(O)R$^a$, —C(O)OR$^a$, —C(O)SR$^a$, —SC(O) R$^a$, OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$) N(R$^a$)$_2$, —N(R$^a$)S(O)$_t$R$^a$ (where t is 1 or 2), —S(O)$_t$R$^a$, —S(O)$_t$OR$^a$ (where t is 1 or 2), —S(O)N(R$^a$)$_2$ (where t is 1 or 2), —S(O)$_t$N(R)C(O)R (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems where one non-aromatic ring, usually with 3 to 7 ring atoms, contains at least 2 carbon atoms in addition to 1-3 heteroatoms independently selected from oxygen, sulfur, and nitrogen, as well as combinations including at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —NO$_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—e.g., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In some embodiments, enantiomerically enriched compositions have different properties than the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site.

Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the present disclosure also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

For the avoidance of doubt, it is intended herein that particular features (for example integers, characteristics, values, uses, diseases, formulae, compounds or groups) described in conjunction with a particular aspect, embodiment or example of the disclosure are to be understood as applicable to any other aspect, embodiment or example described herein unless incompatible therewith. Thus, such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The present disclosure is not restricted to any details of any disclosed embodiments. The present disclosure extends to any novel one, or novel combination, of the features disclosed in this specification (including any accompanying claims, abstract and drawings), or to any novel one, or any novel combination, of the steps of any method or process so disclosed.

Volume Holography

A holographic recording medium described herein can be used in a holographic system. Formation of a hologram, waveguide, or other optical article relies on a refractive index contrast ($\Delta n$) between exposed and unexposed regions of a medium. The amount of information capable of being stored in a holographic medium is a function of the product of: the refractive index contrast, $\Delta n$, of the photorecording material, and the thickness, d, of the photorecording material. The refractive index contrast, $\Delta n$, is conventionally known, and is defined as the amplitude of the sinusoidal variations in the refractive index of a material in which a plane-wave, volume hologram has been written. The refractive index varies as:

$$n(x)=n_0+\Delta n \cos(K_x)$$

where n(x) is the spatially varying refractive index, x is the position vector, K is the grating wave vector, and $n_0$ is the baseline refractive index of the medium. See, e.g., P. Hariharan, Optical Holography: Principles, Techniques and Applications, Cambridge University Press, Cambridge, 1991, at 44, the disclosure of which is hereby incorporated by reference. The $\Delta n$ of a material is typically calculated from the diffraction efficiency or efficiencies of a single volume hologram or a multiplexed set of volume holograms recorded in a medium. The $\Delta n$ is associated with a medium before writing, but is observed by measurement performed after recording. Advantageously, the photorecording material of the present disclosure exhibits a $\Delta n$ of $3\times10^{-3}$ or higher.

In some embodiments, this contrast is at least partly due to monomer/oligomer diffusion to exposed regions. See, e.g., Colburn and Haines, "Volume Hologram Formation in Photopolymer Materials," Appl. Opt. 10, 1636-1641, 1971; Lesnichii et al., "Study of diffusion in bulk polymer films below glass transition: evidences of dynamical heterogeneities," J. Phys.: Conf. Ser. 1062 012020, 2018. High index contrast is generally desired because it provides improved signal strength when reading a hologram, and provides efficient confinement of an optical wave in a waveguide. In some embodiments, one way to provide high index contrast in the present disclosure is to use a photoactive monomer/oligomer having moieties, referred to for example as index-contrasting moieties, that are substantially absent from the support matrix, and that exhibit a refractive index substantially different from the index exhibited by the bulk of the support matrix. In some embodiments, high contrast may be obtained by using a support matrix that contains primarily aliphatic or saturated alicyclic moieties with a low concentration of heavy atoms and conjugated double bonds providing low index, and a photoactive monomer/oligomer made up primarily of aromatic or similar high-index moieties.

As described herein, a holographic recording medium is formed such that holographic writing and reading to the medium are possible. Typically, fabrication of the medium involves depositing a combination, blend, mixture, etc., of the support matrix/polymerizable component/photoinitiator component, as well as any composition, compound, molecule, etc., used to control or substantially reduce the rate of polymerization in the absence of a photoinitiating light source (e.g., polymerization retarder), between two plates using, for example, a gasket to contain the mixture. The plates are typically glass, but it is also possible to use other materials transparent to the radiation used to write data, e.g., a plastic such as polycarbonate or poly(methyl methacrylate). It is possible to use spacers between the plates to maintain a desired thickness for the recording medium. In applications requiring optical flatness, the liquid mixture may shrink during cooling (if a thermoplastic) or curing (if a thermoset) and thus distort the optical flatness of the article. To reduce such effects, it is useful to place the article between plates in an apparatus containing mounts, e.g., vacuum chucks, capable of being adjusted in response to changes in parallelism and/or spacing. In such an apparatus, it is possible to monitor the parallelism in real-time by use of conventional interferometric methods, and to make any necessary adjustments to the heating/cooling process. In some embodiments, an article or substrate of the present disclosure may have an antireflective coating and/or be edge sealed to exclude water and/or oxygen. An antireflective coating may be deposited on an article or substrate by various processes such as chemical vapor deposition and an article or substrate may be edge sealed using known methods. In some embodiments, the photorecording material is also capable of being supported in other ways. More conventional polymer processing can also be used, e.g., closed mold formation or sheet extrusion. A stratified medium can also be used, e.g., a medium containing multiple substrates, e.g., glass, with layers of photorecording material disposed between the substrates.

In some embodiments, a holographic film described herein is a film composite consisting of one or more substrate films, one or more photopolymer films and one or more protective films in any desired arrangement. In some embodiments, materials or material composites of the substrate layer are based on polycarbonate (PC), polyethylene terephthalate (PET), polybutylene terephthalate, polyethylene, polypropylene, cellulose acetate, cellulose hydrate, cellulose nitrate, cycloolefin polymers, polystyrene, polyepoxides, polysulphone, cellulose triacetate (CTA), polyamide, polymethyl methacrylate, polyvinyl chloride, polyvinyl butyral or polydicyclopentadiene or mixtures thereof. In addition, material composites, such as film laminates or coextrudates, can be used as substrate film. Examples of material composites are duplex and triplex films having a structure according to one of the schemes A/B, A/B/A or A/B/C, such as PC/PET, PET/PC/PET and PC/TPU (TPU=thermoplastic polyurethane). In some embodiments, PC and PET are used as substrate film. Transparent substrate films which are optically clear, e.g. not hazy, can be used in some embodiments. The haze is measurable via the haze value, which is less than 3.5%, or less than 1%, or less than 0.3%. The haze value describes the fraction of transmitted light which is scattered in a forward direction by the sample through which radiation has passed. Thus, it is a measure of the opacity or haze of transparent materials and quantifies material defects, particles, inhomogeneities or crystalline phase boundaries in the material or its surface that interfere with the transparency. The method for measuring the haze is described in the standard ASTM D 1003.

In some embodiments, the substrate film has an optical retardation that is not too high, e.g. a mean optical retardation of less than 1000 nm, or of less than 700 nm, or of less than 300 nm. The automatic and objective measurement of the optical retardation is effected using an imaging polarimeter. The optical retardation is measured in perpendicular incidence. The retardation values stated for the substrate film are lateral mean values.

In some embodiments, the substrate film, including possible coatings on one or both sides, has a thickness of 5 to 2000 µm, or of 8 to 300 µm, or of 30 to 200, or of 125 to 175 µm, or of 30 to 45 µm.

In some embodiments, the film composite can have one or more covering layers on the photopolymer layer in order to protect it from dirt and environmental influences. Plastics films or film composite systems, but also clearcoats can be used for this purpose. In some embodiments, covering layers are film materials analogous to the materials used in the substrate film, having a thickness of 5 to 200 µm, or of 8 to 125 µm, or of 20 to 50 µm. In some embodiments, covering layers having as smooth a surface as possible are preferred. The roughness can be determined according to DIN EN ISO 4288. In some embodiments, roughness is in the region of less than or equal to 2 µm, or less than or equal to 0.5 µm. In some embodiments, PE or PET films having a thickness of 20 to 60 µm cam be used as laminating films. In some embodiments, a polyethylene film of 40 µm thickness can be used. In some embodiments, further protective layers, for example a backing of the substrate film, may be used.

In some embodiments, an article described herein can exhibit thermoplastic properties, and can heated above its melting temperature and processed in ways described herein for the combination, blend, mixture, etc., of the support matrix/polymerizable component/photoinitiator component/polymerization retarder.

Examples of other optical articles include beam filters, beam steerers or deflectors, and optical couplers. See, e.g., Solymar and Cooke, "Volume Holography and Volume Gratings," Academic Press, 315-327, 1981, incorporated herein by reference. A beam filter separates part of an incident laser beam that is traveling along a particular angle from the rest of the beam. Specifically, the Bragg selectivity of a thick transmission hologram is able to selectively diffract light along a particular angle of incidence, while light along other angles travels undeflected through the hologram. See, e.g., Ludman et al., "Very thick holographic nonspatial filtering of laser beams," Optical Engineering, Vol. 36, No. 6, 1700, 1997, incorporated herein by reference. A beam steerer is a hologram that deflects light incident at the Bragg angle. An optical coupler is typically a combination of beam deflectors that steer light from a source to a target. These articles, typically referred to as holographic optical elements, are fabricated by imaging a particular optical interference pattern within a recording medium, as discussed previously with respect to data storage. Media for these holographic optical elements are capable of being formed by the techniques discussed herein for recording media or waveguides.

Materials principles discussed herein are applicable not only to hologram formation, but also to formation of optical transmission devices such as waveguides. Polymeric optical waveguides are discussed for example in Booth, "Optical Interconnection Polymers," in Polymers for Lightwave and Integrated Optics, Technology and Applications, Hornak, ed., Marcel Dekker, Inc. (1992); U.S. Pat. No. 5,292,620 (Booth et al.), issued Mar. 18, 1994; and U.S. Pat. No. 5,219,710 (Horn et al.), issued Jun. 15, 1993, incorporated herein by reference. In some embodiments, a recording material described herein is irradiated in a desired waveguide pattern to provide refractive index contrast between the waveguide pattern and the surrounding (cladding) material. It is possible for exposure to be performed, for example, by a focused laser light or by use of a mask with a non-focused light source. Generally, a single layer is exposed in this manner to provide the waveguide pattern, and additional layers are added to complete the cladding, thereby completing the waveguide.

In one embodiment of the present disclosure, using conventional molding techniques, it is possible to mold the combination, blend, mixture, etc., of the support matrix/polymerizable component/photoinitiator component/polymerization retarder thus realizing a variety of shapes prior to formation of the article by cooling to room temperature. For example, the combination, blend, mixture, etc., of the support matrix/polymerizable component/photoinitiator component/polymerization retarder can be molded into ridge waveguides, where a plurality of refractive index patterns are then written into the molded structures. It is thereby possible to easily form structures such as Bragg gratings. This feature of the present disclosure increases the breadth of applications in which such polymeric waveguides would be useful.

Two-Stage Photopolymers

The purpose of a photopolymer is to faithfully record both phase and amplitude of a three-dimensional optical pattern. During the exposure process, the optical pattern is recorded as modulations in refractive index inside of the photopolymer film. Light is converted to variations in refractive index by a photopolymerization reaction, which causes high and low-index species to diffuse to bright and dark fringes, respectively.

Figure 3C:
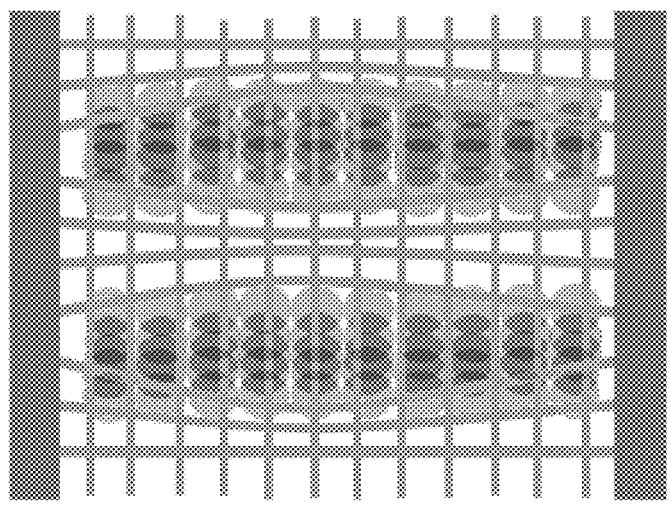
FIGS. 3A-3C illustrate generally the concept of using a two-stage photopolymer recording material for volume Bragg gratings, the material including a polymeric matrix (crosslinked lines), and recording, photopolymerizable monomers (circles). As the material is exposed to a light source (arrows, FIG. 3A), the monomer begins to react and polymerize. Ideally, polymerization occurs only in the light exposed areas, leading to a drop in monomer concentration. As the monomer polymerizes, a gradient of monomer concentration is created, resulting in monomer diffusing from high monomer concentration areas, toward low monomer concentration areas (FIG. 3B). As monomer diffuses into exposed regions, stress builds up in the surrounding matrix polymer as it swells and "diffuses" to the dark region (FIG. 3C). If the matrix becomes too stressed and cannot swell to accommodate more monomer, diffusion to exposed areas will stop, even if there is a concentration gradient for unreacted monomer. This typically limits the maximum dynamic range of the photopolymer, since the buildup of Δn depends on unreacted monomer diffusing into bright regions.
Figure 3B:
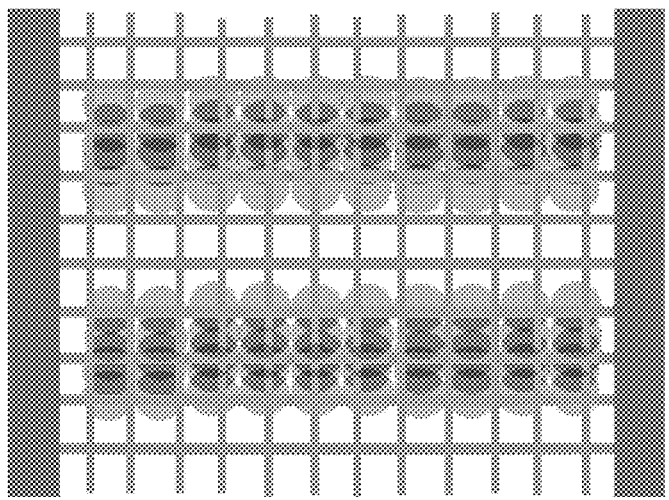
Figure 3A:
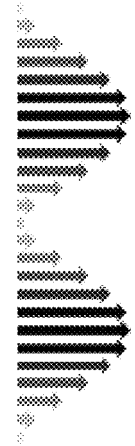
Figure 3A:
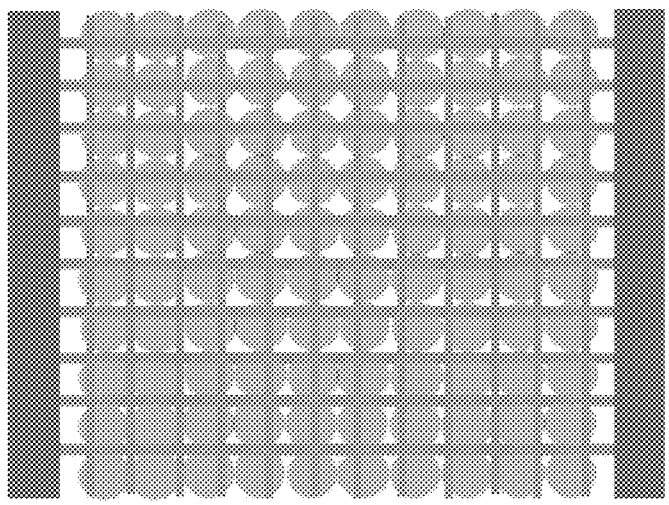

A two-stage photopolymer refers to a material that is "cured" twice (FIGS. 3A-3C). It typically consists of (at least) three materials: i) the matrix: typically a low refractive index rubbery polymer (like a polyurethane) that is thermally cured (1st stage) to provide mechanical support during the holographic exposure and ensure the refractive index modulation is permanently preserved; ii) the writing monomer: typically a high index acrylate monomer that reacts with a photoinitiator and polymerizes quickly; and iii) the photoinitiator (PI) system: the compound or group of compounds that react with light and initiate the polymerization of the writing monomer. For visible light polymerization, the PI system usually consists of two compounds that work together. The "dye" or "sensitizer" absorbs light and transfers energy or some reactive species to the "coinitiator," which actually initiates the polymerization reaction.

The performance of a holographic photopolymer is determined strongly by how species diffuse during polymerization. Usually, polymerization & diffusion are occurring simultaneously in a relatively uncontrolled fashion within the exposed areas. This leads to several undesirable effects. Polymers that are not bound to the matrix after initiation or termination reactions are free to diffuse out of exposed regions of the film into unexposed areas. This "blurs" the resulting fringes, reducing $\Delta n$ and diffraction efficiency of the final hologram. The buildup of $\Delta n$ during exposure means that subsequent exposures can scatter light from these gratings, leading to the formation of noise gratings. These create haze and a loss of clarity in the final waveguide display. For a series of multiplexed exposures with constant dose/exposure, the first exposures will consume most of the monomer, leading to an exponential decrease in diffraction efficiency with each exposure. A complicated "dose scheduling" procedure is required to balance the diffraction efficiency of all of the holograms.

Figure 2:
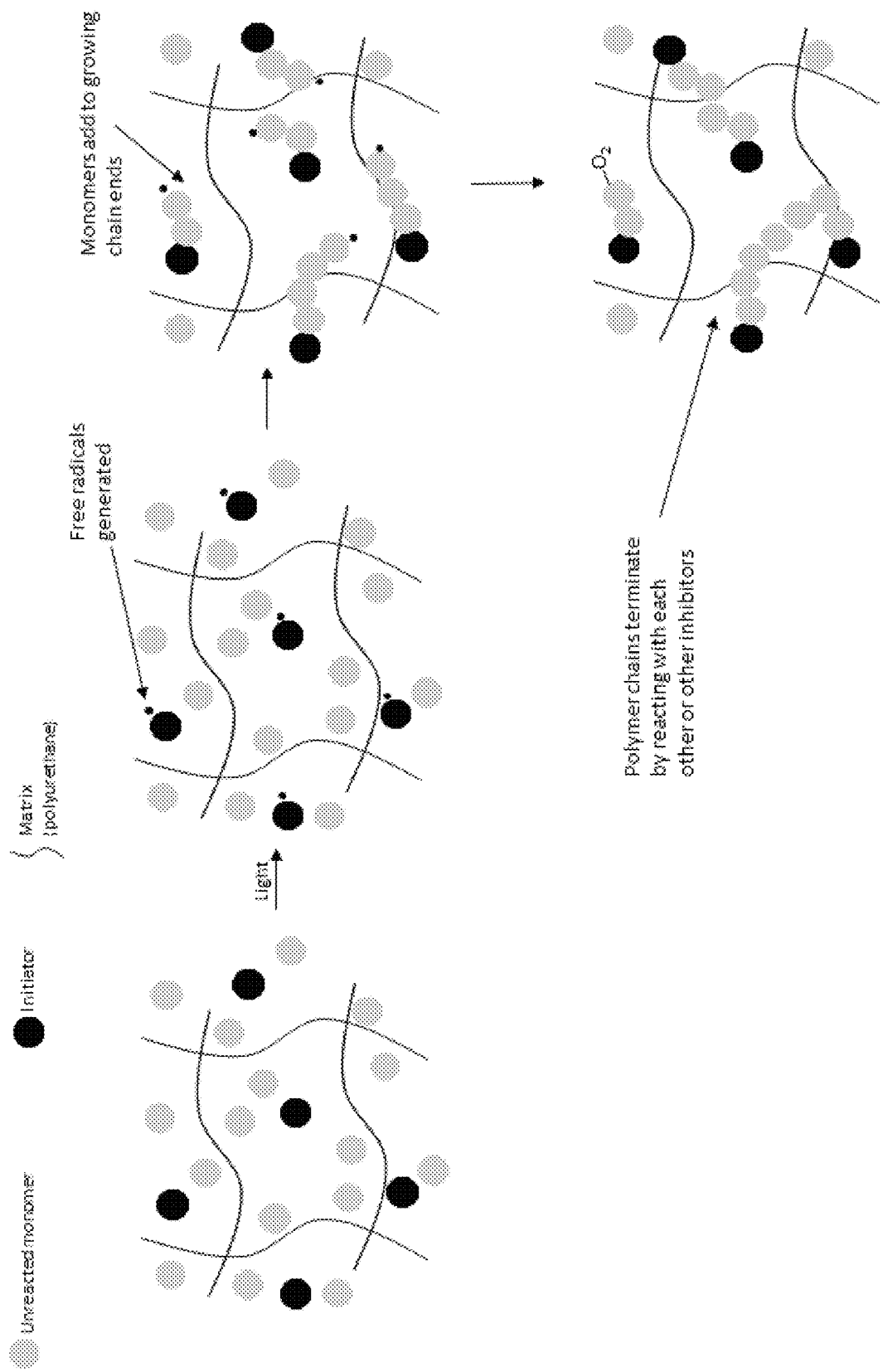
FIG. 2 is a schematic illustrating the various steps included in a controlled radical polymerization for holography applications. The general goals for such applications is the design of a photopolymer material that is sensitive to visible light, produces a large Δn response, and controls the reaction/diffusion of the photopolymer such that chain transfer and termination reactions are reduced or suppressed. The polymerization reaction that occurs inside traditional photopolymer materials is known as a free radical polymerization, which has several characteristics: radical species are produced immediately upon exposure, radicals initiate polymerization and propagate by adding monomer to chain ends, radicals also react with matrix by hydrogen abstraction and chain transfer reactions, and radicals can terminate by combining with other radicals or reacting with inhibiting species (e.g., $O_2$).

As shown in FIG. 2, controlled radical polymerization can be used in holography applications. The general goals for such applications is the design of a photopolymer material that is sensitive to visible light, produces a large $\Delta n$ response, and controls the reaction/diffusion of the photopolymer such that chain transfer and termination reactions are reduced or suppressed. The polymerization reaction that occurs inside traditional photopolymer materials is known as a free radical polymerization, which has several characteristics: radical species are produced immediately upon exposure, radicals initiate polymerization and propagate by adding monomer to chain ends, radicals also react with matrix by hydrogen abstraction and chain transfer reactions, and radicals can terminate by combining with other radicals or reacting with inhibiting species (e.g., $O_2$). Controlled radical polymerization that can be used include Atom Transfer Radical Polymerization (ATRP), Reversible Addition-Fragmentation Chain Transfer Polymerization (RAFT), and Nitroxide-mediated Polymerization (NMP).

The matrix is a solid polymer formed in situ from a matrix precursor by a curing step (curing indicating a step of inducing reaction of the precursor to form the polymeric matrix). It is possible for the precursor to be one or more monomers, one or more oligomers, or a mixture of monomer and oligomer. In addition, it is possible for there to be greater than one type of precursor functional group, either on a single precursor molecule or in a group of precursor molecules. Precursor functional groups are the group or groups on a precursor molecule that are the reaction sites for polymerization during matrix cure. To promote mixing with the photoactive monomer, in some embodiments the precursor is liquid at some temperature between about −50° C. and about 80° C. In some embodiments, the matrix polymerization is capable of being performed at room temperature. In some embodiments, the polymerization is capable of being performed in a time period less than 300 minutes, for example between about 5 and about 200 minutes. In some embodiments, the glass transition temperature ($T_g$) of the photorecording material is low enough to permit sufficient diffusion and chemical reaction of the photoactive monomer during a holographic recording process. Generally, the $T_g$ is not more than 50° C. above the temperature at which holographic recording is performed, which, for typical holographic recording, means a $T_g$ between about 80° C. and about −130° C. (as measured by conventional methods). In some embodiments, the matrix exhibits a three-dimensional network structure, as opposed to a linear structure, to provide the desired modulus described herein.

In some embodiments, use of a matrix precursor, e.g., the one or more compounds from which the matrix is formed, and a photoactive monomer that polymerize by independent reactions, substantially prevents both cross-reaction between the photoactive monomer and the matrix precursor during the cure, and inhibition of subsequent monomer polymerization. Use of a matrix precursor and photoactive monomer that form compatible polymers substantially avoids phase separation, and in situ formation allows fabrication of media with desirable thicknesses. These material properties are also useful for forming a variety of optical articles (optical articles being articles that rely on the formation of refractive index patterns or modulations in the refractive index to control or modify light that is directed at them). In addition to recording media, such articles include, but are not limited to, optical waveguides, beam steerers, and optical filters.

In some embodiments, independent reactions indicate: (a) the reactions proceed by different types of reaction intermediates, e.g., ionic vs. free radical, (b) neither the intermediate nor the conditions by which the matrix is polymerized will induce substantial polymerization of the photoactive monomer functional groups, e.g., the group or groups on a photoactive monomer that are the reaction sites for polymerization during the pattern (e.g., hologram) writing process (substantial polymerization indicates polymerization of more than 20% of the monomer functional groups), and (c) neither the intermediate nor the conditions by which the matrix is polymerized will induce a non-polymerization reaction of the monomer functional groups that either causes cross-reaction between monomer functional groups and the matrix or inhibits later polymerization of the monomer functional groups.

In some embodiments, polymers are considered to be compatible if a blend of the polymers is characterized, in 90° light scattering of a wavelength used for hologram formation, by a Rayleigh ratio ($R_{90}°$) less than $7\times10^{-3}$ cm$^{-1}$. The Rayleigh ratio ($R_\theta$) is a conventionally known property, and is defined as the energy scattered by a unit volume in the direction θ, per steradian, when a medium is illuminated with a unit intensity of unpolarized light, as discussed in Kerker, "The Scattering of Light and Other Electromagnetic Radiation," Academic Press, San Diego, 1969, at 38. The light source used for the measurement is generally a laser having a wavelength in the visible part of the spectrum. Normally, the wavelength intended for use in writing holograms is used. The scattering measurements are made upon a photorecording material that has been flood exposed. The scattered light is collected at an angle of 90° from the incident light, typically by a photodetector. It is possible to place a narrowband filter, centered at the laser wavelength, in front of such a photodetector to block fluorescent light, although such a step is not required. The Rayleigh ratio is typically obtained by comparison to the energy scatter of a reference material having a known Rayleigh ratio. Polymers considered miscible, e.g., according to conventional tests such as exhibition of a single glass transition temperature, will typically be compatible as well. But polymers that are compatible will not necessarily be miscible. In situ indicates that the matrix is cured in the presence of the photoimageable system. A useful photorecording material, e.g., the matrix material plus the photoactive monomer, photoinitiator, and/or other additives, is attained, the material capable of being formed in thicknesses greater than 200 μm, in some embodiments greater than 500 μm, and, upon flood exposure, exhibiting light scattering properties such that the Rayleigh ratio, $R_{90}$, is less than $7\times10^{-3}$ cm$^{-1}$. In some embodiments, flood exposure is exposure of the entire photorecording material by incoherent light at wavelengths suitable to induce substantially complete polymerization of the photoactive monomer throughout the material.

Polymer blends considered miscible, e.g., according to conventional tests such as exhibition of a single glass transition temperature, will also typically be compatible, e.g., miscibility is a subset of compatibility. Standard miscibility guidelines and tables are therefore useful in selecting a compatible blend. However, it is possible for polymer blends that are immiscible to be compatible according to the light scattering described herein.

A polymer blend is generally considered miscible if the blend exhibits a single glass transition temperature, $T_g$, as measured by conventional methods. An immiscible blend will typically exhibit two glass transition temperatures corresponding to the $T_g$ values of the individual polymers. $T_g$ testing is most commonly performed by differential scanning calorimetry (DSC), which shows the $T_g$ as a step change in the heat flow (typically the ordinate). The reported $T_g$ is typically the temperature at which the ordinate reaches the mid-point between extrapolated baselines before and after the transition. It is also possible to use Dynamic Mechanical Analysis (DMA) to measure $T_g$. DMA measures the storage modulus of a material, which drops several orders of magnitude in the glass transition region. It is possible in certain cases for the polymers of a blend to have individual $T_g$ values that are close to each other. In such cases, conventional methods for resolving such overlapping $T_g$ should be used, such as discussed in Brinke et al., "The thermal characterization of multi-component systems by enthalpy relaxation," Thermochimica Acta., 238, 75, 1994.

Matrix polymer and photopolymer that exhibit miscibility are capable of being selected in several ways. For example, several published compilations of miscible polymers are available, such as Olabisi et al., "Polymer-Polymer Miscibility," Academic Press, New York, 1979; Robeson, M M I. Press Symp. Ser., 2, 177, 1982; Utracki, "Polymer Alloys and Blends: Thermodynamics and Rheology," Hanser Publishers, Munich, 1989; and S. Krause in Polymer Handbook, J. Brandrup and E. H. Immergut, Eds.; 3rd Ed., Wiley Interscience, New York, 1989, pp. VI 347-370, incorporated herein by reference. Even if a particular polymer of interest is not found in such references, the approach specified allows determination of a compatible photorecording material by employing a control sample.

Determination of miscible or compatible blends is further aided by intermolecular interaction considerations that typically drive miscibility. For example, polystyrene and poly (methylvinylether) are miscible because of an attractive interaction between the methyl ether group and the phenyl ring. It is therefore possible to promote miscibility, or at least compatibility, of two polymers by using a methyl ether group in one polymer and a phenyl group in the other polymer. Immiscible polymers are also capable of being made miscible by the incorporation of appropriate functional groups that can provide ionic interactions. See Zhou and Eisenberg, J. Polym. Sci., Polym. Phys. Ed., 21 (4), 595, 1983; Murali and Eisenberg, J. Polym. Sci., Part B: Polym. Phys., 26 (7), 1385, 1988; and Natansohn et al., Makromol. Chem., Macromol. Symp., 16, 175, 1988. For example, polyisoprene and polystyrene are immiscible. However, when polyisoprene is partially sulfonated (5%), and 4-vinyl pyridine is copolymerized with the polystyrene, the blend of these two functionalized polymers is miscible. Without wishing to be bound by any particular theory, it is contemplated that the ionic interaction between the sulfonated groups and the pyridine group (proton transfer) is the driving force that makes this blend miscible. Similarly, polystyrene and poly(ethyl acrylate), which are normally immiscible, have been made miscible by lightly sulfonating the polystyrene. See Taylor-Smith and Register, Macromolecules, 26, 2802, 1993. Charge-transfer has also been used to make miscible polymers that are otherwise immiscible. For example it has been demonstrated that, although poly(methyl acrylate) and poly(methyl methacrylate) are immiscible, blends in which the former is copolymerized with (N-ethylcarbazol-3-yl)methyl acrylate (electron donor) and the latter is copolymerized with 2-[(3,5-dinitrobenzoyl)oxy] ethyl methacrylate (electron acceptor) are miscible, provided the right amounts of donor and acceptor are used. See Piton and Natansohn, Macromolecules, 28, 15, 1995. Poly (methyl methacrylate) and polystyrene are also capable of being made miscible using the corresponding donor-acceptor co-monomers. See Piton and Natansohn, Macromolecules, 28, 1605, 1995.

A variety of test methods exist for evaluating the miscibility or compatibility of polymers, as reflected in the recent overview published in Hale and Bair, Ch. 4—"Polymer Blends and Block Copolymers," Thermal Characterization of Polymeric Materials, 2nd Ed., Academic Press, 1997. For example, in the realm of optical methods, opacity typically indicates a two-phase material, whereas clarity generally indicates a compatible system. Other methods for evaluating miscibility include neutron scattering, infrared spectroscopy (IR), nuclear magnetic resonance (NMR), x-ray scattering and diffraction, fluorescence, Brillouin scattering, melt titration, calorimetry, and chemilluminescence. See, generally, Robeson, herein; Krause, Chemtracts-Macromol. Chem., 2, 367, 1991; Vesely in Polymer Blends and Alloys, Folkes and Hope, Eds., Blackie Academic and Professional, Glasgow, pp. 103-125; Coleman et al. Specific Interactions and the Miscibility of Polymer Blends, Technomic Publishing, Lancaster, Pa., 1991; Garton, Infrared Spectroscopy of Polymer Blends Composites and Surfaces, Hanser, N.Y., 1992; Kelts et al., Macromolecules, 26, 2941, 1993; White and Mirau, Macromolecules, 26, 3049, 1993; White and Mirau, Macromolecules, 27, 1648, 1994; and Cruz et al., Macromolecules, 12, 726, 1979; Landry et al., Macromolecules, 26, 35, 1993.

In some embodiments, compatibility has also been promoted in otherwise incompatible polymers by incorporating reactive groups into the polymer matrix, where such groups are capable of reacting with the photoactive monomer during the holographic recording step. Some of the photoactive monomer will thereby be grafted onto the matrix during recording. If there are enough of these grafts, it is possible to prevent or reduce phase separation during recording. However, if the refractive index of the grafted moiety and of the monomer are relatively similar, too many grafts, e.g., more than 30% of monomers grafted to the matrix, will tend to undesirably reduce refractive index contrast.

The optical article of the present disclosure is formed by steps including mixing a matrix precursor and a photoactive monomer, and curing the mixture to form the matrix in situ. In some embodiments, the reaction by which the matrix precursor is polymerized during the cure is independent from the reaction by which the photoactive monomer is later polymerized during writing of a pattern, e.g., data or waveguide form, and, in addition, the matrix polymer and the polymer resulting from polymerization of the photoactive monomer, e.g., the photopolymer, are compatible with each other. The matrix is considered to be formed when the photorecording material exhibits an elastic modulus of at least about $10^5$ Pa. In some embodiments, the matrix is considered to be formed when the photorecording material, e.g., the matrix material plus the photoactive monomer, photoinitiator, and/or other additives, exhibits an elastic modulus of at least about $10^5$ Pa. In some embodiments, the matrix is considered to be formed when the photorecording material, e.g., the matrix material plus the photoactive monomer, photoinitiator, and/or other additives, exhibits an elastic modulus of about $10^5$ Pa to about $10^9$ Pa. In some embodiments, the matrix is considered to be formed when the photorecording material, e.g., the matrix material plus the photoactive monomer, photoinitiator, and/or other additives, exhibits an elastic modulus of about $10^6$ Pa to about $10^8$ Pa.

In some embodiments, an optical article described herein contains a three-dimensional crosslinked polymer matrix and one or more photoactive monomers. At least one photoactive monomer contains one or more moieties, excluding the monomer functional groups, that are substantially absent from the polymer matrix. Substantially absent indicates that it is possible to find a moiety in the photoactive monomer such that no more than 20% of all such moieties in the photorecording material are present, e.g., covalently bonded, in the matrix. The resulting independence between the host matrix and the monomer offers useful recording properties in holographic media and desirable properties in waveguides such as enabling formation of large modulations in the refractive index without the need for high concentrations of the photoactive monomer. Moreover, it is possible to form the material without solvent development.

In some embodiments, media that utilize a matrix precursor and photoactive monomer that polymerize by non-independent reactions can be used, resulting in substantial cross-reaction between the precursor and the photoactive monomer during the matrix cure (e.g., greater than 20% of the monomer is attached to the matrix after cure), or other reactions that inhibit polymerization of the photoactive monomer. Cross-reaction tends to reduce the refractive index contrast between the matrix and the photoactive monomer and is capable of affecting the subsequent polymerization of the photoactive monomer, and inhibition of monomer polymerization clearly affects the process of writing holograms. As for compatibility, previous work has been concerned with the compatibility of the photoactive monomer in a matrix polymer, not the compatibility of the resulting photopolymer in the matrix. Yet, where the photopolymer and matrix polymer are not compatible, phase separation typically occurs during hologram formation. It is possible for such phase separation to lead to increased light scattering, reflected in haziness or opacity, thereby degrading the quality of the medium, and the fidelity with which stored data is capable of being recovered.

In one embodiment, the support matrix is thermoplastic and allows an article described herein to behave as if the entire article was a thermoplastic. That is, the support matrix allows the article to be processed similar to the way that a thermoplastic is processed, e.g., molded into a shaped article, blown into a film, deposited in liquid form on a substrate, extruded, rolled, pressed, made into a sheet of material, etc. and then allowed to harden at room temperature to take on a stable shape or form. The support matrix may comprise one or more thermoplastics. Suitable thermoplastics include poly(methyl vinyl ether-alt-maleic anhydride), poly(vinyl acetate), poly(styrene), poly(propylene), poly(ethylene oxide), linear nylons, linear polyesters, linear polycarbonates, linear polyurethanes, poly(vinyl chloride), poly(vinyl alcohol-co-vinyl acetate), and the like. In some embodiments, polymerization reactions that can be used for forming matrix polymers include cationic epoxy polymerization, cationic vinyl ether polymerization, cationic alkenyl ether polymerization, cationic allene ether polymerization, cationic ketene acetal polymerization, epoxy-amine step polymerization, epoxy-mercaptan step polymerization, unsaturated ester-amine step polymerization (e.g., via Michael addition), unsaturated ester-mercaptan step polymerization (e.g., via Michael addition), vinyl-silicon hydride step polymerization (hydrosilylation), isocyanate-hydroxyl step polymerization (e.g., urethane formation), isocyanate-amine step polymerization (e.g., urea formation), and the like.

In some embodiments, the photopolymer formulations described herein include matrix polymers obtainable by reacting a polyisocyanate component with an isocyanate-reactive component. The isocyanate component preferably comprises polyisocyanates. Polyisocyanates that may be used are all compounds known per se to a person skilled in the art or mixtures thereof, that have on average two or more NCO functions per molecule. These may have an aromatic, araliphatic, aliphatic or cycloaliphatic basis. Monoisocyanates and/or polyisocyanates containing unsaturated groups may also be concomitantly used in minor amounts. In some embodiments, the isocyanate component includes one or more of butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis(4,4'-isocyanatocyclohexyl)methane and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluene diisocyanate, 1,5-naphthylene diisocyanate, 2,4'- or 4,4'-diphenylmethane diisocyanate and/or triphenylmethane 4,4',4''-triisocyanate are suitable. Use of derivatives of monomeric di- or triisocyanates having urethane, urea, carbodiimide, acylurea, isocyanurate, allophanate, biuret, oxadiazinetrione, uretdione and/or iminooxadiazinedione structures is also possible. In some embodiments, the use of polyisocyanates based on aliphatic and/or cycloaliphatic di- or triisocyanates is preferred. In some embodiments, the polyisocyanates are di- or oligomerized aliphatic and/or cycloaliphatic di- or triisocyanates. In some embodiments, isocyanurates, uretdiones and/or iminooxadiazinediones based on HDI and 1,8-diisocyanato-4-(isocyanatomethyl)octane or mixtures thereof are preferred.

In some embodiments, NCO-functional prepolymers having urethane, allophanate, biuret and/or amide groups can be used. Prepolymers can also be obtained in a manner known per se to the person skilled in the art by reacting monomeric, oligomeric or polyisocyanates with isocyanate-reactive compounds in suitable stoichiometry with optional use of catalysts and solvents. In some embodiments, suitable polyisocyanates are all aliphatic, cycloaliphatic, aromatic or araliphatic di- and triisocyanates known per se to the person skilled in the art, it being unimportant whether these were obtained by means of phosgenation or by phosgene-free processes. In addition, the higher molecular weight subsequent products of monomeric di- and/or triisocyanates having a urethane, urea, carbodiimide, acylurea, isocyanurate, allophanate, biuret, oxadiazinetrione, uretdione or iminooxadiazinedione structure, which are well known per se to a person skilled in the art, can also be used, in each case individually or in any desired mixtures with one another. Examples of suitable monomeric di- or triisocyanates which can be used are butylene diisocyanate, hexamethylene diisocyanate (HDI), isophorone diisocyanate (IPDI), trimethylhexamethylene diisocyanate (TMDI), 1,8-diisocyanato-4-(isocyanatomethyl)octane, isocyanatomethyl-1,8-octane diisocyanate (TIN), 2,4- and/or 2,6-toluene diisocyanate.

OH-functional compounds are preferably used as isocyanate-reactive compounds for synthesizing the prepolymers. Said compounds are analogous to other OH-functional compounds described herein. In some embodiments, OH-functional compounds are polyester polyols and/or polyether polyols having number average molar masses of 200 to 6200 g/mol. Difunctional polyether polyols based on ethylene glycol and propylene glycol, the proportion of propylene glycol accounting for at least 40% by weight, and polymers of tetrahydrofuran having number average molar masses of 200 to 4100 g/mol and aliphatic polyester polyols having number average molar masses of 200 to 3100 g/mol can be used. Difunctional polyether polyols based on ethylene glycol and propylene glycol, the proportion of propylene glycol accounting for at least 80% by weight (in particular pure polypropylene glycols), and polymers of tetrahydrofuran having number average molar masses of 200 to 2100 g/mol can be used in some embodiments. Adducts of butyrolactone, ε-caprolactone and/or methyl-ε-caprolactone (in particular ε-caprolactone) with aliphatic, araliphatic or cycloaliphatic di-, tri- or polyfunctional alcohols containing 2 to 20 carbon atoms (in particular difunctional aliphatic alcohols having 3 to 12 carbon atoms) can be used in some embodiments. In some embodiments, these adducts have number average molar masses of 200 to 2000 g/mol, or of 500 to 1400 g/mol.

Allophanates may also be used as a mixture with other prepolymers or oligomers. In these cases, the use of OH-functional compounds having functionalities of 1 to 3.1 is advantageous. When monofunctional alcohols are used, those having 3 to 20 carbon atoms are preferred.

It is also possible to use amines for the prepolymer preparation. For example, ethylenediamine, diethylenetriamine, triethylenetetramine, propylenediamine, diaminocyclohexane, diaminobenzene, diaminobisphenyl, difunctional polyamines, for example, the Jeffamines®, amine-terminated polymers having number average molar masses of up to 10 000 g/mol or any desired mixtures thereof with one another are suitable.

For the preparation of prepolymers containing biuret groups, an excess of isocyanate is reacted with amine, a biuret group forming. In this case, suitable amines for the reaction with the di-, tri- and polyisocyanates mentioned are all oligomeric or polymeric, primary or secondary, difunctional amines described herein. Aliphatic biurets based on aliphatic amines and aliphatic isocyanates can be used in some embodiments. Low molecular weight biurets having number average molar masses of less than 2000 g/mol, based on aliphatic diamines or difunctional polyamines and aliphatic diisocyanates, in particular HDI and TMDI, can be used in some embodiments.

In some embodiments, prepolymers are urethanes, allophanates or biurets obtained from aliphatic isocyanate-functional compounds and oligomeric or polymeric isocyanate-reactive compounds having number average molar masses of 200 to 10 000 g/mol; urethanes, allophanates or biurets obtained from aliphatic isocyanate-functional compounds and polyols having number average molar masses of 200 to 6200 g/mol or (poly)amines having number average molar masses of less than 3000 g/mol can be used in some embodiments, and allophanates obtained from HDI or TMDI and difunctional polyether polyols (in particular polypropylene glycols) having number average molar masses of 200 to 2100 g/mol, urethanes obtained from HDI or TMDI, based on adducts of butyrolactone, ε-caprolactone and/or methyl-ε-caprolactone (in particular ε-caprolactone) with aliphatic, araliphatic or cycloaliphatic di-, tri- or polyfunctional alcohols containing 2 to 20 carbon atoms (in particular with difunctional aliphatic alcohols having 3 to 12 carbon atoms), having number average molar masses of 500 to 3000 g/mol, particularly preferably of 1000 to 2000 g/mol (in particular as a mixture with other oligomers of difunctional aliphatic isocyanates) or urethanes obtained from HDI or TMDI, based on trifunctional polyether polyols (in particular polypropylene glycol) having number average molar masses between 2000 and 6200 g/mol and biurets obtained from HDI or TMDI with difunctional amines or polyamines having number average molar masses of 200 to 1400 g/mol (in particular also as a mixture with other oligomers of difunctional aliphatic isocyanates) can be used in some embodiments. In some embodiments, the prepolymers described herein have residue contents of free monomeric isocyanate of less than 2% by weight, or less than 1.0% by weight, or less than 0.5% by weight.

In some embodiments, the isocyanate component contains proportionately further isocyanate components in addition to the prepolymers described. Aromatic, araliphatic, aliphatic and cycloaliphatic di-, tri- or polyisocyanates are suitable for this purpose used. It is also possible to use mixtures of such di-, tri- or polyisocyanates. Examples of suitable di-, tri- or polyisocyanates are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate (TMDI), the isomeric bis(4,4'-isocyanatocyclohexyl)methanes and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluene diisocyanate, 1,5-naphthylene diisocyanate, 2,4'- or 4,4'-diphenylmethane diisocyanate, triphenylmethane 4,4',4''-triisocyanate or derivatives thereof having a urethane, urea, carbodiimide, acylurea, isocyanurate, allophanate, biuret, oxadiazinetrione, uretdione, or iminooxadiazinedione structure and mixtures thereof. Polyisocyanates based on oligomerized and/or derivatized diisocyanates which were freed from excess diisocyanate by suitable processes are preferred, in particular those of hexamethylene diisocyanate. The oligomeric isocyanurates, uretdiones and iminooxadiazinediones of HDI and mixtures thereof can be used in some embodiments.

In some embodiments, it is optionally also possible for the isocyanate component proportionately to contain isocyanates that have been partly reacted with isocyanate-reactive ethylenically unsaturated compounds. α,β-Unsaturated carboxylic acid derivatives, such as acrylates, methacrylates, maleates, fumarates, maleimides, acrylamides and vinyl ethers, propenyl ethers, allyl ethers and compounds which contain dicyclopentadienyl units and have at least one group reactive towards isocyanates can be used in some embodiments as isocyanate-reactive ethylenically unsaturated compounds; acrylates and methacrylates having at least one isocyanate-reactive group can be used in some embodiments. Suitable hydroxy-functional acrylates or methacrylates are, for example, compounds such as 2-hydroxyethyl (meth)acrylate, polyethylene oxide mono(meth)acrylates, polypropylene oxide mono(meth)-acrylates, polyalkylene oxide mono(meth)acrylates, poly(ε-caprolactone)mono (meth)-acrylates, such as, for example, Tone® M100 (Dow, USA), 2-hydroxypropyl(meth)acrylate, 4-hydroxybutyl (meth)acrylate, 3-hydroxy-2,2-dimethylpropyl(meth)acrylate, the hydroxy-functional mono-, di- or tetra(meth)acrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol or the industrial mixtures thereof. In addition, isocyanate-reactive oligomeric or polymeric unsaturated compounds containing acrylate and/or methacrylate groups, alone or in combination with the abovementioned monomeric compounds, are suitable. The proportion of isocyanates which have been partly reacted with isocyanate-reactive ethylenically unsaturated compounds, based on the isocyanate component, is 0 to 99%, or 0 to 50%, or 0 to 25% or 0 to 15%.

In some embodiments, it is optionally also possible for the isocyanate component to contain, completely or proportionately, isocyanates which have been reacted completely or partly with blocking agents known to the person skilled in the art from coating technology. The following may be mentioned as an example of blocking agents: alcohols, lactams, oximes, malonic esters, alkyl acetoacetates, triazoles, phenols, imidazoles, pyrazoles and amines, such as, for example, butanone oxime, diisopropylamine, 1,2,4-triazole, dimethyl-1,2,4-triazole, imidazole, diethyl malonate, ethyl acetoacetate, acetone oxime, 3,5-dimethylpyrazole, ε-caprolactam, N-tert-butylbenzylamine, cyclopentanone carboxyethyl ester or any desired mixtures of these blocking agents.

Generally, all polyfunctional, isocyanate-reactive compounds which have on average at least 1.5 isocyanate-reactive groups per molecule can be used. Isocyanate-reactive groups in the context of the present disclosure are preferably hydroxy, amino or thio groups; hydroxy compounds can be used in some embodiments. Suitable polyfunctional, isocyanate-reactive compounds are, for example, polyester, polyether, polycarbonate, poly(meth) acrylate and/or polyurethane polyols. In some embodiments, aliphatic, araliphatic or cycloaliphatic di-, tri- or polyfunctional alcohols having low molecular weights, e.g. having molecular weights of less than 500 g/mol, and short chains, e.g. containing 2 to 20 carbon atoms, are also suitable as polyfunctional, isocyanate-reactive compounds. In some embodiments, these may be, for example, ethylene glycol, diethylene glycol, triethylene glycol, tetraethylene glycol, dipropylene glycol, tripropylene glycol, 1,2-propanediol, 1,3-propanediol, 1,4-butanediol, neopentyl glycol, 2-ethyl-2-butylpropanediol, trimethylpentanediol, positional isomers of diethyloctanediol, 1,3-butylene glycol, cyclohexanediol, 1,4-cyclohexanedimethanol, 1,6-hexanediol, 1,2- and 1,4-cyclohexanediol, hydrogenated bisphenol A (2,2-bis(4-hydroxycyclohexyl)propane), 2,2-dimethyl-3-hydroxy-propionic acid (2,2-dimethyl-3-hydroxypropyl ester). Examples of suitable triols are trimethylolethane, trimethylolpropane or glycerol. Suitable higher-functional alcohols are ditrimethylolpropane, pentaerythritol, dipentaerythritol or sorbitol. Suitable polyester polyols are, for example, linear polyester diols or branched polyester polyols, as are obtained in a known manner from aliphatic, cycloaliphatic or aromatic di- or polycarboxylic acids or their anhydrides with polyhydric alcohols having an OH functionality of ≥2. In some embodiments, di- or polycarboxylic acids or anhydrides are succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid and acid anhydrides such as o-phthalic, trimellitic or succinic anhydride or any desired mixtures thereof with one another. In some embodiments, suitable alcohols are ethanediol, di-, tri- and tetraethylene glycol, 1,2-propanediol, di-, tri- and tetrapropylene glycol, 1,3-propanediol, butanediol-1,4, butanediol-1,3, butanediol-2,3, pentanediol-1,5, hexanediol-1,6,2,2-dimethyl-1,3-propanediol, 1,4-dihydroxycyclohexane, 1,4-dimethylolcyclohexane, 1,8-octanediol, 1,10-decanediol, 1,12-dodecanediol, trimethylolpropane, glycerol or any desired mixtures thereof with one another. In some embodiments, polyester polyols are based on aliphatic alcohols and mixtures of aliphatic and aromatic acids and have number average molar masses between 500 and 10 000 g/mol and functionalities between 1.8 and 6.1. In some embodiments, polyester polyols are based on aliphatic diols, such as butane-1,4-diol, hexane-1,6-diol, neopentyl glycol, ethanediol, propylene glycol, 1,3-butylene glycol, di-, tri-, or polyethylene glycol, di-, tri- and/or tetrapropylene glycol or mixtures of the abovementioned diols with aliphatic higher-functional alcohols, such as trimethylolpropane and/or pentaerythritol, the proportion of the higher-functional alcohols preferably accounting for less than 50% by weight (particularly preferably less than 30% by weight), based on the total amount of the alcohol used, in combination with aliphatic di- or polycarboxylic acids or anhydrides such as adipic acid and/or succinic acid, or mixtures of the abovementioned aliphatic polycarboxylic acids or anhydrides with aromatic polycarboxylic acids or anhydrides, such as terephthalic acid and/or isophthalic acid, the proportion of the aromatic polycarboxylic acids or anhydrides preferably accounting for less than 50% by weight (and particularly preferably less than 30% by weight), based on the total amount of the polycarboxylic acids or anhydrides used. In some embodiments, polyester polyols have number average molar masses between 1000 and 6000 g/mol and functionalities between 1.9 and 3.3. Polyester polyols may also be based on natural raw materials, such as castor oil. It is also possible for the polyester polyols to be based on homo- or copolymers of lactones, as can preferably be obtained by an addition reaction of lactones or lactone mixtures in a ring-opening lactone polymerization, such as butyrolactone, ε-caprolactone and/or methyl-ε-caprolactone, with hydroxy-functional compounds, such as polyhydric alcohols having an OH functionality of ≥2 or polyols having a functionality of greater than 1.8, for example of the abovementioned type. In some embodiments, polyols which are used as starters here are polyether polyols having a functionality of 1.8 to 3.1 and number average molar masses of 200 to 4000 g/mol; poly (tetrahydrofurans) having a functionality of 1.9 to 2.2 and number average molar masses of 500 to 2000 g/mol (in particular 600 to 1400 g/mol) are particularly preferred. In some embodiments, adducts are butyrolactone, ε-caprolactone and/or methyl-ε-caprolactone, ε-caprolactone. In some embodiments, polyester polyols preferably have number average molar masses of 400 to 6000 g/mol, or of 800 to 3000 g/mol. In some embodiments, OH functionality is 1.8 to 3.5, or 1.9 to 2.2.

Suitable polycarbonate polyols are obtainable in a manner known per se by reaction of organic carbonates or phosgene with diols or diol mixtures. In some embodiments, organic carbonates are dimethyl, diethyl and diphenyl carbonate. In some embodiments, suitable diols or mixtures comprise the polyhydric alcohols mentioned in the context of the polyester segments and having an OH functionality of ≥2, preferably 1,4-butanediol, 1,6-hexanediol and/or 3-methylpentanediol, or polyester polyols can be converted into polycarbonate polyols. In some embodiments, such polycarbonate polyols have number average molar masses of 400 to 4000 g/mol, or of 500 to 2000 g/mol. In some embodiments, the OH functionality of these polyols is 1.8 to 3.2, or 1.9 to 3.0.

In some embodiments, suitable polyether polyols are polyadducts of cyclic ethers with OH- or NH-functional starter molecules, which polyadducts optionally have a block structure. Suitable cyclic ethers are, for example, styrene oxides, ethylene oxide, propylene oxide, tetrahydrofuran, butylene oxide, epichlorohydrin and any desired mixtures thereof. Starters which may be used are the polyhydric alcohols mentioned in the context of the polyester polyols and having an OH functionality of ≥2 and primary or secondary amines and amino alcohols. In some embodiments, polyether polyols are those of the abovementioned type, exclusively based on propylene oxide or random or block copolymers based on propylene oxide with further 1-alkylene oxides, the proportion of the 1-alkylene oxide not being higher than 80% by weight. Propylene oxide homopolymers and random or block copolymers which have oxyethylene, oxypropylene and/or oxybutylene units can be used in some embodiments, the proportion of the oxypropylene units, based on the total amount of all oxyethylene, oxypropylene and oxybutylene units, accounting for at least 20% by weight, preferably at least 45% by weight. Oxypropylene and oxybutylene comprise all respective linear and branched C3- and C4-isomers. In some embodiments, such polyether polyols have number average molar masses of 250 to 10 000 g/mol, or of 500 to 8500 g/mol, or of 600 to 4500 g/mol. In some embodiments, the OH functionality is 1.5 to 4.0, or 1.8 to 3.1, or 1.9 to 2.2.

In some embodiments, matrix forming reactions are enabled or accelerated by suitable catalysts. For example, cationic epoxy polymerization takes place rapidly at room temperature by use of $BF_3$-based catalysts, other cationic polymerizations proceed in the presence of protons, epoxymercaptan reactions and Michael additions are accelerated by bases such as amines, hydrosilylation proceeds rapidly in the presence of transition metal catalysts such as platinum, and urethane and urea formation proceed rapidly when tin catalysts are employed. It is also possible to use photogenerated catalysts for matrix formation, provided that steps are taken to prevent polymerization of the photoactive monomer during the photogeneration.

In some embodiments, the amount of thermoplastic used in a holographic recording medium described herein is enough that the entire holographic recording medium effectively acts as a thermoplastic for most processing purposes. In some embodiments, the binder component of the holographic recording medium may make up as much as about 5%, or as much as about 50%, or as much as about 90% of the holographic recording medium by weight. The amount of any given support matrix in the holographic recording medium may vary based on clarity, refractive index, melting temperature, $T_g$, color, birefringence, solubility, etc., of the thermoplastic or thermoplastics that make up the binder component. Additionally, the amount of the support matrix in the holographic recording medium may vary based on the article's final form, whether it is a solid, a flexible film, or an adhesive.

In one embodiment of the present disclosure, the support matrix includes a telechelic thermoplastic resin, e.g., the thermoplastic polymer may be functionalized with reactive groups that covalently crosslink the thermoplastic in the support matrix with the polymer formed from the polymerizable component during grating formation. Such crosslinking makes the gratings stored in the thermoplastic holographic recording medium very stable, even to elevated temperatures for extended periods of time.

In some embodiments where a thermoset is formed, the matrix may contain functional groups that copolymerize or otherwise covalently bond with the monomer used to form the photopolymer. Such matrix attachment methods allow for increased archival life of the recorded holograms. Suitable thermoset systems for used herein are disclosed in to U.S. Pat. No. 6,482,551 (Dhar et al.), incorporated herein by reference.

In some embodiments, the thermoplastic support matrix becomes crosslinked noncovalently with the polymer formed upon grating formation by using a functionalized thermoplastic polymer in the support matrix. Examples of such non-covalent bonding include ionic bonding, hydrogen bonding, dipole-dipole bonding, aromatic pi stacking, etc.

In some embodiments, the polymerizable component of an article of the present disclosure includes at least one photoactive polymerizable material that can form holographic gratings made of a polymer or co-polymer when exposed to a photoinitiating light source, such as a laser beam that is recording data pages to the holographic recording medium. The photoactive polymerizable materials can include any monomer, oligomer, etc., that is capable of undergoing photoinitiated polymerization, and which, in combination with the support matrix, meets the compatibility requirements of the present disclosure. Suitable photoactive polymerizable materials include those which polymerize by a free-radical reaction, e.g., molecules containing ethylenic unsaturation such as acrylates, methacrylates, acrylamides, methacrylamides, styrene, substituted styrenes, vinyl naphthalene, substituted vinyl naphthalenes, and other vinyl derivatives. Free-radical copolymerizable pair systems such as vinyl ether/maleimide, vinyl ether/thiol, acrylate/thiol, vinyl ether/hydroxy, etc., are also suitable. It is also possible to use cationically polymerizable systems; a few examples are vinyl ethers, alkenyl ethers, allene ethers, ketene acetals, epoxides, etc. Furthermore, anionic polymerizable systems are suitable. It is also possible for a single photoactive polymerizable molecule to contain more than one polymerizable functional group. Other suitable photoactive polymerizable materials include cyclic disulfides and cyclic esters. Oligomers that may be included in the polymerizable component to form a holographic grating upon exposure to a photoinitiating light source include oligomers such as oligomeric (ethylene sulfide) dithiol, oligomeric (phenylene sulfide) dithiol, oligomeric (bisphenol A), oligomeric (bisphenol A) diacrylate, oligomeric polyethylene with pendent vinyl ether groups, etc. The photoactive polymerizable material of the polymerizable component of an article of the present disclosure may be monofunctional, difunctional, and/or multifunctional.

In some embodiments, the polymerizable component can include various fluorene derivatized monomers. Fluorene monomers include basic structures, cardo structures, or spiro structures:

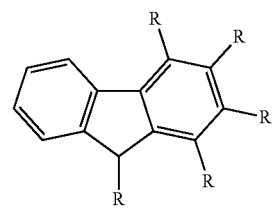

Basic Structure Fluorene

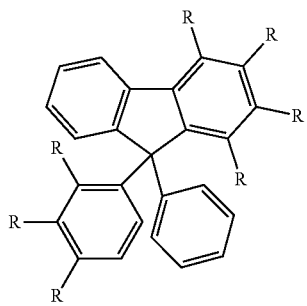

Cardo Structure Fluorene

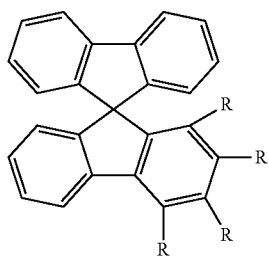

Spiro Structure Fluorene

Fluorene compounds have been described for example in "Poly(phenylene thioether)s with Fluorene-Based Cardo Structure toward High Transparency, High Refractive Index, and Low Birefringence," Macromolecules, 2016, 49 (16), pp 5849-5856.

In some embodiments, cardo structure have high refractive index due to additional phenyl rings, low birefringence due to twisted, offset orientation between the phenyl rings and the fluorene structure. Without wishing to be bound by any particular theory, it is believed that this leads to lower polarization anisotropy and a smaller difference between RIs in perpendicular and parallel orientation. Also without wishing to be bound by any particular theory, it is believed that twisted structure leads to high transparency due to reduced packing.

In some embodiments, substituents R for any of the basic, cardo, and/or spiro structure fluorenes can be, without limitation: high refractive index (RI) groups, including halogens (F, Cl, Br, I), sulfur-containing groups, such as thiols, thioethers, thioesters, thianthrenes, etc., phenyl groups (optionally further substituted with high RI groups described herein). In some embodiments, one or more of the R groups includes a polymerizable group, including, without limitation: olefinic groups, such as acrylates, methacrylates, styrenes, etc., cyclic structures, such as epoxides, lactones, carbonates, etc. In some embodiments, preference is given to those structures that contain some group capable of participating in hydrogen bonding, which improves compatibility with the surrounding matrix polymer. In some embodiments, the compounds described herein exclude a thioether group.

In some embodiments, the polymerizable component can include a compound of Formula I:

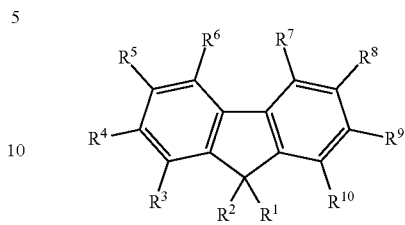

Formula I wherein in Formula I each $R^1$ to $R^{10}$ is independently hydrogen or a substituent including one or more groups selected from optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, hydroxy, halo, cyano, trifluoromethyl, trifluoromethoxy, nitro, trimethylsilanyl, optionally substituted epoxide, optionally substituted glycidyl, optionally substituted acrylate, optionally substituted methacrylate, —OR, —SR$^a$, —OC(O)—R$^a$, —N(R$^a$)$_2$, —C(O)R$^a$, —C(O)OR$^a$, —C(O)SR$^a$, —SC(O)R$^a$, —OC(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$, —S(O)$_t$OR$^a$, —S(O)$_t$N(R$^a$)$_2$, —S(O)$_t$N(R$^a$)C(O)R$^a$, —O(O)P(OR$^a$)$_2$, and —O(S)P(OR$^a$)$_2$; t is 1 or 2; each R$^a$ is independently selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, and optionally substituted heteroarylalkyl; and wherein at least one of $R^1$ to $R^{10}$ includes a polymerizable or crosslinkable group. In some embodiments, the compound has Formula I(a):

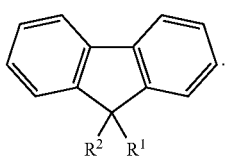

Formula I(a)

In some embodiments, the polymerizable component can include a compound of Formula I, or a compound of Formula I(a), wherein a substituent includes one or more linking groups selected from —C$_{1-10}$ alkyl-, —O—C$_{1-10}$ alkyl-, —C$_{1-10}$ alkenyl-, —O—C$_{1-10}$ alkenyl-, —C$_{1-10}$ cycloalkenyl-, —O—C$_{1-10}$ cycloalkenyl-, —C$_{1-10}$ alkynyl-, —O—C$_{1-10}$ alkynyl-, —C$_{1-10}$ aryl-, —O—C$_{1-10}$ aryl-, —O—, —S—, —C(O)—, —C(O)O—, —OC(O)—, —OC(O)O—, —N(R$^b$)—, —C(O)N(R$^b$)—, —N(R$^b$)C(O)—, —OC(O)N(R$^b$)—, —N(R$^b$)C(O)O—, —N(R$^b$)C(O)N(R$^b$)—, —N(R$^b$)C(NR$^b$)N(R$^b$), —N(R$^b$)S(O)$_w$—, —S(O)$_w$N(R$^b$)—, —S(O)$_w$O—, —OS(O)$_w$—, —OS(O)$_w$O—, —O(O)P(OR$^b$)O—, (O)P(O—)$_3$, —O(S)P(OR$^b$)O—, and (S)P(O—)$_3$, wherein w is 1 or 2, and R$^b$ is independently hydrogen, optionally substituted alkyl, or optionally substituted aryl. In some embodiments, the substituent includes one or more linking groups selected from —(CH₂)ₙ—, 1,2 disubstituted phenyl, 1,3 disubstituted phenyl, 1,4 disubstituted phenyl, —CH=CH—, —C≡C—, —O—, —S—, —C(O)—, —C(O)O—, —OC(O)—, —OC(O)O—, —NH—, —C(O)NH—, —NHC(O)—, —OC(O)NH—, —NHC(O)O—, —NHC(O)NH—, —NHC(NH)NH—, —NHS(O)₂—, —S(O)₂NH—, —S(O)₂O—, —OS(O)₂—, —OS(O)O—, (O)P(O—)₃, and (S)P(O—)₃, wherein n is an integer from 1 to 12. In some embodiments, the substituent includes one or more linking groups selected from —(CH₂)₂—, 1,4 disubstituted phenyl, —CH=CH—, —O—, —C(O)—, —C(O)O—, —OC(O)—, —NH—, —C(O)NH—, —NHC(O)—, —OC(O)NH—, —NHC(O)O—, and (S)P(O—)₃. In some embodiments, the substituent includes one or more terminal groups selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, optionally substituted acrylate, optionally substituted methacrylate, optionally substituted styrene, optionally substituted epoxide, optionally substituted lactone, optionally substituted carbonate, hydroxy, halo, cyano, trifluoromethyl, trifluoromethoxy, nitro, and trimethylsilanyl. In some embodiments, the substituent includes one or more terminal groups selected from alkenyl and cycloalkenyl. In some embodiments, the substituent includes one or more terminal groups selected from optionally substituted acrylate, optionally substituted methacrylate, optionally substituted vinyl, and optionally substituted allyl. In some embodiments, the substituent includes one or more terminal groups selected from acrylate and methacrylate. In some embodiments, the polymerizable or crosslinkable group is selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted lactone, and optionally substituted carbonate. In some embodiments, the polymerizable or crosslinkable group is selected from acrylate and methacrylate. In some embodiments, the substituent is selected from:

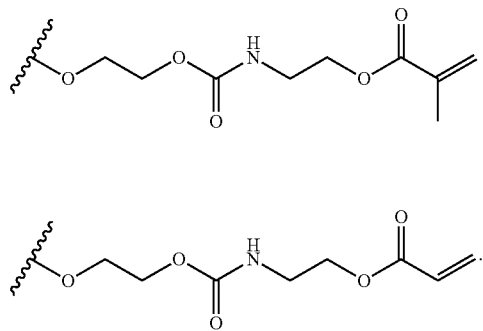

In some embodiments, the polymerizable component can include a compound of Formula II:

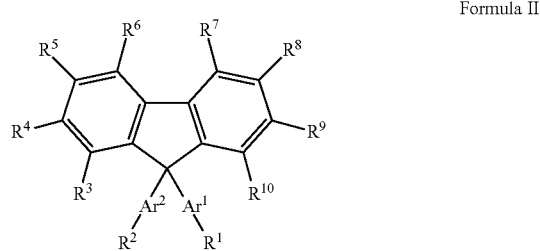

Formula II wherein in Formula II Ar¹ and Ar² are independently selected from a bond, optionally substituted alkyl, optionally substituted aryl, optionally substituted arylalkyl, optionally substituted heteroaryl, and optionally substituted heteroarylalkyl; each $R^1$ to $R^{10}$ is independently hydrogen or a substituent including one or more groups selected from optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, hydroxy, halo, cyano, trifluoromethyl, trifluoromethoxy, nitro, trimethylsilanyl, optionally substituted epoxide, optionally substituted glycidyl, optionally substituted acrylate, optionally substituted methacrylate, —OR$^a$, —SR$^a$, —OC(O)—R$^a$, —N(R$^a$)₂, —C(O)R$^a$, —C(O)OR$^a$, —C(O)SR$^a$, —SC(O)R$^a$, —OC(O)OR$^a$, —OC(O)N(R$^a$)₂, —C(O)N(R$^a$)₂, —N(R$^a$)C(O)OR$^a$, —N(R$^a$)C(O)R$^a$, —N(R$^a$)C(O)N(R$^a$)₂, N(R$^a$)C(NR$^a$)N(R$^a$)₂, —N(R$^a$)S(O)$_t$R$^a$, S(O)$_t$OR$^a$, —S(O)$_t$N(R$^a$)₂, —S(O)$_t$N(R$^a$)C(O)R$^a$, —O(O)P(OR$^a$)₂, and —O(S)P(OR$^a$)₂; t is 1 or 2; each R$^a$ is independently selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, and optionally substituted heteroarylalkyl; and wherein at least one of $R^1$ to $R^{10}$ includes a polymerizable or crosslinkable group. In some embodiments, the compound has Formula II(a) or Formula II(b):

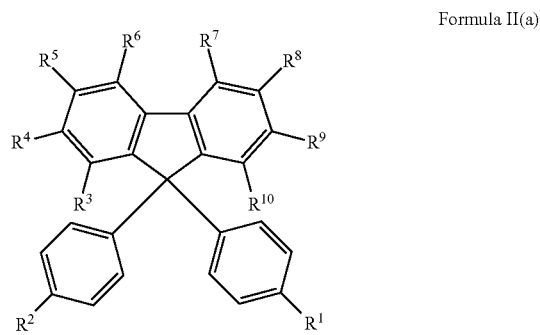

Formula II(a)

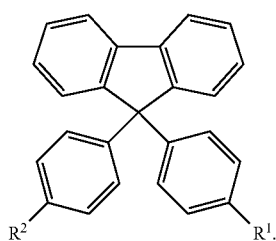

Formula II(b)

In some embodiments, the polymerizable component can include a compound of Formula II, Formula II(a), or Formula II(b), a substituent includes one or more linking groups selected from —C$_{1-10}$ alkyl-, —O—C$_{1-10}$ alkyl-, —C$_{1-10}$ alkenyl-, —O—C$_{1-10}$ alkenyl-, —C$_{1-10}$ cycloalkenyl-, —O—C$_{1-10}$ cycloalkenyl-, —C$_{1-10}$ alkynyl-, —O—C$_{1-10}$ alkynyl-, —C$_{1-10}$ aryl-, —O—C$_{1-10}$ aryl-, —O—, —S—, —C(O)—, —C(O)O—, —OC(O)—, —OC(O)O—, —N(R$^b$)—, —C(O)N(R$^b$)—, —N(R$^b$)C(O)—, —OC(O)N(R$^b$)—, —N(R$^b$)C(O)O—, —N(R$^b$)C(O)N(R$^b$)—, —N(R$^b$)C(NR$^b$)N(R$^b$), —N(R$^b$)S(O)$_w$—, —S(O)$_w$N(R$^b$)—, —S(O)$_w$O—, —OS(O)$_w$—, —OS(O)O$_w$—, —O(O)P(OR$^b$)O—, (O)P(O—)$_3$, —O(S)P(OR$^b$)O—, and (S)P(O—)$_3$, wherein w is 1 or 2, and R$^b$ is independently hydrogen, optionally substituted alkyl, or optionally substituted aryl. In some embodiments, the substituent includes one or more linking groups selected from —(CH$_2$)$_n$—, 1,2 disubstituted phenyl, 1,3 disubstituted phenyl, 1,4 disubstituted phenyl, —CH=CH—, —C≡C—, —O—, —S—, —C(O)—, —C(O)O—, —OC(O)—, —OC(O)O—, —NH—, —C(O)NH—, —NHC(O)—, —OC(O)NH—, —NHC(O)O—, —NHC(O)NH—, —NHC(NH)NH—, —NHS(O)$_2$—, —S(O)$_2$NH—, —S(O)$_2$O—, —OS(O)$_2$—, —OS(O)O—, (O)P(O—)$_3$, and (S)P(O—)$_3$, wherein n is an integer from 1 to 12. In some embodiments, the substituent includes one or more linking groups selected from —(CH$_2$)$_2$—, 1,4 disubstituted phenyl, —CH=CH—, —O—, —C(O)—, —C(O)O—, —OC(O)—, —NH—, —C(O)NH—, —NHC(O)—, —OC(O)NH—, —NHC(O)O—, and (S)P(O—)$_3$. In some embodiments, the substituent includes one or more terminal groups selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, optionally substituted acrylate, optionally substituted methacrylate, optionally substituted styrene, optionally substituted epoxide, optionally substituted lactone, optionally substituted carbonate, hydroxy, halo, cyano, trifluoromethyl, trifluoromethoxy, nitro, and trimethylsilanyl. In some embodiments, the substituent includes one or more terminal groups selected from alkenyl and cycloalkenyl. In some embodiments, the substituent includes one or more terminal groups selected from optionally substituted acrylate, optionally substituted methacrylate, optionally substituted vinyl, and optionally substituted allyl. In some embodiments, the substituent includes one or more terminal groups selected from acrylate and methacrylate. In some embodiments, the polymerizable or crosslinkable group is selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted lactone, and optionally substituted carbonate. In some embodiments, the polymerizable or crosslinkable group is selected from acrylate and methacrylate. In some embodiments, the substituent is selected from:

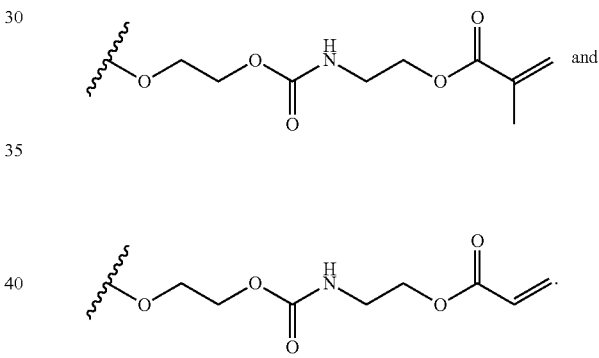

and

In some embodiments, the polymerizable component can include a compound of Formula II(c), Formula II(d), Formula II(e), Formula II(f), Formula II(g), Formula II(h), Formula II(i), or Formula II(j):

Formula II(c)

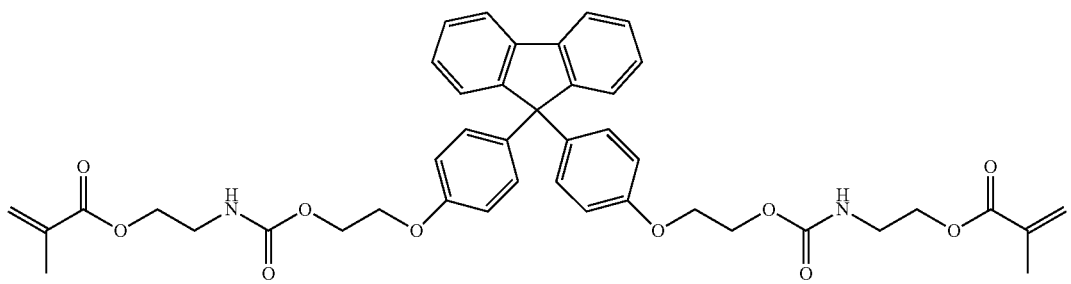

Formula II(d)
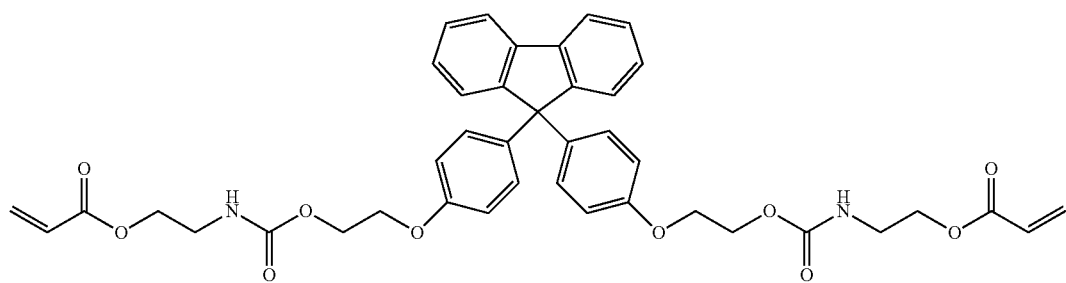
Formula II(e)
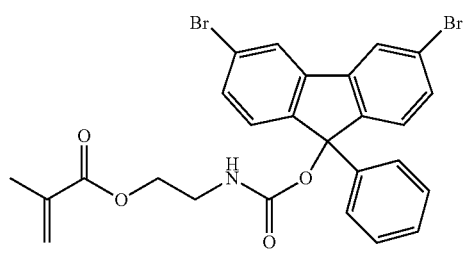
Formula II(f)
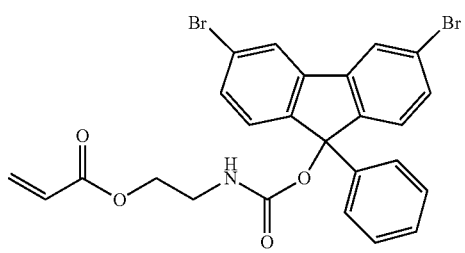
Formula II(g)
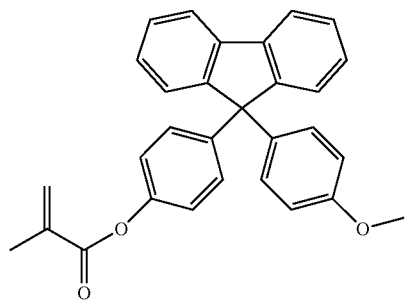
Formula II(h)
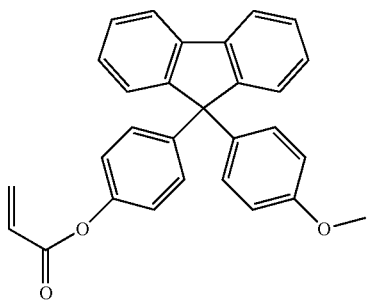
Formula II(i)
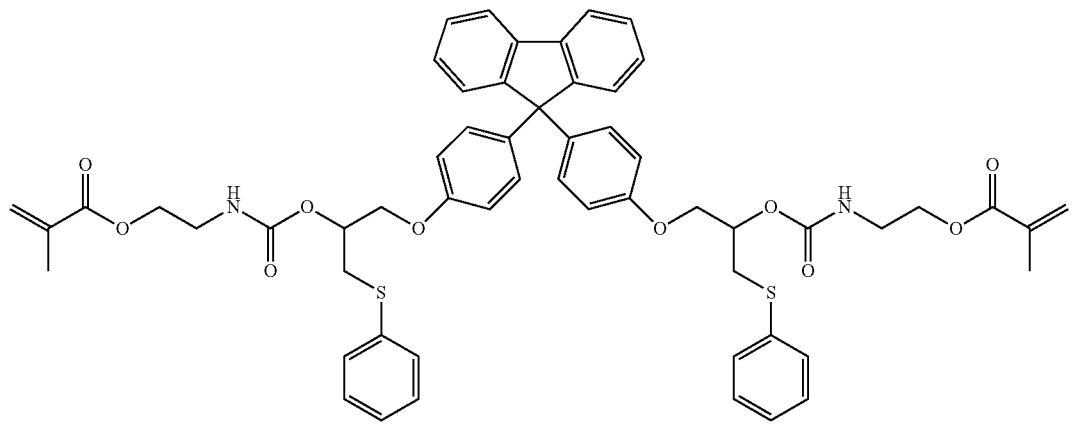

Formula II(j)

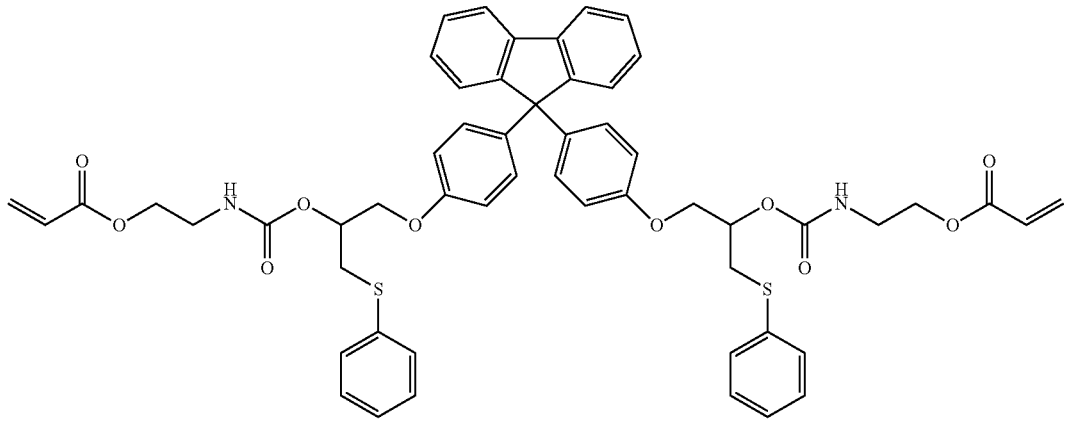

In some embodiments, the polymerizable component can include a compound of Formula III:

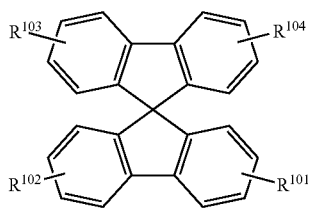

Formula III wherein in Formula III each $R^{101}$ to $R^{104}$ is independently a group of one, two, three, or four independently selected substituents, or no substituent, each substituent independently including one or more groups selected from optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, hydroxy, halo, cyano, trifluoromethyl, trifluoromethoxy, nitro, trimethylsilanyl, optionally substituted epoxide, optionally substituted glycidyl, optionally substituted acrylate, optionally substituted methacrylate, —$OR^a$, —$SR^a$, —OC(O)—$R^a$, —N($R^a$)$_2$, —C(O)$R^a$, —C(O)O$R^a$, —C(O)S$R^a$, —SC(O)$R^a$, —OC(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$, —S(O)$_t$O$R^a$, —S(O)$_t$N($R^a$)$_2$, —S(O)$_t$N($R^a$)C(O)$R^a$, (O)P(O$R^a$)$_3$, (S)P(OR)$_3$, and —(O)P(O$R^a$)$_2$; t is 1 or 2; each $R^a$ is independently selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, and optionally substituted heteroarylalkyl; and wherein at least one of $R^{101}$ to $R^{104}$ includes at least one substituent, the at least one substituent including a polymerizable or crosslinkable group.

In some embodiments, the polymerizable component can include a compound of Formula III, where a substituent includes one or more linking groups selected from —$C_{1-10}$ alkyl-, —O—$C_{1-10}$ alkyl-, —$C_{1-10}$ alkenyl-, —O—$C_{1-10}$ alkenyl-, —$C_{1-10}$ cycloalkenyl-, —O—$C_{1-10}$ cycloalkenyl-, —$C_{1-10}$ alkynyl-, —O—$C_{1-10}$ alkynyl-, —$C_{1-10}$ aryl-, —O—$C_{1-10}$ aryl-, —O—, —S—, —C(O)—, —C(O)O—, —OC(O)—, —OC(O)O—, —N($R^a$)—, —C(O)N($R^b$)—, —N($R^b$)C(O)—, —OC(O)N($R^b$), —N($R^b$)C(O)O—, —N($R^b$)C(O)N($R^b$)—, —N($R^b$)C(N$R^b$)N($R^b$)—, —N($R^b$)S(O)—, —S(O)N($R^b$, —S(O)$_w$O—, —OS(O)$_w$—, —OS(O)$_w$O—, —O(O)P(O$R^b$)O—, (O)P(O—)$_3$, —O(S)P (O$R^b$)O—, and (S)P(O—)$_3$, wherein w is 1 or 2, and R is independently hydrogen, optionally substituted alkyl, or optionally substituted aryl. In some embodiments, the substituent includes one or more linking groups selected from —(CH$_2$)$_n$—, 1,2 disubstituted phenyl, 1,3 disubstituted phenyl, 1,4 disubstituted phenyl, —CH═CH—, —C≡C—, —O—, —S—, —C(O)—, —C(O)O—, —OC(O)—, —OC(O)O—, —NH—, —C(O)NH—, —NHC(O)—, —OC(O)NH—, —NHC(O)O—, —NHC(O)NH—, —NHC(NH) NH—, —NHS(O)$_2$—, —S(O)$_2$NH—, —S(O)$_2$O—, —OS (O)$_2$—, —OS(O)O—, (O)P(O—)$_3$, and (S)P(O—)$_3$, wherein n is an integer from 1 to 12. In some embodiments, the substituent includes one or more linking groups selected from —(CH$_2$)$_2$—, 1,4 disubstituted phenyl, —CH═CH—, —O—, —C(O)—, —C(O)O—, —OC(O)—, —NH—, —C(O)NH—, —NHC(O)—, —OC(O)NH—, —NHC(O) O—, and (S)P(O—)$_3$. In some embodiments, the substituent includes one or more terminal groups selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, optionally substituted acrylate, optionally substituted methacrylate, optionally substituted styrene, optionally substituted epoxide, optionally substituted lactone, optionally substituted carbonate, hydroxy, halo, cyano, trifluoromethyl, trifluoromethoxy, nitro, and trimethylsilanyl. In some embodiments, the substituent includes one or more terminal groups selected from alkenyl and cycloalkenyl. In some embodiments, the substituent includes one or more terminal groups selected from optionally substituted acrylate, optionally substituted methacrylate, optionally substituted vinyl, and optionally substituted allyl. In some embodiments, the substituent includes one or more terminal groups selected from acrylate and methacrylate. In some embodiments, the polymerizable or crosslinkable group is selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted lactone, and optionally substituted carbonate. In some embodiments, the polymerizable or crosslinkable group is selected from acrylate and methacrylate. In some embodiments, the substituent is selected from:

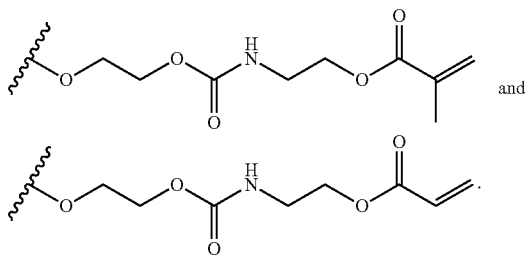

and

In some embodiments, the polymerizable component can include a compound of Formula III(a) or Formula III(b):

selected from optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, hydroxy, halo, cyano, trifluoromethyl, trifluoromethoxy, nitro, trimethylsilanyl, optionally substituted epoxide, optionally substituted glycidyl, optionally substituted acrylate, optionally substituted methacrylate, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$, —S(O)$_t$R$^a$, —S(O)$_t$OR$^a$, —S(O)$_t$N(R$^a$)$_2$, —S(O)$_t$N(R)C(O)R$^a$, —O(O)P(OR$^a$)$_2$, and —O(S)P(OR$^a$)$_2$; t is 1 or 2; each R$^a$ is independently selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, and optionally substituted heteroarylalkyl; and wherein at least one of R$^1$ to R$^{10}$ comprises a polymerizable or crosslinkable group.

Formula III(a)

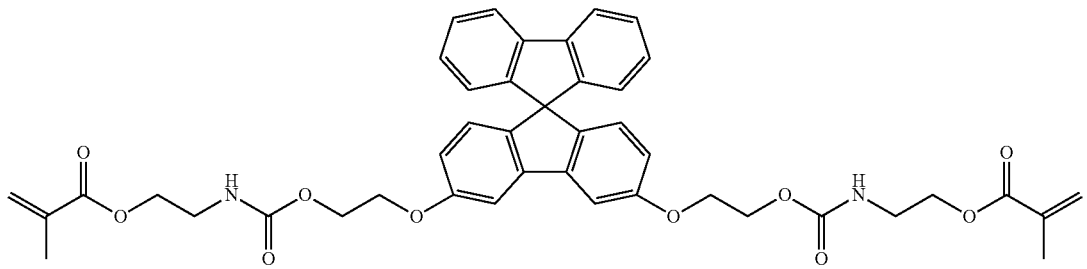

Formula III(b)

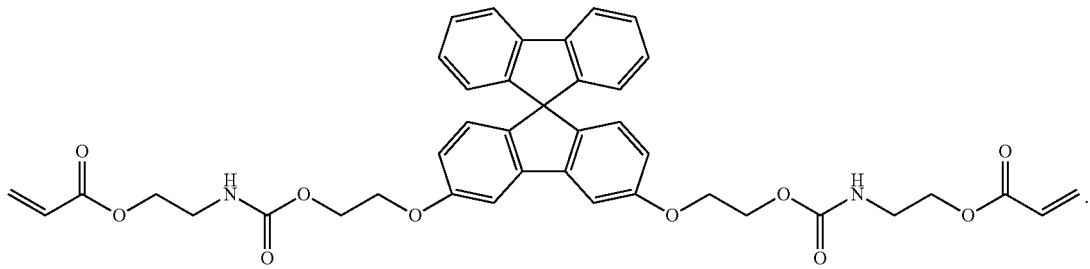

The following clauses describe certain embodiments.
Clause 1: a compound of Formula I:

Formula I

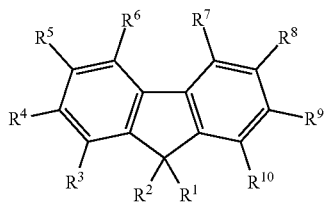

wherein in Formula I: each R$^1$ to R$^{10}$ is independently hydrogen or a substituent comprising one or more groups Clause 2: the compound of clause 1, wherein the substituent comprises one or more linking groups selected from —C$_{1-10}$ alkyl-, —O—C$_{1-10}$ alkyl-, —C$_{1-10}$ alkenyl-, —O—C$_{1-10}$ alkenyl-, —C$_{1-10}$ cycloalkenyl-, —O—C$_{1-10}$ cycloalkenyl-, —C$_{1-10}$ alkynyl-, —O—C$_{1-10}$ alkynyl-, —C$_{1-10}$ aryl-, —O—C$_{1-10}$ aryl-, —O—, —S—, —C(O)—, —C(O)O—, —OC(O)—, —C(O)S—, —SC(O)—, —OC(O)O—, —N(R$^b$)—, —C(O)N(R$^b$), —N(R$^b$)C(O)—, —OC(O)N(R$^b$)—, —N(R$^b$)C(O)O—, —SC(O)N(R$^b$)—, —N(R$^b$)C(O)S—, —N(R$^b$)C(O)N(R$^b$)—, —N(R$^b$)C(NR$^b$)N(R$^b$)—, —N(R$^b$)S(O)$_w$—, —S(O)N(R$^b$)—, —S(O)O—, —OS(O)$_w$—, —OS(O)$_w$O—, —O(O)P(OR$^b$)O—, (O)P(O—)$_3$, —O(S)P(OR$^b$)O—, and (S)P(O—)$_3$, wherein w is 1 or 2, and R$^b$ is independently hydrogen, optionally substituted alkyl, or optionally substituted aryl.

Clause 3: the compound of clause 1 or clause 2, wherein the substituent comprises one or more linking groups selected from —(CH$_2$)$_n$—, 1,2 disubstituted phenyl, 1,3 disubstituted phenyl, 1,4 disubstituted phenyl, disubstituted glycidyl, trisubstituted glycidyl, —CH=CH—, —C≡C—, —O—, —S—, —S(O)$_2$—, —C(O)—, —C(O)O—, —OC(O)—, —C(O)S—, —SC(O)—, —OC(O)O—, —NH—, —C(O)NH—, —NHC(O)—, —OC(O)NH—, —NHC(O)O—, —SC(O)NH—, —NHC(O)S—, —NHC(O)NH—, —NHC(NH)NH—, —NHS(O)$_2$—, —S(O)$_2$NH—, —S(O)$_2$O—, —OS(O)$_2$—, —OS(O)O—, (O)P(O—)$_3$, and (S)P(O—)$_3$, wherein n is an integer from 1 to 12.

Clause 4: the compound of any one of clause 1 or clause 2, wherein the substituent comprises one or more linking groups selected from —(CH$_2$)—, —(CH$_2$)$_2$—, —(CH$_2$)$_3$—, —(CH$_2$)$_4$—, —(CH$_2$)—, —(CH$_2$)—, 1,4 disubstituted phenyl, disubstituted glycidyl, trisubstituted glycidyl, —CH=CH—, —O—, —C(O)—, —C(O)O—, —OC(O)—, —NH—, —C(O)NH—, —NHC(O)—, —OC(O)NH—, —NHC(O)O—, —SC(O)NH—, —NHC(O)S—, and (S)P(O—)$_3$.

Clause 5: the compound of any one of clauses 1 to 4, wherein the substituent comprises one or more terminal groups selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, optionally substituted acrylate, optionally substituted methacrylate, optionally substituted styrene, optionally substituted epoxide, optionally substituted thiirane, optionally substituted glycidyl, optionally substituted lactone, optionally substituted carbonate, hydroxy, halo, cyano, trifluoromethyl, trifluoromethoxy, nitro, and trimethylsilanyl.

Clause 6: the compound of any one of clauses 1 to 5, wherein the substituent comprises one or more terminal groups selected from alkenyl, cycloalkenyl, optionally substituted aryl, and optionally substituted heteroaryl.

Clause 7: the compound of any one of clauses 1 to 6, wherein the substituent comprises one or more terminal groups selected from optionally substituted acrylate, optionally substituted methacrylate, optionally substituted vinyl, optionally substituted epoxide, optionally substituted thiirane, optionally substituted glycidyl, and optionally substituted allyl.

Clause 8: the compound of any one of clauses 1 to 7, wherein the substituent comprises one or more terminal groups selected from vinyl, allyl, epoxide, thiirane, glycidyl, acrylate, and methacrylate.

Clause 9: the compound of any one of clauses 1 to 8, wherein the substituent comprises one or more terminal groups selected from optionally substituted thiophenyl, optionally substituted thiopyranyl, optionally substituted thienothiophenyl, and optionally substituted benzothiophenyl.

Clause 10: the compound of any one of clauses 1 to 8, wherein the polymerizable or crosslinkable group is selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted thiirane, optionally substituted glycidyl, optionally substituted lactone, optionally substituted lactam, and optionally substituted carbonate.

Clause 11: the compound of any one of clauses 1 to 8, wherein the polymerizable or crosslinkable group is selected from vinyl, allyl, epoxide, thiirane, glycidyl, acrylate, and methacrylate.

Clause 12: the compound of any one of clauses 1 to 11, wherein the substituent comprises at least an aryl group Ar, wherein Ar is selected from substituted phenyl, substituted naphthyl, substituted anthracenyl, substituted phenanthrenyl, substituted phenalenyl, substituted tetracenyl, substituted chrysenyl, substituted triphenylenyl, and substituted pyrenyl.

Clause 13: the compound of clauses 12, wherein Ar is selected from 1,2-substituted phenyl, 1,3-substituted phenyl, and 1,4-substituted phenyl.

Clause 14: the compound of any one of clauses 1 to 13, having Formula I(a):

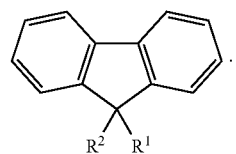

Formula I(a)

Clause 15: a compound of Formula II:

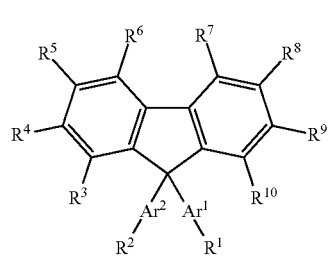

Formula II wherein in Formula II: Ar$^1$ and Ar$^2$ are independently selected from a bond, optionally substituted alkyl, optionally substituted aryl, optionally substituted arylalkyl, optionally substituted heteroaryl, and optionally substituted heteroarylalkyl; each R$^1$ to R$^{10}$ is independently hydrogen or a substituent comprising one or more groups selected from optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, hydroxy, halo, cyano, trifluoromethyl, trifluoromethoxy, nitro, trimethylsilanyl, optionally substituted epoxide, optionally substituted glycidyl, optionally substituted acrylate, optionally substituted methacrylate, —OR$^a$, —SR$^a$, —OC(O)—R$^a$, —N(R$^a$)$_2$, —C(O)R$^a$, —C(O)OR$^a$, —C(O)SR$^a$, —SC(O)R$^a$, —OC(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$—S(O)$_t$OR$^a$, —S(O)$_t$N(R$^a$)$_2$, —S(O)$_t$N(R$^a$)C(O)R$^a$, —O(O)P(OR$^a$)$_2$, and —O(S)P(OR$^a$)$_2$; t is 1 or 2; each R$^a$ is independently selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, and optionally substituted heteroarylalkyl; and wherein at least one of R$^1$ to R$^{10}$ comprises a polymerizable or crosslinkable group.

Clause 16: the compound of clause 15, having Formula I(a):

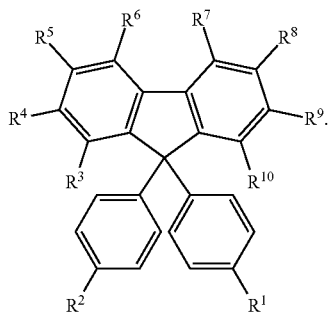

Formula II(a)

Clause 17: the compound of clause 15 or clause 16, wherein the substituent comprises one or more linking groups selected from —C$_{1-10}$ alkyl-, —O—C$_{1-10}$ alkyl-, —C$_{1-10}$ alkenyl-, —O—C$_{1-10}$ alkenyl-, —C$_{1-10}$ cycloalkenyl-, —O—C$_{1-10}$ cycloalkenyl-, —C$_{1-10}$ alkynyl-, —O—C$_{1-10}$ alkynyl-, —C$_{1-10}$ aryl-, —O—C$_{1-10}$ aryl-, —O—, —S—, —C(O)—, —C(O)O—, —OC(O)—, —OC(O)O—, —N(R$^b$)—, —C(O)N(R$^b$)—, —N(R$^b$)C(O)—, —OC(O)N(R$^b$)—, —N(R$^b$)C(O)O—, —N(R$^b$)C(O)N(R$^b$)—, —N(R$^b$)C(NR$^b$)N(R$^b$)—, —N(R$^b$)S(O)$_w$—, —S(O)$_w$N(R$^b$)—, —S(O)$_w$O—, —OS(O)$_w$—, —OS(O)O—, —O(O)P(OR$^b$)O—, (O)P(O—)$_3$, —O(S)P(OR$^b$)O—, and (S)P(O—)$_3$, wherein w is 1 or 2, and R$^b$ is independently hydrogen, optionally substituted alkyl, or optionally substituted aryl.

Clause 18: the compound of any one of clauses 15 to 17, wherein the substituent comprises one or more linking groups selected from —(CH$_2$)$_n$—, 1,2 disubstituted phenyl, 1,3 disubstituted phenyl, 1,4 disubstituted phenyl, disubstituted glycidyl, trisubstituted glycidyl, —CH=CH—, —C≡C—, —O—, —S—, —S(O)$_2$—, —C(O)—, —C(O)O—, —OC(O)—, —C(O)S—, —SC(O)—, —OC(O)O—, —NH—, —C(O)NH—, —NHC(O)—, —OC(O)NH—, —NHC(O)O—, —NHC(O)NH—, —NHC(NH)NH—, —NHS(O)$_2$—, —S(O)$_2$NH—, —S(O)$_2$O—, —OS(O)$_2$—, —OS(O)O—, (O)P(-)$_3$, and (S)P(O—)$_3$, wherein n is an integer from 1 to 12.

Clause 19: the compound of any one of clauses 15 to 18, wherein the substituent comprises one or more linking groups selected from —(CH$_2$)—, —(CH$_2$)$_2$—, —(CH$_2$)$_3$—, —(CH$_2$)$_4$—, —(CH$_2$)—, —(CH$_2$)—, 1,4 disubstituted phenyl, disubstituted glycidyl, trisubstituted glycidyl, —CH=CH—, —O—, —C(O)—, —C(O)O—, —OC(O)—, —NH—, —C(O)NH—, —NHC(O)—, —OC(O)NH—, —NHC(O)O—, —SC(O)NH—, —NHC(O)S—, and (S)P(O—)$_3$.

Clause 20: the compound of any one of clauses 15 to 19, wherein the substituent comprises one or more terminal groups selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, optionally substituted acrylate, optionally substituted methacrylate, optionally substituted styrene, optionally substituted epoxide, optionally substituted thiirane, optionally substituted glycidyl, optionally substituted lactam, optionally substituted lactone, optionally substituted carbonate, hydroxy, halo, cyano, trifluoromethyl, trifluoromethoxy, nitro, and trimethylsilanyl.

Clause 21: the compound of any one of clauses 15 to 20, wherein the substituent comprises one or more terminal groups selected from alkenyl, cycloalkenyl, optionally substituted aryl, and optionally substituted heteroaryl.

Clause 22: the compound of any one of clauses 15 to 21, wherein the substituent comprises one or more terminal groups selected from optionally substituted acrylate, optionally substituted methacrylate, optionally substituted vinyl, optionally substituted epoxide, optionally substituted thiirane, optionally substituted glycidyl, and optionally substituted allyl.

Clause 23: the compound of any one of clauses 15 to 22, wherein the substituent comprises one or more terminal groups selected from vinyl, allyl, epoxide, thiirane, glycidyl, acrylate, and methacrylate.

Clause 24: the compound of any one of clauses 15 to 23, wherein the substituent comprises one or more terminal groups selected from optionally substituted thiophenyl, optionally substituted thiopyranyl, optionally substituted thienothiophenyl, and optionally substituted benzothiophenyl.

Clause 25: the compound of any one of clauses 15 to 24, wherein the polymerizable or crosslinkable group is selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted thiirane, optionally substituted glycidyl, optionally substituted lactone, optionally substituted lactam, and optionally substituted carbonate.

Clause 26: the compound of any one of clauses 15 to 24, wherein the polymerizable or crosslinkable group is selected from acrylate and methacrylate.

Clause 27: the compound of any one of clauses 15 to 26, having Formula II(b):

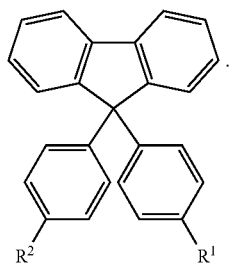

Formula II(b)

Clause 28: the compound of any one of clauses 1 to 27, wherein the substituent is selected from:

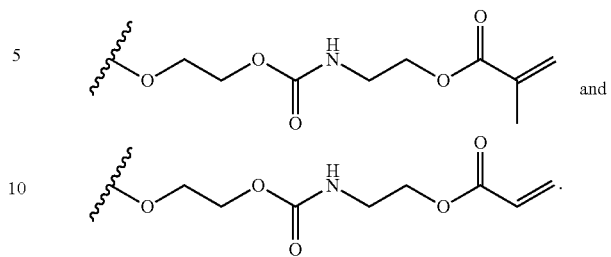

and

Clause 29: the compound of any one of clauses 1 to 28, having Formula II(c), Formula II(d), Formula II(e), Formula II(f), Formula II(g), Formula II(h), Formula II(i), or Formula II(j):

Formula II(c)

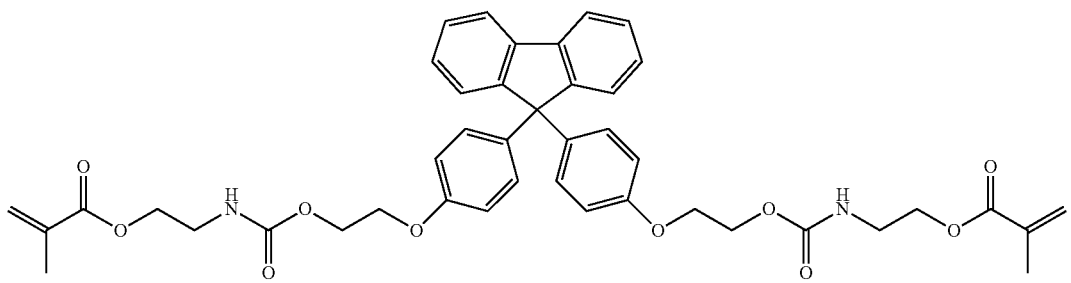

Formula II(d)

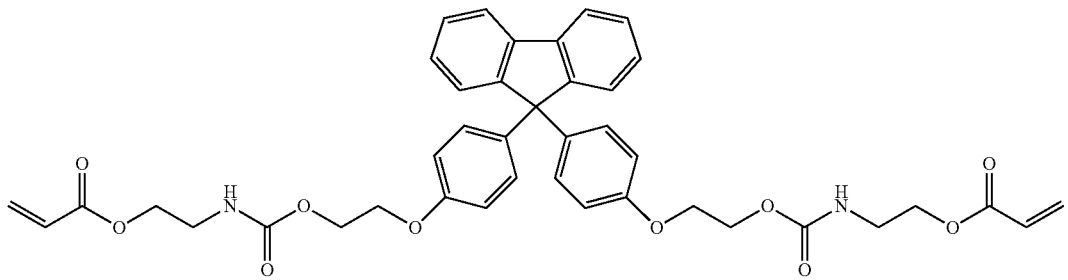

Formula II(e)

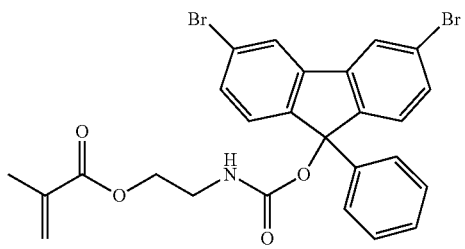

Formula II(f)

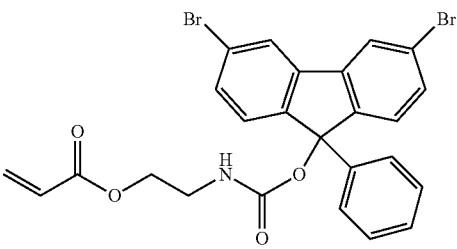

Formula II(g)

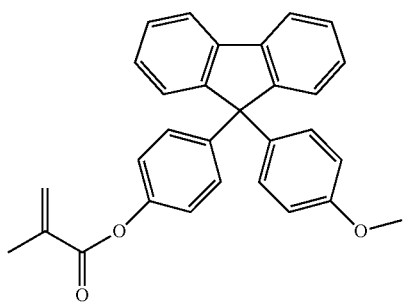

Formula II(h)

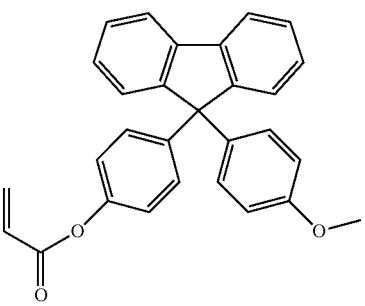

Formula II(i)

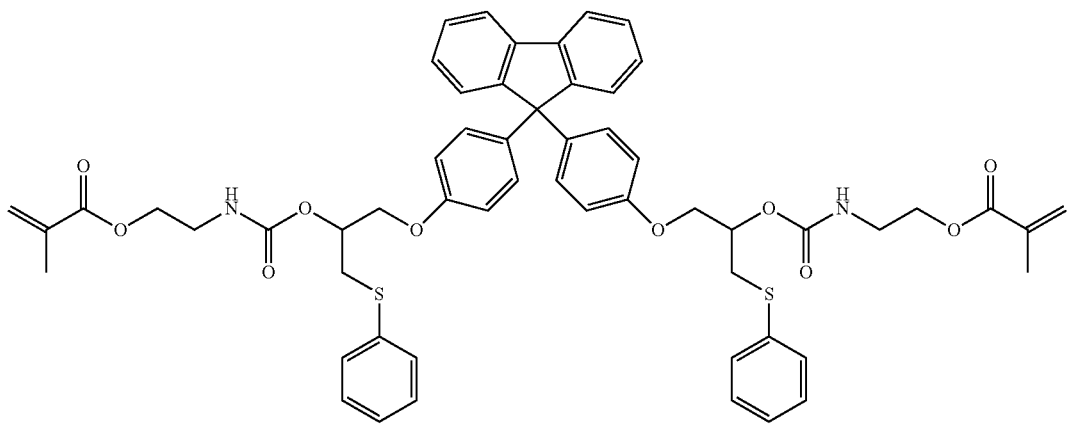

Formula II(j)

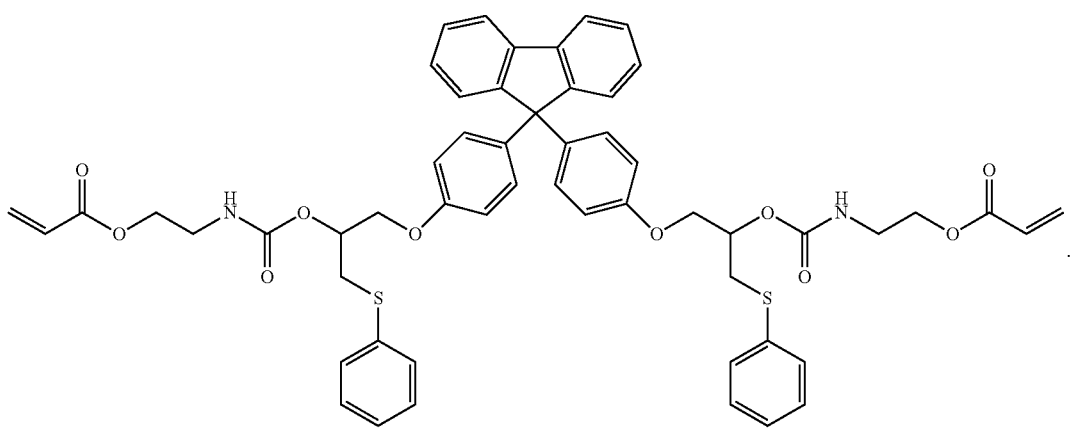

Clause 30: a compound of Formula III:

Formula III

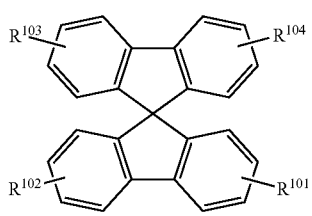

wherein in Formula III: each $R^{101}$ to $R^{104}$ is independently a group of one, two, three, or four independently selected substituents, or no substituent, each substituent independently comprising one or more groups selected from optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, hydroxy, halo, cyano, trifluoromethyl, trifluoromethoxy, nitro, trimethylsilanyl, optionally substituted epoxide, optionally substituted glycidyl, optionally substituted acrylate, optionally substituted methacrylate, —$OR^a$, —$SR^a$, —OC(O)—$R^a$, —$N(R^a)_2$, —C(O)$R^a$, —C(O)O$R^a$, —C(O)S$R^a$, —SC(O)$R^a$, —OC(O)O$R^a$, —OC(O)N($R^a)_2$, —C(O)N($R^a)_2$, —N($R^a$)C(O)O$R^a$, —N($R^a$)C(O)$R^a$, —N($R^a$)C(O)N($R^a)_2$, N($R^a$)C(N$R^a$)N($R^a)_2$, —N($R^a$)S(O)$_t R^a$, —S(O)$_t OR^a$, —S(O)$_t$N($R^a)_2$, —S(O)$_t$N($R^a$)C(O)$R^a$, (O)P(O$R^a)_3$, (S)P(O$R^a)_3$, and —(O)P(O$R^a)_2$; t is 1 or 2; each $R^a$ is independently selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, and optionally substituted heteroarylalkyl; and wherein at least one of $R^{101}$ to $R^{104}$ comprises at least one substituent, the at least one substituent comprising a polymerizable or crosslinkable group.

Clause 31: the compound of clause 30, wherein the substituent comprises one or more linking groups selected from —$C_{1-10}$ alkyl-, —O—$C_{1-10}$ alkyl-, —$C_{1-10}$ alkenyl-, —O—$C_{1-10}$ alkenyl-, —$C_{1-10}$ cycloalkenyl-, —O—$C_{1-10}$ cycloalkenyl-, —$C_{1-10}$ alkynyl-, —O—$C_{1-10}$ alkynyl-, —C$_{1-10}$ aryl-, —O—C$_{1-10}$ aryl-, —O—, —S—, —C(O)—, —C(O)O—, —OC(O)—, —OC(O)O—, —N(R$^a$)—, —C(O)N(R$^b$)—, —N(R$^b$)C(O)—, —OC(O)N(R$^b$)—, —N(R$^b$)C(O)O—, —N(R$^b$)C(O)N(R$^b$)—, —N(R$^b$)C(NR$^b$)N(R$^b$)—, —N(R$^b$)S(O)$_w$—, —S(O)$_w$N(R$^b$)—, —S(O)$_w$O—, —OS(O)$_w$—, —OS(O)$_w$O—, —O(O)P(OR$^b$)O—, (O)P(O—)$_3$, —O(S)P(OR$^b$)O—, and (S)P(O—)$_3$, wherein w is 1 or 2, and R$^b$ is independently hydrogen, optionally substituted alkyl, or optionally substituted aryl.

Clause 32: the compound of clause 30 or clause 31, wherein the substituent comprises one or more linking groups selected from —(CH$_2$)$_n$—, 1,2 disubstituted phenyl, 1,3 disubstituted phenyl, 1,4 disubstituted phenyl, disubstituted glycidyl, trisubstituted glycidyl, —CH=CH—, —C=C—, —O—, —S—, —S(O)$_2$—, —C(O)—, —C(O)O—, —OC(O)—, —C(O)S—, —SC(O)—, —OC(O)O—, —NH—, —C(O)NH—, —NHC(O)—, —OC(O)NH—, —NHC(O)O—, —NHC(O)NH—, —NHC(NH)NH—, —NHS(O)$_2$—, —S(O)$_2$NH—, —S(O)$_2$—, —OS(O)$_2$—, —OS(O)$_2$O—, (O)P(O—)$_3$, and (S)P(O—)$_3$, wherein n is an integer from 1 to 12.

Clause 33: the compound of clause 30 or clause 31, wherein the substituent comprises one or more linking groups selected from —(CH$_2$)—, —(CH$_2$)$_2$—, —(CH$_2$)$_3$—, —(CH$_2$)$_4$—, —(CH$_2$)$_5$—, —(CH$_2$)$_6$—, 1,4 disubstituted phenyl, disubstituted glycidyl, trisubstituted glycidyl, —CH=CH—, —O—, —C(O)—, —C(O)O—, —OC(O)—, —NH—, —C(O)NH—, —NHC(O)—, —OC(O)NH—, —NHC(O)O—, —SC(O)NH—, —NHC(O)S—, and (S)P(O—)$_3$.

Clause 34: the compound of any one of clauses 30 to 33, wherein the substituent comprises one or more terminal groups selected from hydrogen, optionally substituted alkyl, optionally substituted heteroalkyl, optionally substituted alkenyl, optionally substituted alkynyl, optionally substituted cycloalkyl, optionally substituted heterocycloalkyl, optionally substituted aryl, optionally substituted arylalkyl, optionally substituted heteroaryl, optionally substituted heteroarylalkyl, optionally substituted acrylate, optionally substituted methacrylate, optionally substituted styrene, optionally substituted epoxide, optionally substituted thiirane, optionally substituted glycidyl, optionally substituted lactam, optionally substituted lactone, optionally substituted carbonate, hydroxy, halo, cyano, trifluoromethyl, trifluoromethoxy, nitro, and trimethylsilanyl.

Clause 35: the compound of any one of clauses 30 to 33, wherein the substituent comprises one or more terminal groups selected from alkenyl, cycloalkenyl, optionally substituted aryl, and optionally substituted heteroaryl.

Clause 36: the compound of any one of clauses 30 to 33, wherein the substituent comprises one or more terminal groups selected from optionally substituted acrylate, optionally substituted methacrylate, optionally substituted vinyl, optionally substituted epoxide, optionally substituted thiirane, optionally substituted glycidyl, and optionally substituted allyl.

Clause 37: the compound of any one of clauses 30 to 36, wherein the substituent comprises one or more terminal groups selected from vinyl, allyl, epoxide, thiirane, glycidyl, acrylate and methacrylate.

Clause 38: the compound of any one of clauses 30 to 36, wherein the substituent comprises one or more terminal groups selected from optionally substituted thiophenyl, optionally substituted thiopyranyl, optionally substituted thienothiophenyl, and optionally substituted benzothiophenyl.

Clause 39: the compound of any one of clauses 30 to 38, wherein the polymerizable or crosslinkable group is selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted thiirane, optionally substituted glycidyl, optionally substituted lactone, optionally substituted lactam, and optionally substituted carbonate.

Clause 40: the compound of any one of clauses 30 to 38, wherein the polymerizable or crosslinkable group is selected from acrylate and methacrylate.

Clause 41: the compound of any one of clauses 26 to 35, wherein the substituent is selected from:

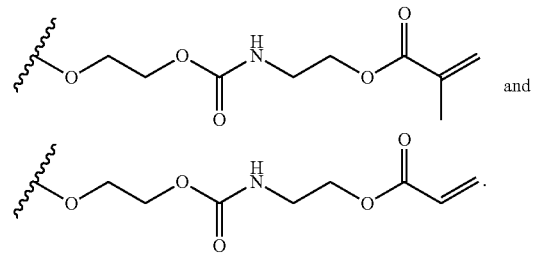

and

Clause 42: the compound of any one of clauses 26 to 36, having Formula III(a) or Formula III(b):

Formula III(a)

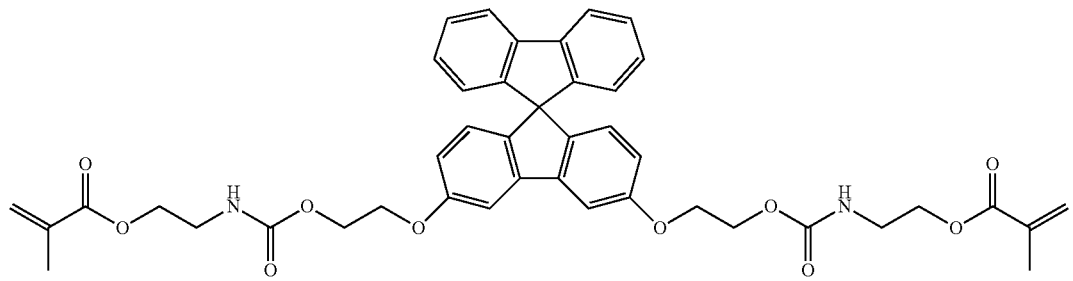

-continued

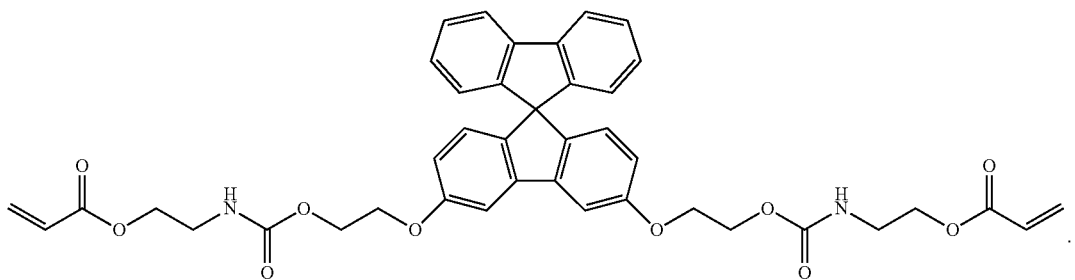

Formula III(b)

Clause 43: the compound of any one of clauses 1 to 41, wherein the substituent comprises one or more groups selected from —Me, —OMe, —OPh, —SMe, —SPh, —F, —Cl, —Br, and —I.

Clause 44: the compound of any one of clauses 1 to 41, wherein the substituent comprises one or more groups selected from

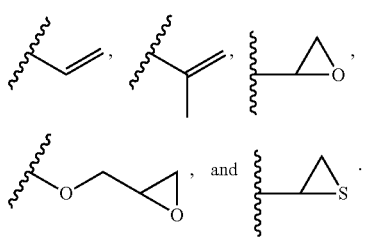

Clause 45: the compound of any one of clauses 1 to 41, wherein the substituent comprises one or more groups selected from

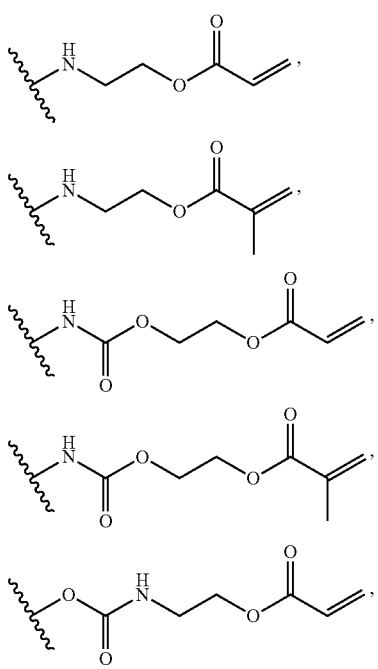

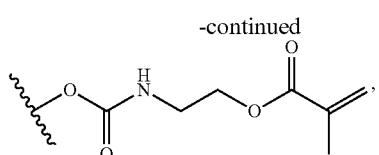

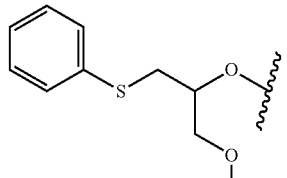

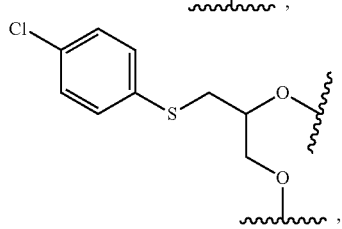

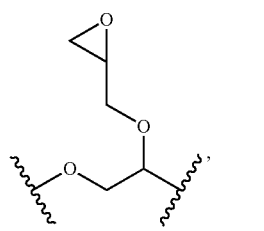

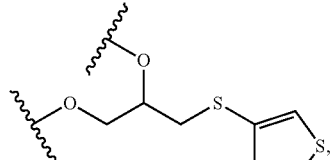

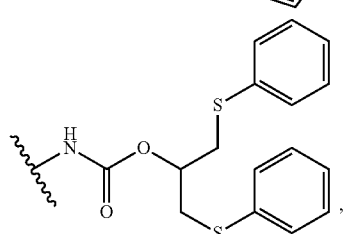

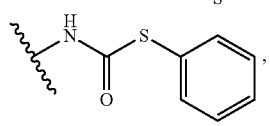

-continued
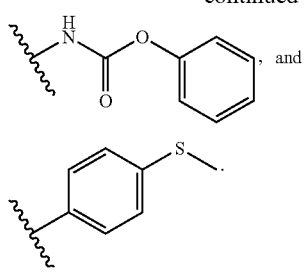
, and
Clause 46: the compound of any one of clauses 1 to 41, wherein the substituent comprises one or more groups selected from:
-continued
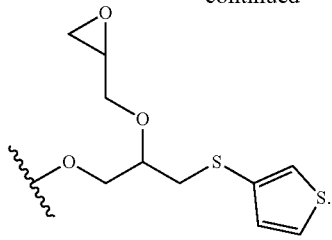
Clause 47: the compound of any one of clauses 1 to 41, wherein the compound comprises one or more groups selected from:
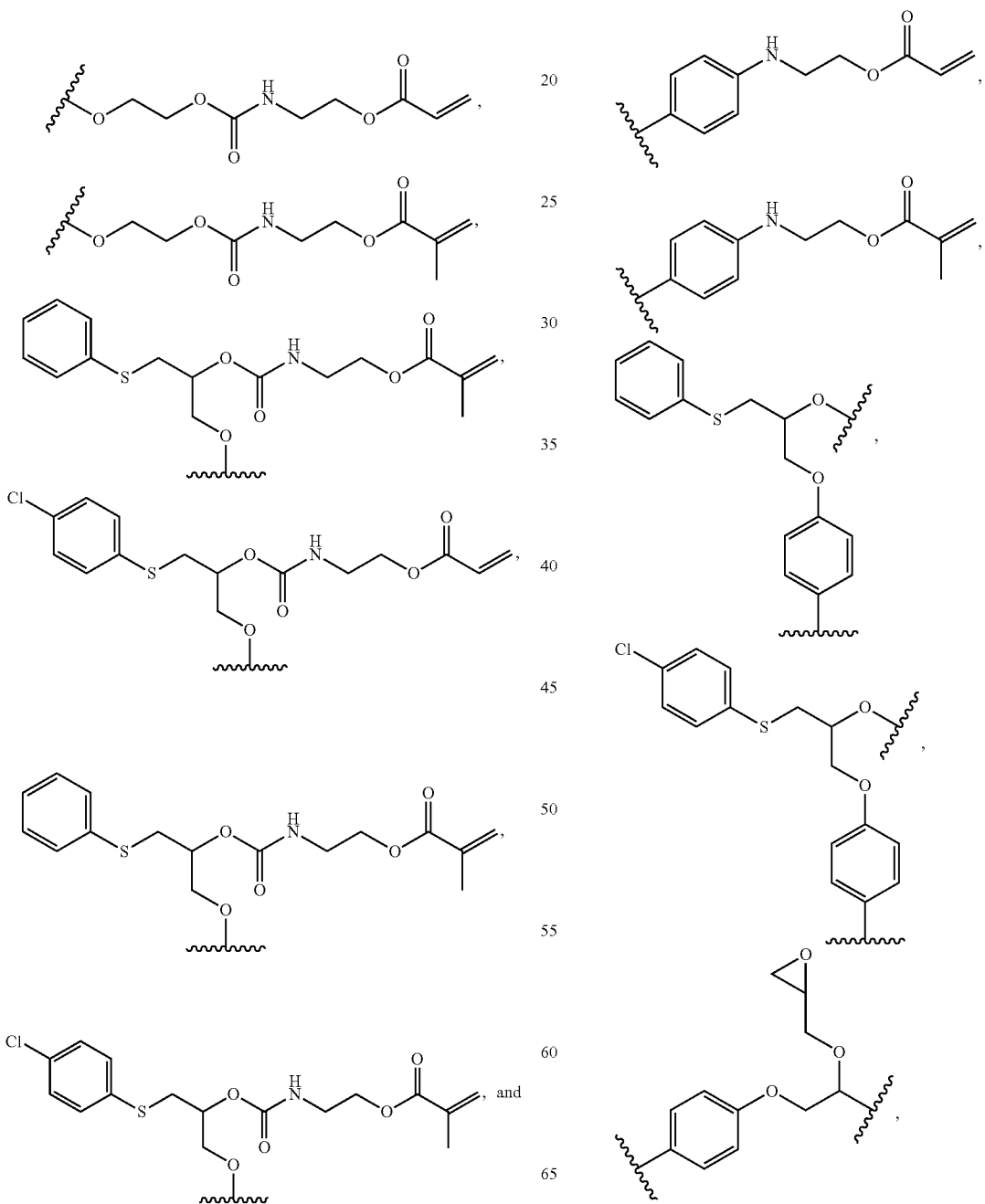

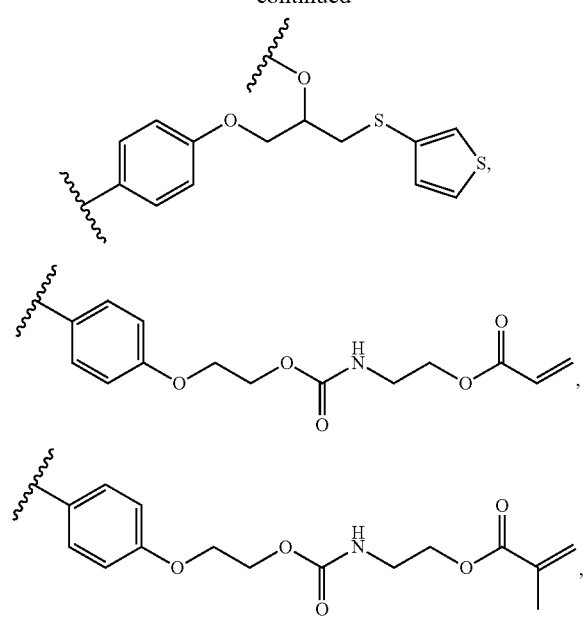
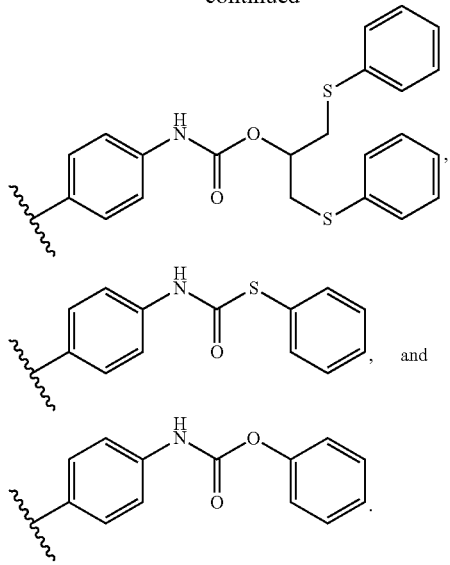
Clause 48: the compound of any of clauses 1 to 41, wherein the compound comprises one or more groups selected from:
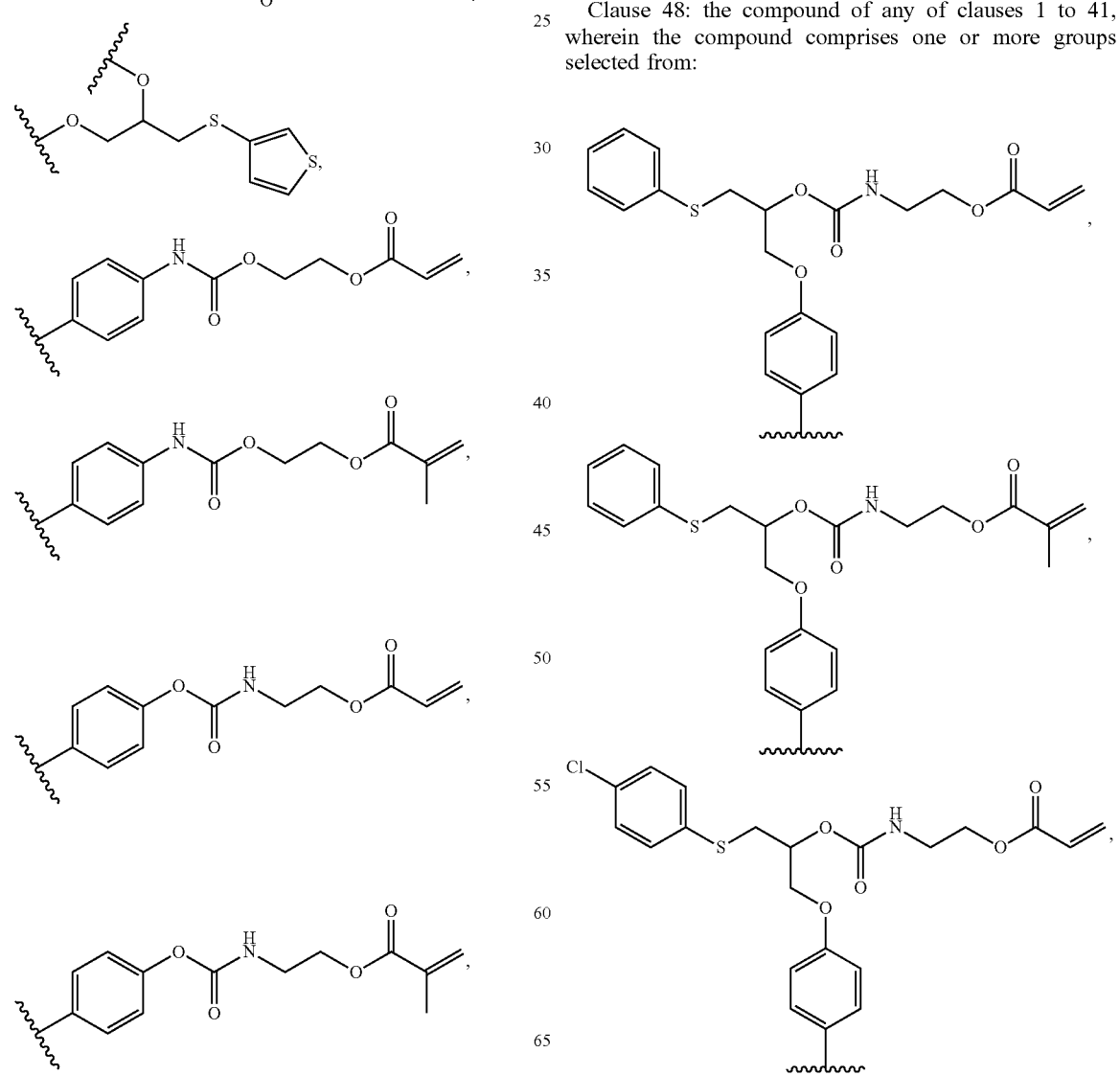

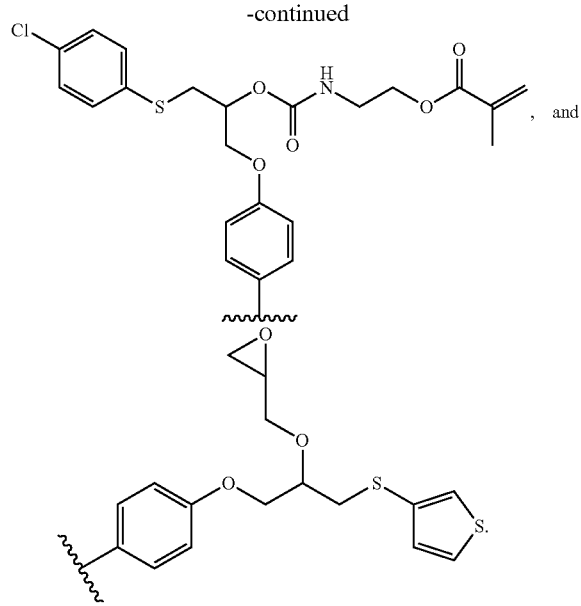
, and

As described herein, relatively high index contrast is desired in an article, whether for improved readout in a recording media or efficient light confinement in a waveguide. In addition, it is advantageous to induce this relatively large index change with a small number of monomer functional groups, because polymerization of the monomer generally induces shrinkage in a material. Such shrinkage has a detrimental effect on the retrieval of data from stored holograms, and also degrades the performance of waveguide devices such as by increased transmission losses or other performance deviations. In some embodiments, lowering the number of monomer functional groups that must be polymerized to attain the necessary index contrast is therefore desirable. This lowering is possible by increasing the ratio of the molecular volume of the monomers to the number of monomer functional groups on the monomers. This increase is attainable by incorporating into a monomer larger index-contrasting moieties and/or a larger number of index-contrasting moieties. For example, if the matrix is composed primarily of aliphatic or other low index moieties and the monomer is a higher index species where the higher index is imparted by a benzene ring, the molecular volume could be increased relative to the number of monomer functional groups by incorporating a naphthalene ring instead of a benzene ring (the naphthalene having a larger volume), or by incorporating one or more additional benzene rings, without increasing the number of monomer functional groups. In this manner, polymerization of a given volume fraction of the monomers with the larger molecular volume/monomer functional group ratio would require polymerization of less monomer functional groups, thereby inducing less shrinkage. But the requisite volume fraction of monomer would still diffuse from the unexposed region to the exposed region, providing the desired refractive index.

The molecular volume of the monomer, however, should not be so large as to slow diffusion below an acceptable rate. Diffusion rates are controlled by factors including size of diffusing species, viscosity of the medium, and intermolecular interactions. Larger species tend to diffuse more slowly, but it would be possible in some situations to lower the viscosity or make adjustments to the other molecules present in order to raise diffusion to an acceptable level. Also, as described herein, it is important to ensure that larger molecules maintain compatibility with the matrix.

Numerous architectures are possible for monomers containing multiple index-contrasting moieties. For example, it is possible for the moieties to be in the main chain of a linear oligomer, or to be substituents along an oligomer chain. Alternatively, it is possible for the index-contrasting moieties to be the subunits of a branched or dendritic low molecular weight polymer.

In addition to the at least one photoactive polymerizable material, an article of the present disclosure may contain a photoinitiator. The photoinitiator chemically initiates the polymerization of the at least one photoactive polymerizable material. The photoinitiator generally should offer a source of species that initiate polymerization of the particular photoactive polymerizable material, e.g., photoactive monomer. Typically, from about 0.1 to about 20 vol. % photoinitiator provides desirable results.

A variety of photoinitiators known to those skilled in the art and available commercially are suitable for use as described herein, for example, those comprising a phosphine oxide group, such as diphenyl(2,4,6-trimethylbenzoyl)phosphine oxide, disclosed in U.S. Pat. No. 6,780,546 (Trentler et al.), issued Aug. 24, 2004, incorporated herein by reference. In some embodiments, the photoinitiator is sensitive to light at wavelengths available from conventional laser sources, e.g., the blue and green lines of $Ar^+$ (458, 488, 514 nm) and He—Cd lasers (442 nm), the green line of frequency doubled YAG lasers (532 nm), and the red lines of He—Ne (633 nm), $Kr^+$ lasers (647 and 676 nm), and various diode lasers (290 to 900 nm). In some embodiments, the free radical photoinitiator bis($\eta$-5-2,4-cyclopentadien-1-yl)bis[2,6-difluoro-3-(1H-pyrrol-1-yl)phenyl]titanium can be used. In some embodiments, the free-radical photoinitiator 5,7-diiodo-3-butoxy-6-fluorone can be used. In some embodiments, this photoinitiator requires a co-initiator. Free-radical photoinitiators of dye-hydrogen donor systems can also be used. Examples of suitable dyes include eosin, rose bengal, erythrosine, and methylene blue, and suitable hydrogen donors include tertiary amines such as n-methyl diethanol amine. In the case of cationically polymerizable components, a cationic photoinitiator is used, such as a sulfonium salt or an iodonium salt. These cationic photoinitiator salts absorb predominantly in the UV portion of the spectrum, and are therefore typically sensitized with a sensitizer or dye to allow use of the visible portion of the spectrum. An example of an alternative visible cationic photoinitiator is ($\eta_5$-2,4-cyclopentadien-1-yl) ($\eta_6$-isopropylbenzene)-iron (II) hexafluorophosphate. In some embodiments, photoinitiators used herein are sensitive to ultraviolet and visible radiation of from about 200 nm to about 800 nm. In some embodiments, other additives can be used in the photoimageable system, e.g., inert diffusing agents having relatively high or low refractive indices.

In some embodiments, an article described herein may also include additives such as plasticizers for altering the properties of the article of the present disclosure including the melting point, flexibility, toughness, diffusibility of the monomers and/or oligomers, and ease of processability. Examples of suitable plasticizers include dibutyl phthalate, poly(ethylene oxide) methyl ether, N,N-dimethylformamide, etc. Plasticizers differ from solvents in that solvents are typically evaporated whereas plasticizers are meant to remain in the article.

Other types of additives that may be used in the liquid mixture and article of the present disclosure are inert diffusing agents having relatively high or low refractive indices. Inert diffusing agents typically diffuse away from the grating being formed, and can be of high or low refractive index. In some embodiments, additives used herein have low refractive index. In some embodiments, a monomer of high refractive index is used with an inert diffusing agent of low refractive index. In some embodiments, the inert diffusing agent diffuses to the nulls in an interference pattern. In some embodiments, such diffusion leads to the contrast of the grating being increased. Other additives that may be used in the liquid mixture and article of the present disclosure include: pigments, fillers, nonphotoinitiating dyes, antioxidants, bleaching agents, mold releasing agents, antifoaming agents, infrared/microwave absorbers, surfactants, adhesion promoters, etc.

In some embodiments, the polymerizable component of an article of the present disclosure is less than about 20 volume %. In some embodiments, the polymerizable component of an article of the present disclosure may be less than about 10 volume %, or even less than about 5 volume %. For data storage applications, the typical polymerizable component is present at about 5 volume %, about 6 volume %, about 7 volume %, about 8 volume %, about 9 volume %, about 10 volume %, about 11 volume %, about 12 volume %, about 13 volume %, about 14 volume %, or about 15 volume %. In some embodiments, the polymerizable component is present at about 1 volume %, about 2 volume %, about 3 volume %, about 4 volume %, about 5 volume %, about 6 volume %, about 7 volume %, about 8 volume %, about 9 volume %, about 10 volume %, about 11 volume %, about 12 volume %, about 13 volume %, about 14 volume %, about 15 volume %, about 16 volume %, about 17 volume %, about 18 volume %, about 19 volume %, or about 20 volume %.

An article described herein may be any thickness needed. In some embodiments, the article may be thin for display holography or thick for data storage. In some embodiments, the article may be, without limitations, a film deposited on a substrate, a free flexible film (for example a film similar to food wraps), or a hard article requiring no substrate (for example similar to a credit card). For data storage applications, in some embodiments, the article will typically be from about 1 to about 1.5 mm in thickness, and is typically in the form of a film deposited between two substrates with at least one of the substrates having an antireflective coating; the article would also likely be sealed against moisture and air.

An article of the present disclosure may be heated to form a liquid mixture that is infused into a porous substrate such as glass, cloth, paper, wood, or plastic, then allowed to cool. Such articles would be able to record holograms of a display and/or data nature.

An article of the present disclosure may be made optically flat via the appropriate processes, such as the process described in U.S. Pat. No. 5,932,045 (Campbell et al.), issued Aug. 3, 1999, incorporated herein by reference.

By choosing between a wide variety of matrix types to be used in an article described herein, reduction or elimination of problems such as water or humidity can be achieved. In one embodiment, an article described herein may be used to store volatile holograms. Due to the ability to control the photopolymer chain length as described herein, a particular mixture may be tuned to have a very general lifetime for the recorded holograms. Thus, after hologram recording, holograms may be readable for a defined time period such as a week, a few months, or years. Heating the article may also increase such a process of hologram destruction.

In some embodiments, volatile holograms can be used for rental movies, security information, tickets (or season passes), thermal history detector, time stamp, and/or temporary personal records, etc.

In some embodiments, an article described herein may be used to record permanent holograms. There are several methods to increase the permanency of recorded holograms. In some embodiments, these methods involve placing functional groups on the matrix that allow for the attachment of photopolymer to the matrix during cure. The attachment groups can be vinyl unsaturations, chain transfer sites, or polymerization retarders such as a BHT derivative. Otherwise, for increased archival stability of recorded holograms, a multifunctional monomer may be used which allows for crosslinking of the photopolymer, thus increasing the entanglement of the photopolymer in the matrix. In some embodiments, both a multifunctional monomer and a matrix-attached retarder are used. In this way, the shorter chains that are caused by the polymerization retarder do not cause loss of archival life.

In addition to the photopolymeric systems described herein, various photopolymeric systems may be used in the holographic recording medium described herein. For example, suitable photopolymeric systems for use in the present disclosure are described in: U.S. Pat. No. 6,103,454 (Dhar et al.), U.S. Pat. No. 6,482,551 (Dhar et al.), U.S. Pat. No. 6,650,447 (Curtis et al.), U.S. Pat. No. 6,743,552 (Setthachayanon et al.), U.S. Pat. No. 6,765,061 (Dhar et al.), U.S. Pat. No. 6,780,546 (Trentler et al.), U.S. Patent Application No. 2003-0206320, published Nov. 6, 2003, (Cole et al), and U.S. Patent Application No. 2004-0027625, published Feb. 12, 2004, incorporated by reference herein.

An article of the present disclosure may be ground, shredded, fragmented, etc. to form a particle material of powder, chips, etc. The particle material may be heated at a later time to form a flowable liquid used to make a molded product, a coating to apply to a substrate, etc.

In some embodiments, an article described herein is used to make data storage devices of various sizes and shapes, as a block of material or as part of a coating that is coated on a substrate.

In some embodiments, the disclosure provides methods for controlling photopolymerization reactions in the holographic recording medium. In some embodiments, the disclosure provides methods for reducing, minimizing, diminishing, eliminating, etc., dark reactions in the photopolymeric systems used in such a holographic recording medium. In some embodiments, such methods include using one or more of the following: (1) a polymerization retarder; (2) a polymerization inhibitor; (3) a chain transfer agent; (4) use of metastable reactive centers; (5) use of light or heat labile phototerminators; (6) use of photo-acid generators, photo-base generators or photogenerated radicals; (7) use of polarity or solvation effects; (8) counter ion effects; and (9) changes in photoactive polymerizable material reactivity. Methods for controlling radical polymerization are described in "Controlled Radical Polymerization Guide: ATRP, RAFT, NMP," Aldrich, 2012, incorporated by reference herein (See, e.g., Jakubowski, Tsarevsky, McCarthy, and Matyjaszewsky: "ATRP (Atom Transfer Radical Polymerization) for Everyone: Ligands and Initiators for the Clean Synthesis of Functional Polymers;" Grajales: "Tools for Performing ATRP;" Haddleton: "Copper(I)-mediated Living Radical Polymerization in the Presence of Pyridyl-methanimine Ligands;" Haddleton: "Typical Procedures for Polymerizing via ATRP;" Zhu, Edmondson: "Applying ARGET ATRP to the Growth of Polymer Brush Thin Films by Surface-initiated Polymerization;" Zhu, Edmondson: "ARGET ATRP: Procedure for PMMA Polymer Brush Growth;" "Ligands for ATRP Catalysts;" "Metal Salts for ATRP Catalysts;" "Reversible Addition/Fragmentation Chain Transfer Polymerization (RAFT);" Moad, Rizzardo, and Thang: "A Micro Review of Reversible Addition/Fragmentation Chain Transfer (RAFT) Polymerization;" "Concepts and Tools for RAFT Polymerization;" "Typical Procedures for Polymerizing via RAFT;" "Universal/Switchable RAFT Agents for Well-defined Block Copolymers: Agent Selection and Polymerization;" "Polymerization Procedure with Universal/Switchable RAFT Agents;" "RAFT Agents;" "Switchable RAFT Agents;" "Radical Initiators;" "Nitroxide-mediated Polymerization (NMP);" Lee and Wooley: "Block Copolymer Synthesis Using a Commercially Available Nitroxide-mediated Radical Polymerization (NMP) Initiator."

For free radical systems, the kinetics of photopolymerization reactions are dependent on several variables such as monomer/oligomer concentration, monomer/oligomer functionality, viscosity of the system, light intensity, photoinitiator type and concentration, the presence of various additives (e.g., chain transfer agents, inhibitors), etc. Thus, for free radical photopolymerization the following steps typically describe the mechanism for formation of the photopolymer:

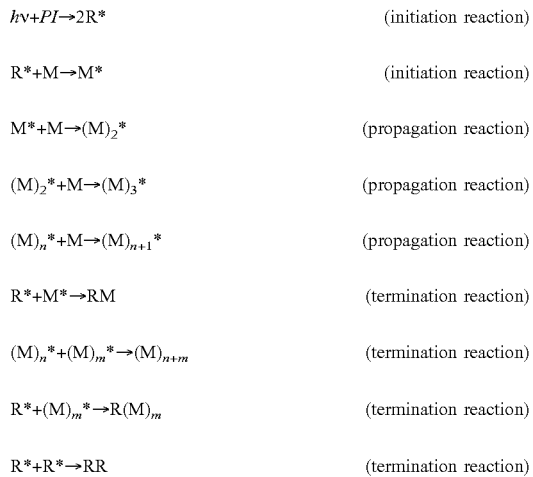

Computing the rates of photoinitiation and polymerization is known in the art, described for example in U.S. Pat. No. 7,704,643, incorporated herein by reference. The rate of initiation depends on the number of radicals generated by the photoinitiator (n=2 for many free radical initiators, n=1 for many cationic initiators), the quantum yield for initiation (typically less than 1), the intensity of absorbed light, incident light intensity, the concentration of photoinitiator, the molar absorptivity of the initiator at the wave length of interest, and the thickness of the system. The rate of polymerization depends on the kinetic rate constant for polymerization ($k_p$), the monomer concentration, and the kinetic rate constant for termination ($k_t$). In some embodiments, it is assumed that the light intensity does not vary appreciably through the medium. In some embodiments, the quantum efficiency of initiation for free radical photoinitiators is greatly affected by monomer concentration, viscosity, and rate of initiation when monomer concentration is below 0.1 M, which is in some embodiments the regime for a two-component type photopolymer holographic medium. Thus, in some embodiments, the following dependencies are found to decrease the quantum yield for initiation: higher viscosities, lower monomer concentration, and higher initiation rates (from increased intensity, higher molar absorptivity, etc.).

When a polymerization retarder/inhibitor Z—Y is added, the following additional steps can occur (where X* represents any radical):

Assuming that transfer to the retarder/inhibitor is high relative to other termination reactions, the rate of polymerization further depends on the concentration of the inhibitor and the rate constant of the termination with retarder/inhibitor ($k_z$). The polymerization rate is also further dependent on the $1^{st}$ power of the initiation rate. The ratio of $k_z/k_p$ is referred to as the inhibitor constant (e.g., lower case z). Values much greater than about 1 represent an inhibitory effect, whereas values of about 1 or less represent retarding effects. Values much less than about 1 represent little effect on the polymerization rate.

The difference between a polymerization inhibitor and a polymerization retarder frequently depends on the particular polymerizable component involved. For example, nitrobenzene only mildly retards radical polymerization of methyl acrylate, yet, nitrobenzene inhibits radical polymerization of vinyl acetate. Thus, it is possible to find agents that are typically considered as inhibitors that would also function as retarders for the purposes of the present disclosure. Inhibitor constants z for various polymerization retarders/inhibitors with various polymer systems are known in the art and described for example in U.S. Pat. No. 7,704,643, incorporated herein by reference.

Suitable polymerization retarders and inhibitors for use herein include but are not limited to one or more of the following: for free radical polymerizations, various phenols including butylated hydroxytoluenes (BHT) such as 2,6-di-t-butyl-p-cresol, p-methoxyphenol, diphenyl-p-benzoquinone, benzoquinone, hydroquinone, pyrogallol, resorcinol, phenanthraquinone, 2,5-toluquinone, benzylaminophenol, p-dihydroxybenzene, 2,4,6-trimethylphenol, etc.; various nitrobenzenes including o-dinitrobenzene, p-dinitrobenzene, m-dinitrobenzene, etc.; N-phenyl-1-naphthylamine, N-phenyl-2-naphthylamine, cupferron, phenothiazine, tannic acid, p-nitrosamine, chloranil, aniline, hindered anilines, ferric chloride, cupric chloride, triethylamine, etc. These polymerization retarders and inhibitors can be used individually (e.g., a single retarder) or in combinations of two or more, e.g., a plurality of retarders. The same principles can be applied to ionic polymerizations. For example, it is known that chloride anions can behave as retarders or inhibitors for cationic polymerizations, depending on both the monomer type and the concentration of the chloride anions. Typically, functionalities that are basic or mildly nucleophilic behave as retarders and inhibitors for cationic polymerizations; whereas for anionic polymerizations, slightly acidic and mildly electrophilic functionalities behave as retarders and inhibitors.

In some embodiments, polymerization reactions involving both polymerization retarders and inhibitors should lead to termination reactions. If reinitiation occurs to any appreciable degree, then the agent is typically considered a chain transfer agent. For example, triethylamine can be used as a chain transfer agent since it is also capable of reinitiating some radical polymerizations; however, when the reinitiation is slow compared to termination reactions, then even chain transfer agents can be considered potential polymerization retarders or inhibitors for the purposes of the present disclosure. Suitable chain transfer agents for use herein include but are not limited to: triethylamine, thioethers, compounds having carbonate groups, ethers, toluene derivatives, allyl ethers, etc. Chain transfer agents that are mildly retarding can be desirable because these can be incorporated into the matrix and enable attachment of the photopolymer and photoinitiator radicals to the matrix.

In some embodiments, after the first several exposures in recording multiple holograms, the amount of polymerization inhibitor present in the medium can be reduced. Conversely, with the use of a polymerization retarder, only small amounts of the retarder are reacted during any given exposure. Therefore, the concentration of the polymerization retarder can potentially decrease substantially linearly and in correlation to the reduction in monomer concentration. Thus, even late in the exposure schedule, there is enough retarder to prevent both polymerization after an exposure and polymerization in low light intensity areas. Effectively, the polymerization retarder serves as a chain length limiter. Ideally, the ratio of polymerization retarder to polymerizable material (e.g., monomer) stays nearly constant throughout the exposure schedule. In such a scenario, the chain length (degree of polymerization), potentially, stays essentially the same throughout the exposure schedule, leading to a substantially linear response for number of exposures versus time period for each exposure. The use of retarders/inhibitors/chain transfer agents is not limited to radical polymerizations, and is applicable as well to ionic chain polymerizations.

In addition to retarders, inhibitors and/or chain transfer agents, metastable reactive centers and light labile phototerminators can also be used to control polymerization reactions described herein of the appropriate reactivity. For example, nitroxyl radicals can be added as a metastable reactive center. Nitroxyl radicals create pseudo-living radical polymerizations with certain monomers. Thus, the nitroxyl radical initially behaves as a terminating agent (such as an inhibitor), however, depending on the temperature at which the polymerization is carried out, the termination is reversible. In such scenarios, chain length can be controlled by changing the recording temperature. Thus, it is possible to record holograms at an elevated temperature and then cool to room temperature to prevent further polymerizations. Additionally, it is possible to record at room temperature, thus terminating all chains quickly like an inhibitor, and then to heat the sample to enable the addition of new photoactive monomer to all the gratings at the same time. In this other scenario, there is an advantage gained from the polymerization of all gratings occurring at a single time in that Bragg detuning would be uniform for all gratings involved. Other potential metastable reactive center include triphenylmethyl radicals, dithioesters are typically used in Reversible Addition-Fragmentation chain Transfer (RAFT) polymerizations, that can behave as appropriate metastable reactive centers, etc. As for ionic polymerizations, there are stable ions that are able to perform the same function, as the example nitroxyl radicals above.

Use of a light labile phototerminator provides the ability to control the activity of the reactive species with light (as opposed to heat as described above). A light labile phototerminator is any molecule capable of undergoing reversible termination reactions using a light source. For example, certain cobaltoxime complexes can be used to photoinitiate radical polymerizations, and yet, also terminate the same radical polymerizations. Dithioesters are also suitable as light labile phototerminators because they have the ability to reversibly form radicals with appropriate wavelengths of light. Under the appropriate conditions and with appropriate monomers (such as styrenes and acrylates), it is possible to restart the polymerization by irradiating with a photoinitiating light source (e.g., recording light). Thus, as long as a given volume is exposed to a photoinitiating light source, radical polymerization continues, whereas when the photoinitiating light is off or absent, the polymerizations are terminated. Metastable reactive centers and light labile phototerminators can also be used to control ionic (e.g., cationic or anionic initiated) polymerization reaction systems according to the present disclosure.

For ionic chain reactions (e.g., cationic and anionic initiated polymerization reactions), counter ion and solvent effects can be used to control polymerization by terminating the reactive center. Ionic systems are sensitive to solvent conditions because the solvent (or the support matrix) determines the proximity of the counter ion to the reactive center. For instance, in a nonpolar medium the counter ion will be very closely associated with the reactive center; in a polar medium the counter ion may become freely dissociated. The proximity of the counter ion can determine polymerization rate as well as the potential for collapse with the counter ion (depending on the counter ion used). For example, if one uses a cationic polymerization with a nonpolar support matrix and chloride anion as the counter ion, there is a better probability of terminating the reaction due to collapse of the counter ion. Thus, in this way, ionic polymerizations can be terminated in a controlled manner, since choice of support matrix and counter ions allows one to determine the likelihood of collapse versus the probability of propagation.

Certain monomer mixtures can also behave in a manner that can control the degree or rate of polymerization. For example, if a small amount of alpha methyl styrene is present in an acrylate polymerization, the acrylate will add into the alpha methyl styrene and the styrene will not substantially reinitiate polymerization of the acrylate, e.g., the alpha methyl styrene retards the rate of acrylate polymerization. Additionally, the alpha methyl styrene is slow to polymerize with itself, and thus behaves as a polymerization retarder/inhibitor even though it is a comonomer. In the case of ionic polymerizations; using, for example, vinyl anisole in a cationic vinyl ether polymerization results in retarded rates of polymerization because the vinyl anisole does not efficiently reinitiate vinyl ether polymerization.

Volume Holograms, Photosensitive Polymers, and Devices Thereof

In some embodiments, the present disclosure relates to recording materials for volume holograms, where the recording material is characterized by a thickness and includes one or more compounds described herein. In some embodiments, the disclosure provides a resin mixture including a first polymer precursor including a compound of Formula I, Formula I(a), Formula II, Formula II(a), Formula II(b), Formula II(c), Formula II(d), Formula II(e), Formula II(f), Formula II(g), Formula II(h), Formula II(i), Formula II(j), Formula III, Formula III(a), or Formula III(b), having any and all corresponding limitations described herein, and a second polymer precursor including a different compound including a polymerizable or crosslinkable group. In some embodiments, the different compound is selected from an alcohol and an isocyanate described herein.

The disclosure also provides a polymeric material including a resin mixture including a first polymer precursor including a compound of Formula I, Formula I(a), Formula II, Formula II(a), Formula II(b), Formula II(c), Formula II(d), Formula II(e), Formula II(f), Formula II(g), Formula II(h), Formula II(i), Formula II(j), Formula III, Formula III(a), or Formula III(b), having any and all corresponding limitations described herein, and a second polymer precursor including a different compound including a polymerizable or crosslinkable group, wherein the second polymer precursor is partially or totally polymerized or crosslinked. In some embodiments, the different compound is selected from an alcohol and an isocyanate described herein. In some embodiments, the first polymer precursor is partially or totally polymerized or crosslinked.

The disclosure also provides a recording material for writing a volume Bragg grating, the material including a transparent support and a resin mixture including a first polymer precursor including a compound of Formula I, Formula I(a), Formula II, Formula (a), Formula II(b), Formula II(c), Formula II(d), Formula II(e), Formula II(f), Formula (g), Formula II(h), Formula II(i), Formula II(j), Formula III, Formula III(a), or Formula III(b), having any and all corresponding limitations described herein, and a second polymer precursor including a different compound including a polymerizable or crosslinkable group. In some embodiments, the different compound is selected from an alcohol and an isocyanate described herein. In some embodiments, the material has a thickness of between 1 μm and 500 μm.

The disclosure also provides a recording material for writing a volume Bragg grating, the material including a polymeric material including a resin mixture including a first polymer precursor including a compound of Formula I, Formula I(a), Formula II, Formula (a), Formula II(b), Formula II(c), Formula II(d), Formula II(e), Formula II(f), Formula (g), Formula II(h), Formula II(i), Formula II(j), Formula III, Formula III(a), or Formula III(b), having any and all corresponding limitations described herein, and a second polymer precursor including a different compound including a polymerizable or crosslinkable group, wherein the second polymer precursor is partially or totally polymerized or crosslinked. In some embodiments, the different compound is selected from an alcohol and an isocyanate described herein. In some embodiments, the first polymer precursor is partially or totally polymerized or crosslinked. In some embodiments, the material has a thickness of between 1 μm and 500 μm.

The disclosure also provides a volume Bragg grating recorded on any recording material described herein, the grating characterized by a Q parameter equal to or greater than 5, wherein $$Q = \frac{2\pi\lambda_0 d}{n_0 \Lambda^2},$$

and wherein $\lambda_0$ is a recording wavelength, d is the thickness of the recording material, $n_0$ is a refractive index of the recording material, and $\Lambda$ is a grating constant. In some embodiments, the Q parameter is equal to or greater than 1. In some embodiments, the Q parameter is equal to or greater than 2. In some embodiments, the Q parameter is equal to or greater than 3. In some embodiments, the Q parameter is equal to or greater than 4. In some embodiments, the Q parameter is equal to or greater than 5. In some embodiments, the Q parameter is equal to or greater than 6. In some embodiments, the Q parameter is equal to or greater than 7. In some embodiments, the Q parameter is equal to or greater than 8. In some embodiments, the Q parameter is equal to or greater than 9. In some embodiments, the Q parameter is equal to or greater than 10. In some embodiments, the Q parameter is equal to or greater than 11. In some embodiments, the Q parameter is equal to or greater than 12. In some embodiments, the Q parameter is equal to or greater than 13. In some embodiments, the Q parameter is equal to or greater than 14. In some embodiments, the Q parameter is equal to or greater than 15.

The following clauses describe certain embodiments.

Clause 49: a resin mixture comprising a first polymer precursor comprising the compound of any one of clauses 1 to 48, and a second polymer precursor comprising a different compound comprising a polymerizable or crosslinkable group.

Clause 50: the resin mix of clause 49, wherein the different compound is selected from an alcohol and an isocyanate.

Clause 51: a polymeric material comprising the resin mix of clause 49 or clause 50, wherein the second polymer precursor is partially or totally polymerized or crosslinked.

Clause 52: the polymeric material of clause 51, wherein the first polymer precursor is partially or totally polymerized or crosslinked.

Clause 53: a recording material for writing a volume Bragg grating, the material comprising a transparent support and at least one of: the resin mix of clause 49, the resin mix of clause 50, the polymeric material of clause 51, or the polymeric material of clause 52.

Clause 54: the recording material of clause 53, wherein the material has a thickness of between 1 μm and 500 μm.

Clause 55: a volume Bragg grating recorded on the recording material of clause 53 or clause 54, wherein the grating is characterized by a Q parameter equal to or greater than 5, wherein $$Q = \frac{2\pi\lambda_0 d}{n_0 \Lambda^2}$$

and wherein $\lambda_0$ is a recording wavelength, d is the thickness of the recording material, $n_0$ is a refractive index of the recording material, and $\Lambda$ is a grating constant.

Clause 56: the volume Bragg grating of clause 55, characterized by a Q parameter equal to or greater than 5.

Clause 57: the volume Bragg grating of clause 55, characterized by a Q parameter equal to or greater than 10.

Figures 5A, 5B:
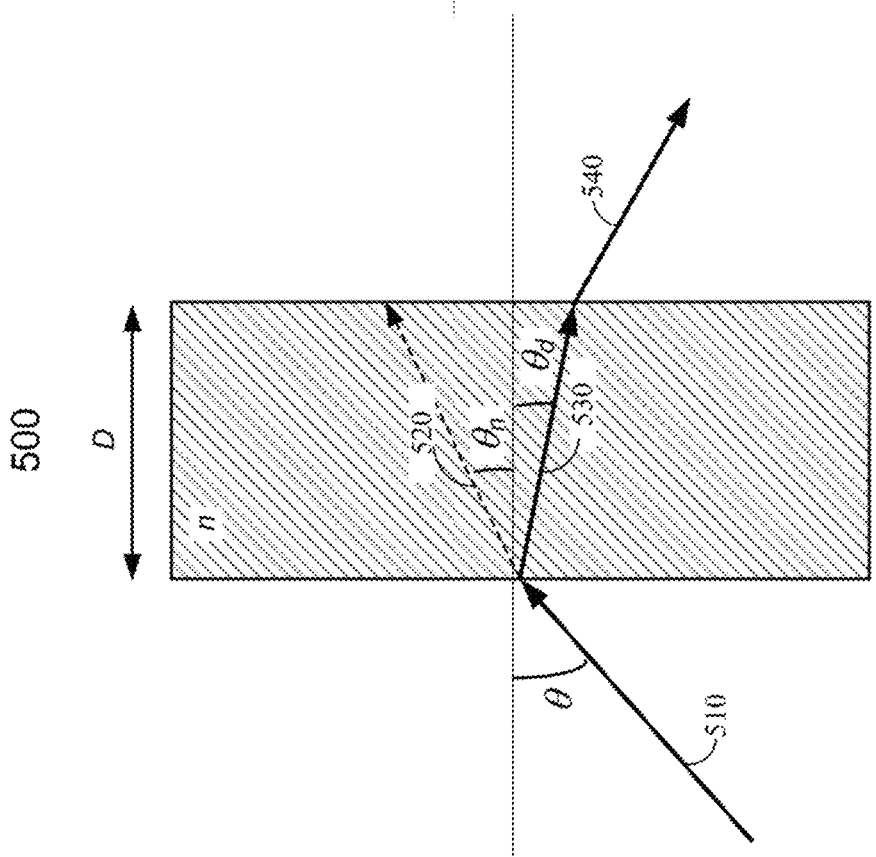
FIG. 5A illustrates an example of a volume Bragg grating.
FIG. 5B illustrates the Bragg condition for the volume Bragg grating shown in FIG. 5A.

In some embodiments, a volume Bragg grating may be recorded on any holographic material layer described herein, by exposing the holographic material layer to light patterns generated by the interference between two or more coherent light beams. FIG. 5A illustrates an example of a volume Bragg grating (VBG) 500. Volume Bragg grating 500 shown in FIG. 5A may include a transmission holographic grating that has a thickness D. The refractive index n of volume Bragg grating 500 may be modulated at an amplitude $n_1$, and the grating period of volume Bragg grating 500 may be $\Lambda$. Incident light 510 having a wavelength $\lambda$ may be incident on volume Bragg grating 500 at an incident angle θ, and may be refracted into volume Bragg grating 500 as incident light 520 that propagates at an angle $\theta_n$ in volume Bragg grating 500. Incident light 520 may be diffracted by volume Bragg grating 500 into diffraction light 530, which may propagate at a diffraction angle $\theta_d$ in volume Bragg grating 500 and may be refracted out of volume Bragg grating 500 as diffraction light 540.

FIG. 5B illustrates the Bragg condition for volume Bragg grating 500 shown in FIG. 5A. Vector 505 represents the grating vector $\vec{G}$, where $|\vec{G}|=2\pi/\Lambda$. Vector 525 represents the incident wave vector $\vec{k}_I$, and vector 535 represents the diffract wave vector $\vec{k}_d$, where $|\vec{k}_I|=|\vec{k}_d|=2\pi n/\lambda$. Under the Bragg phase-matching condition, $\vec{k}_I-\vec{k}_d=\vec{G}$. Thus, for a given wavelength $\lambda$, there may only be one pair of incident angle $\theta$ (or $\theta_n$) and diffraction angle $\theta_d$ that meet the Bragg condition perfectly. Similarly, for a given incident angle $\theta$, there may only be one wavelength $\lambda$ that meets the Bragg condition perfectly. As such, the diffraction may only occur in a small wavelength range and a small incident angle range. The diffraction efficiency, the wavelength selectivity, and the angular selectivity of volume Bragg grating 500 may be functions of thickness D of volume Bragg grating 500. For example, the full-width-half-magnitude (FWHM) wavelength range and the FWHM angle range of volume Bragg grating 500 at the Bragg condition may be inversely proportional to thickness D of volume Bragg grating 500, while the maximum diffraction efficiency at the Bragg condition may be a function $\sin^2(a \times n_1 \times D)$, where a is a coefficient. For a reflection volume Bragg grating, the maximum diffraction efficiency at the Bragg condition may be a function of tan $h^2(a \times n_1 \times D)$.

In some embodiments, a multiplexed Bragg grating may be used to achieve a desired optical performance, such as a high diffraction efficiency and large FOV for the full visible spectrum (e.g., from about 400 nm to about 700 nm, or from about 440 nm to about 650 nm). Each part of the multiplexed Bragg grating may be used to diffract light from a respective FOV range and/or within a respective wavelength range. Thus, in some designs, multiple volume Bragg gratings each recorded under a respective recording condition may be used.

The holographic optical elements described herein may be recorded in a holographic material (e.g., photopolymer) layer. In some embodiments, the HOEs can be recorded first and then laminated on a substrate in a near-eye display system. In some embodiments, a holographic material layer may be coated or laminated on the substrate and the HOES may then be recorded in the holographic material layer.

In general, to record a holographic optical element in a photosensitive material layer, two coherent beams may interfere with each other at certain angles to generate a unique interference pattern in the photosensitive material layer, which may in turn generate a unique refractive index modulation pattern in the photosensitive material layer, where the refractive index modulation pattern may correspond to the light intensity pattern of the interference pattern. The photosensitive material layer may include, for example, silver halide emulsion, dichromated gelatin, photopolymers including photo-polymerizable monomers suspended in a polymer matrix, photorefractive crystals, and the like. FIG. 6A illustrates the recording light beams for recording a volume Bragg grating 600 and the light beam reconstructed from volume Bragg grating 600 according to certain embodiments. In the example illustrated, volume Bragg grating 600 may include a transmission volume hologram recorded using a reference beam 620 and an object beam 610 at a first wavelength, such as 660 nm. When a light beam 630 at a second wavelength (e.g., 940 nm) is incident on volume Bragg grating 600 at a 0° incident angle, the incident light beam 630 may be diffracted by volume Bragg grating 600 at a diffraction angle as shown by a diffracted beam 640.

Figure 6B:
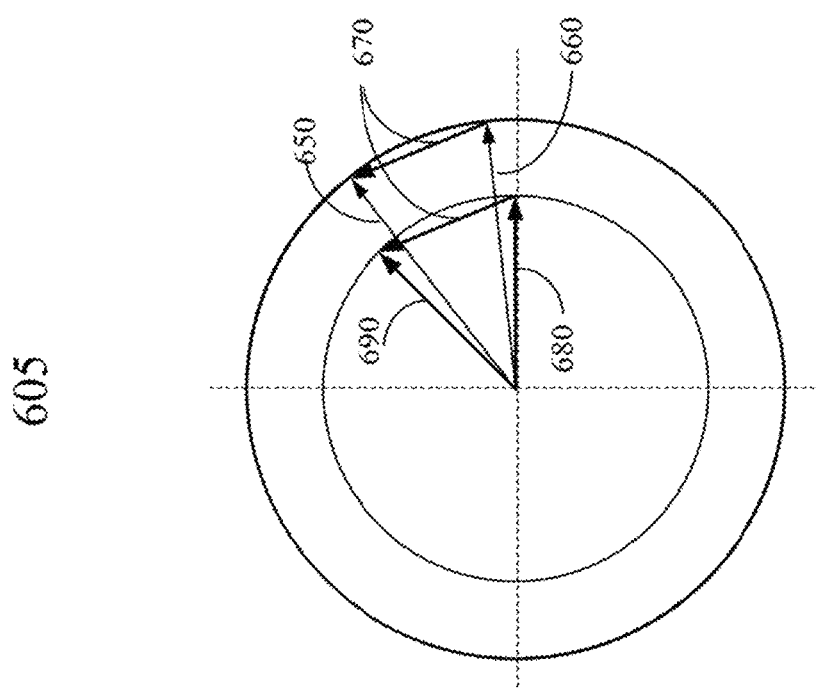
FIG. 6B is an example of a holography momentum diagram illustrating the wave vectors of recording beams and reconstruction beams and the grating vector of the recorded volume Bragg grating according to certain embodiments.
Figure 6A:
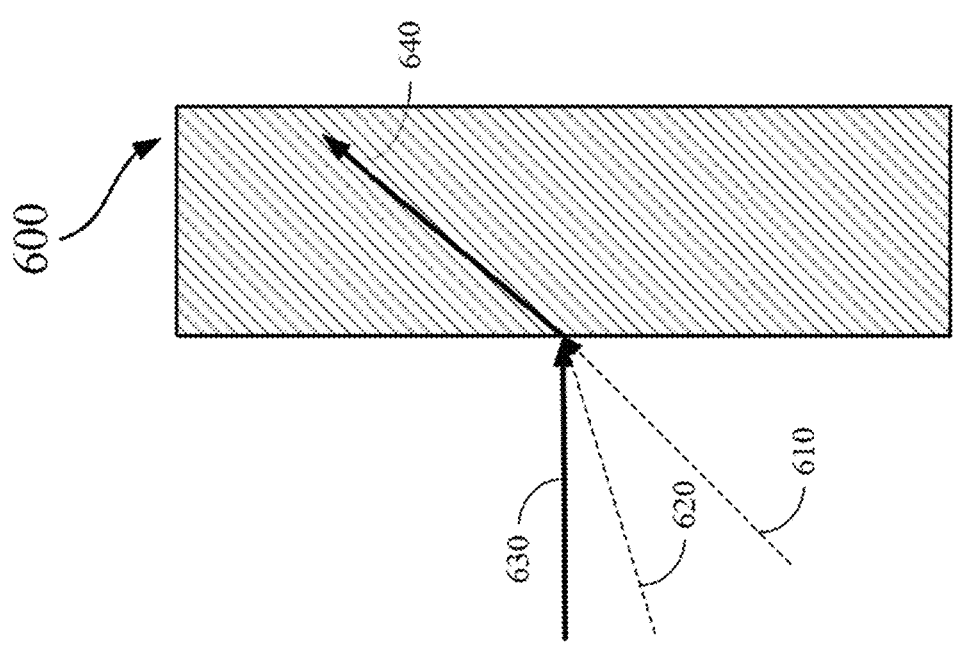
FIG. 6A illustrates the recording light beams for recording a volume Bragg grating according to certain embodiments.

FIG. 6B is an example of a holography momentum diagram 605 illustrating the wave vectors of recording beams and reconstruction beams and the grating vector of the recorded volume Bragg grating according to certain embodiments. FIG. 6B shows the Bragg matching conditions during the holographic grating recording and reconstruction. The length of wave vectors 650 and 660 of the recording beams (e.g., object beam 610 and reference beam 620) may be determined based on the recording light wavelength $\lambda_c$ (e.g., 660 nm) according to $2\pi n/\lambda_c$, where n is the average refractive index of holographic material layer. The directions of wave vectors 650 and 660 of the recording beams may be determined based on the desired grating vector K (670) such that wave vectors 650 and 660 and grating vector K (670) can form an isosceles triangle as shown in FIG. 6B. Grating vector K may have an amplitude $2\pi/\Lambda$, where $\Lambda$ is the grating period. Grating vector K may in turn be determined based on the desired reconstruction condition. For example, based on the desired reconstruction wavelength $\lambda_r$ (e.g., 940 nm) and the directions of the incident light beam (e.g., light beam 630 at 0°) and the diffracted light beam (e.g., diffracted beam 640), grating vector K (670) of volume Bragg grating 600 may be determined based on the Bragg condition, where wave vector 680 of the incident light beam (e.g., light beam 630) and wave vector 690 of the diffracted light beam (e.g., diffracted beam 640) may have an amplitude $2\pi n/\lambda_r$, and may form an isosceles triangle with grating vector K (670) as shown in FIG. 6B.

As described herein, for a given wavelength, there may only be one pair of incident angle and diffraction angle that meets the Bragg condition perfectly. Similarly, for a given incident angle, there may only be one wavelength that meets the Bragg condition perfectly. When the incident angle of the reconstruction light beam is different from the incident angle that meets the Bragg condition of the volume Bragg grating or when the wavelength of the reconstruction light beam is different from the wavelength that meets the Bragg condition of the volume Bragg grating, the diffraction efficiency may be reduced as a function of the Bragg mismatch factor caused by the angular or wavelength detuning from the Bragg condition. As such, the diffraction may only occur in a small wavelength range and a small incident angle range.

Figure 7:
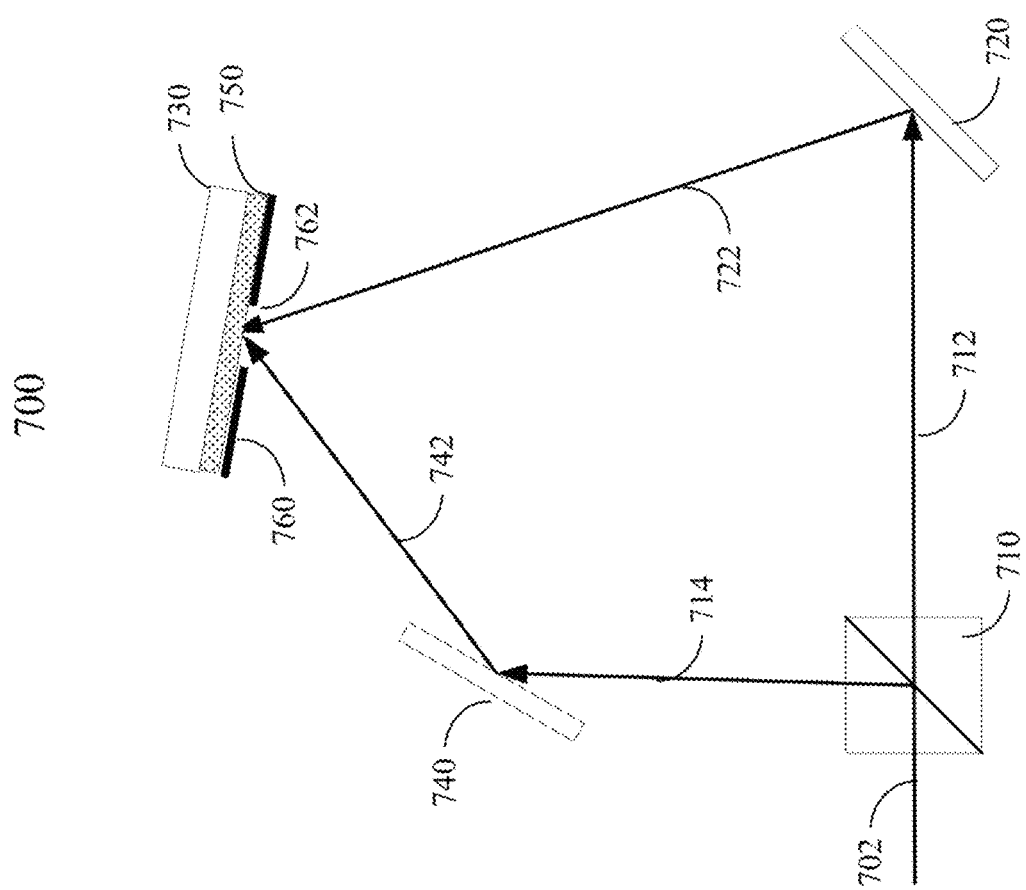
FIG. 7 illustrates an example of a holographic recording system for recording holographic optical elements according to certain embodiments.

FIG. 7 illustrates an example of a holographic recording system 700 for recording holographic optical elements according to certain embodiments. Holographic recording system 700 includes a beam splitter 710 (e.g., a beam splitter cube), which may split an incident laser beam 702 into two light beams 712 and 714 that are coherent and may have similar intensities. Light beam 712 may be reflected by a first mirror 720 towards a plate 730 as shown by the reflected light beam 722. On another path, light beam 714 may be reflected by a second mirror 740. The reflected light beam 742 may be directed towards plate 730, and may interfere with light beam 722 at plate 730 to generate an interference pattern. A holographic recording material layer 750 may be formed on plate 730 or on a substrate mounted on plate 730. The interference pattern may cause the holographic optical element to be recorded in holographic recording material layer 750 as described above. In some embodiments, plate 730 may also be a mirror.

In some embodiments, a mask 760 may be used to record different HOEs at different regions of holographic recording material layer 750. For example, mask 760 may include an aperture 762 for the holographic recording and may be moved to place aperture 762 at different regions on holographic recording material layer 750 to record different HOEs at the different regions using different recording conditions (e.g., recording beams with different angles).

Holographic materials can be selected for specific applications based on some parameters of the holographic materials, such as the spatial frequency response, dynamic range, photosensitivity, physical dimensions, mechanical properties, wavelength sensitivity, and development or bleaching method for the holographic material.

The dynamic range indicates how much refractive index change can be achieved in a holographic material. The dynamic range may affect, for example, the thickness of the device for high efficiency and the number of holograms that can be multiplexed in the holographic material. The dynamic range may be represented by the refractive index modulation (RIM), which may be one half of the total change in refractive index. Small values of refractive index modulation may be given as parts per million (ppm). In generally, a large refractive index modulation in the holographic optical elements is desired in order to improve the diffraction efficiency and record multiple holographic optical elements in a same holographic material layer.

The frequency response is a measure of the feature size that the holographic material can record and may dictate the types of Bragg conditions that can be achieved. The frequency response can be characterized by a modulation transfer function, which may be a curve depicting the sinusoidal waves of varying frequencies. In general, a single frequency value may be used to represent the frequency response, which may indicate the frequency value at which the refractive index modulation begins to drop or at which the refractive index modulation is reduced by 3 dB. The frequency response may also be represented by lines/mm, line pairs/mm, or the period of the sinusoid.

The photosensitivity of the holographic material may indicate the photo-dosage required to achieve a certain efficiency, such as 100% or 1% (e.g., for photo-refractive crystals). The physical dimensions that can be achieved in a particular holographic material affect the aperture size as well as the spectral selectivity of the HOE device. Physical parameters of holographic materials may be related to damage thresholds and environmental stability. The wavelength sensitivity may be used to select the light source for the recording setup and may also affect the minimum achievable period. Some materials may be sensitive to light in a wide wavelength range. Development considerations may include how the holographic material is processed after recording. Many holographic materials may need post-exposure development or bleaching.

Embodiments of the invention may be used to fabricate components of an artificial reality system or may be implemented in conjunction with an artificial reality system. Artificial reality is a form of reality that has been adjusted in some manner before presentation to a user, which may include, for example, a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, for example, create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

Figure 4:
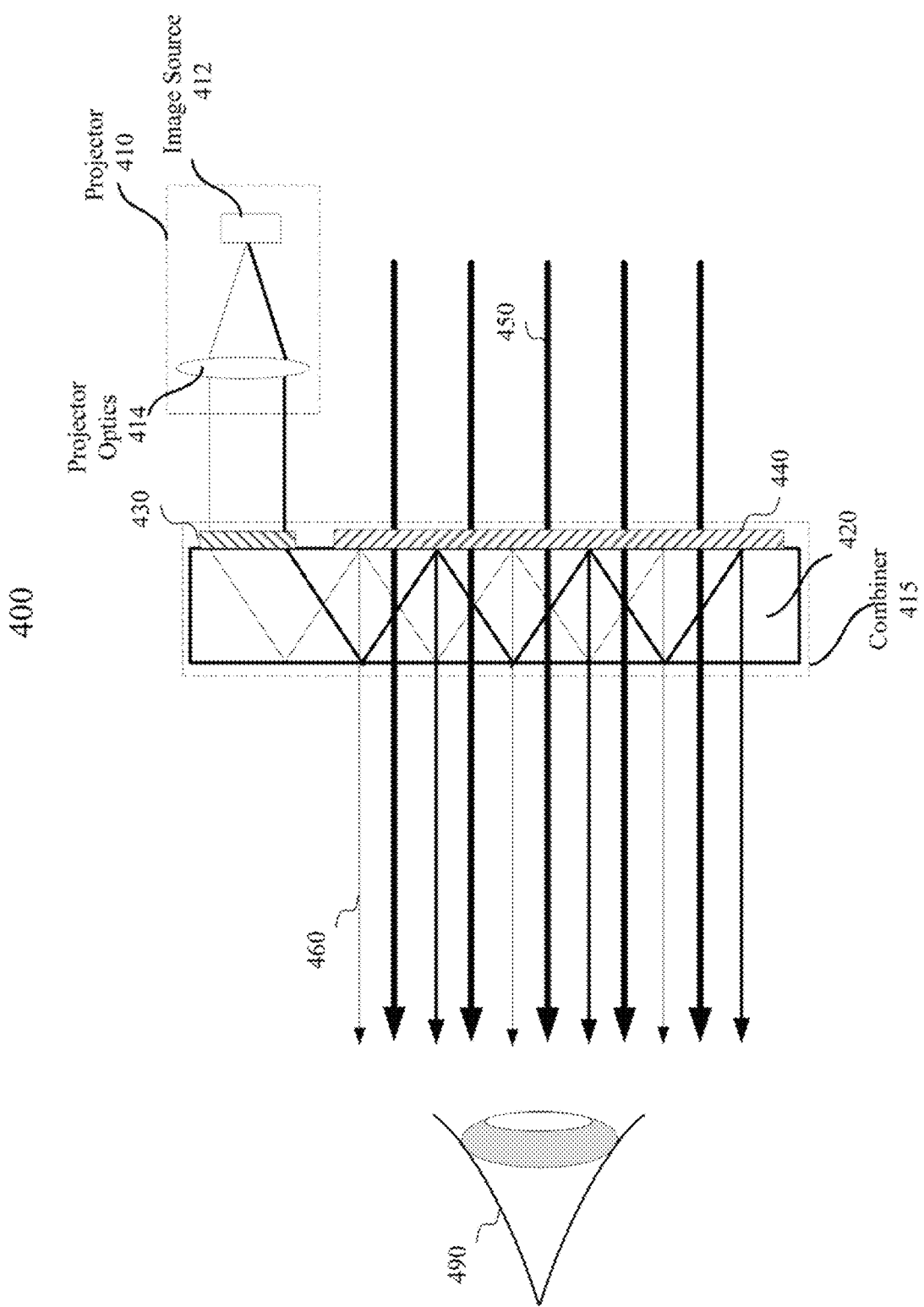
FIG. 4 illustrates an example of an optical see-through augmented reality system using a waveguide display that includes an optical combiner according to certain embodiments.

FIG. 4 illustrates an example of an optical see-through augmented reality system 400 using a waveguide display according to certain embodiments. Augmented reality system 400 may include a projector 410 and a combiner 415. Projector 410 may include a light source or image source 412 and projector optics 414. In some embodiments, image source 412 may include a plurality of pixels that displays virtual objects, such as an LCD display panel or an LED display panel. In some embodiments, image source 412 may include a light source that generates coherent or partially coherent light. For example, image source 412 may include a laser diode, a vertical cavity surface emitting laser, and/or a light emitting diode. In some embodiments, image source 412 may include a plurality of light sources each emitting a monochromatic image light corresponding to a primary color (e.g., red, green, or blue). In some embodiments, image source 412 may include an optical pattern generator, such as a spatial light modulator. Projector optics 414 may include one or more optical components that can condition the light from image source 412, such as expanding, collimating, scanning, or projecting light from image source 412 to combiner 415. The one or more optical components may include, for example, one or more lenses, liquid lenses, mirrors, apertures, and/or gratings. In some embodiments, projector optics 414 may include a liquid lens (e.g., a liquid crystal lens) with a plurality of electrodes that allows scanning of the light from image source 412.

Combiner 415 may include an input coupler 430 for coupling light from projector 410 into a substrate 420 of combiner 415. Combiner 415 may transmit at least 50% of light in a first wavelength range and reflect at least 25% of light in a second wavelength range. For example, the first wavelength range may be visible light from about 400 nm to about 650 nm, and the second wavelength range may be in the infrared band, for example, from about 800 nm to about 1000 nm. Input coupler 430 may include a volume holographic grating, a diffractive optical elements (DOE) (e.g., a surface-relief grating), a slanted surface of substrate 420, or a refractive coupler (e.g., a wedge or a prism). Input coupler 430 may have a coupling efficiency of greater than 30%, 50%, 75%, 90%, or higher for visible light. Light coupled into substrate 420 may propagate within substrate 420 through, for example, total internal reflection (TIR). Substrate 420 may be in the form of a lens of a pair of eyeglasses. Substrate 420 may have a flat or a curved surface, and may include one or more types of dielectric materials, such as glass, quartz, plastic, polymer, poly(methyl methacrylate) (PMMA), crystal, or ceramic. A thickness of the substrate may range from, for example, less than about 1 mm to about 10 mm or more. Substrate 420 may be transparent to visible light.

Substrate 420 may include or may be coupled to a plurality of output couplers 440 configured to extract at least a portion of the light guided by and propagating within substrate 420 from substrate 420, and direct extracted light 460 to an eye 490 of the user of augmented reality system 400. As input coupler 430, output couplers 440 may include grating couplers (e.g., volume holographic gratings or surface-relief gratings), other DOEs, prisms, etc. Output couplers 440 may have different coupling (e.g., diffraction) efficiencies at different locations. Substrate 420 may also allow light 450 from environment in front of combiner 415 to pass through with little or no loss. Output couplers 440 may also allow light 450 to pass through with little loss. For example, in some implementations, output couplers 440 may have a low diffraction efficiency for light 450 such that light 450 may be refracted or otherwise pass through output couplers 440 with little loss, and thus may have a higher intensity than extracted light 460. In some implementations, output couplers 440 may have a high diffraction efficiency for light 450 and may diffract light 450 to certain desired directions (i.e., diffraction angles) with little loss. As a result, the user may be able to view combined images of the environment in front of combiner 415 and virtual objects projected by projector 410.

While preferred embodiments are shown and described herein, such embodiments are provided by way of example only and are not intended to otherwise limit the scope of the disclosure. Various alternatives to the described embodiments may be employed in practicing the disclosure.

A number of patent and non-patent publications are cited herein in order to describe the state of the art to which this disclosure pertains. The entire disclosure of each of these publications is incorporated by reference herein.

While certain embodiments are described and/or exemplified herein, various other embodiments will be apparent to those skilled in the art from the disclosure. The present disclosure is, therefore, not limited to the particular embodiments described and/or exemplified, but is capable of considerable variation and modification without departure from the scope and spirit of the appended claims.

EXAMPLES

Example 1: DE Increase and Haze Reduction

Figure 8:
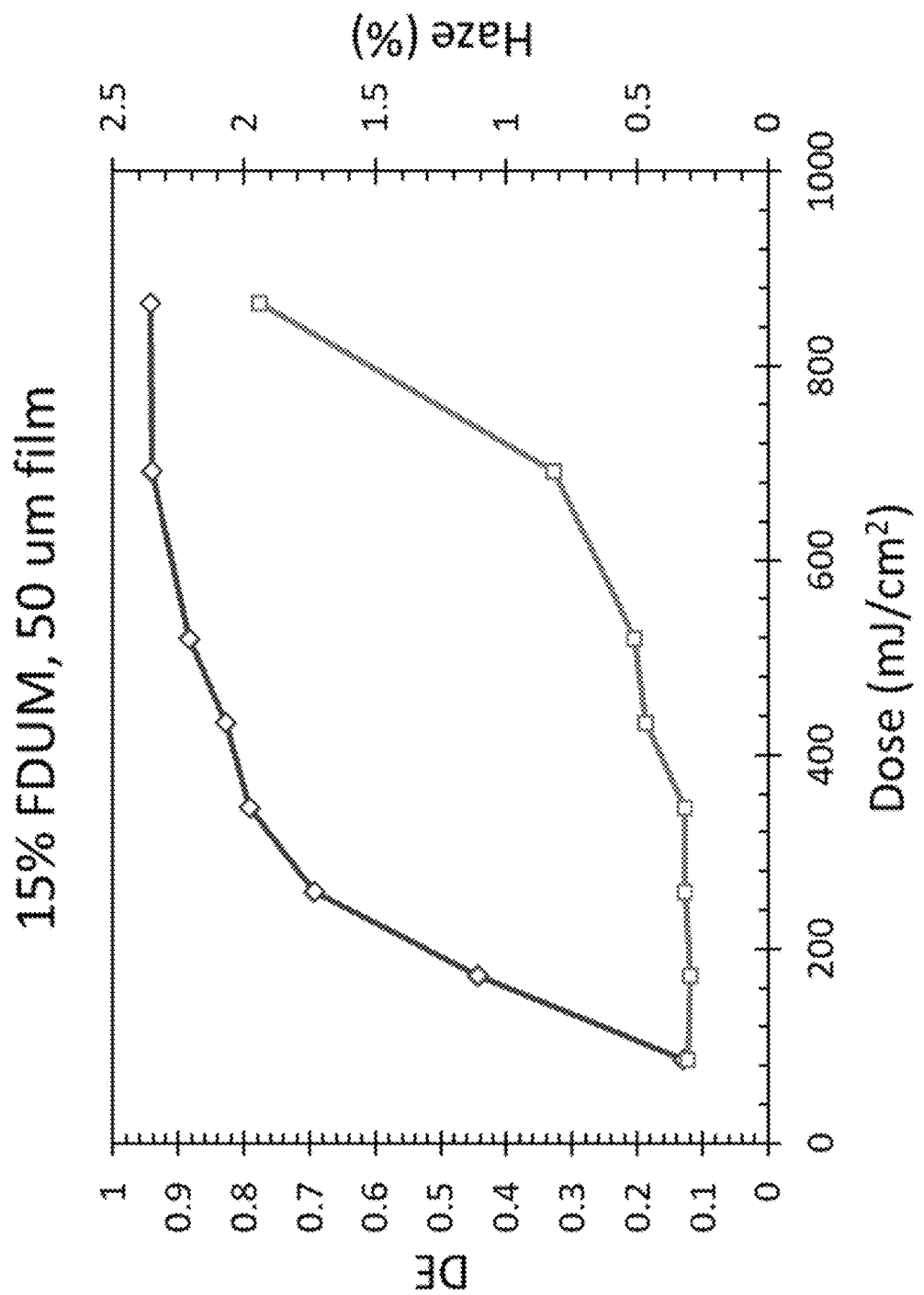
FIG. 8 illustrates diffraction efficiency (DE) and Haze (%) as a function of exposure dose (mJ/cm$^2$) for compound of Formula III (FDUM; experimental conditions: exposure wavelength: 460 nm; reflection-type recording (single beam); film thickness: 50 μm; monomer loading: 15 wt %) according to certain embodiments.
Figure 9:
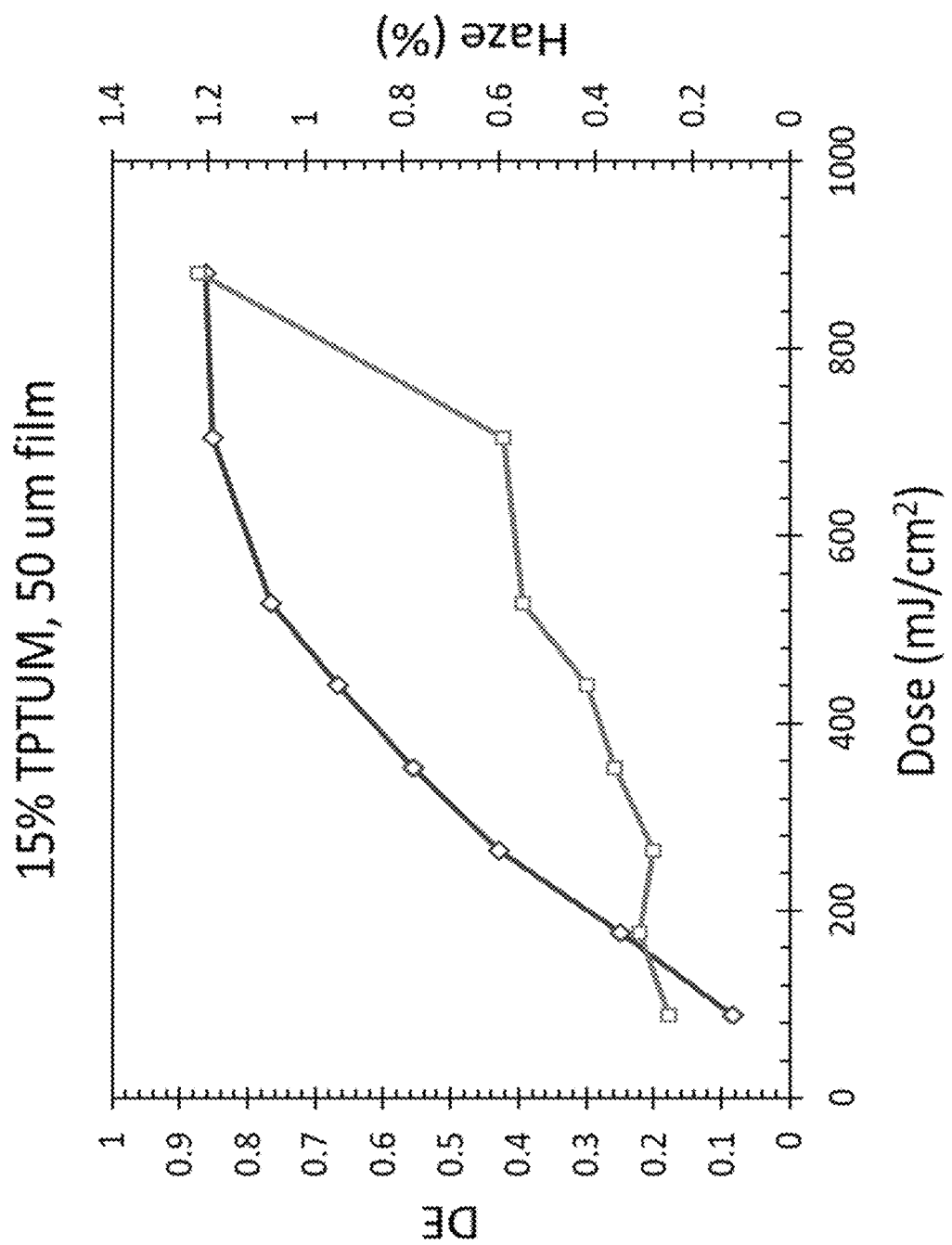
FIG. 9 illustrates DE and Haze (%) as a function of exposure dose (mJ/cm$^2$) for comparative compound TPTUM (experimental conditions: exposure wavelength: 460 nm; reflection-type recording (single beam); film thickness: 50 μm; monomer loading: 15 wt %) according to certain embodiments.

As shown in FIGS. 8 and 9, DE is increased and haze is reduced by using a cardofluorene bisurethane methacrylate compound of Formula III (FDUM):

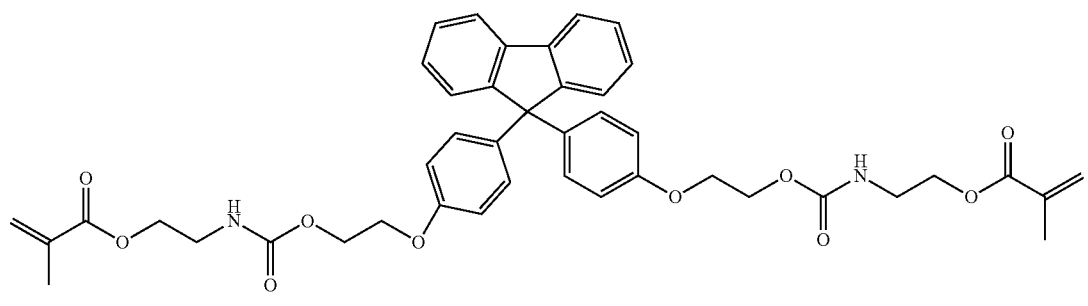

FDUM comparative to known compound TPTUM:

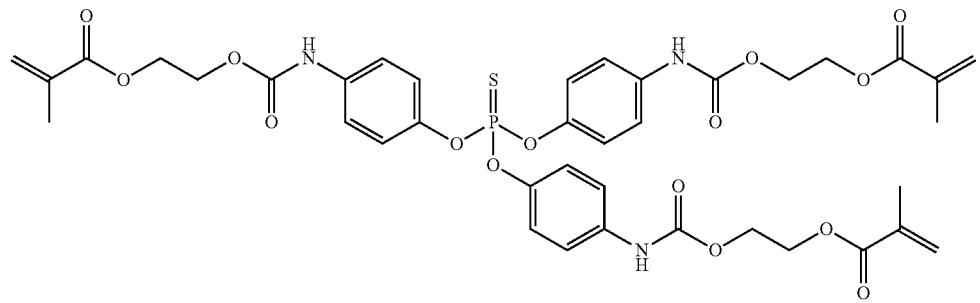

TPTUM

FIG. 8 illustrates DE and Haze (%) as a function of exposure dose (mJ/cm$^2$) for compound of Formula III (FDUM; experimental conditions: exposure wavelength: 460 nm; reflection-type recording (single beam); film thickness: 50 μm; monomer loading: 15 wt/o). FIG. 9 illustrates DE and Haze (%) as a function of exposure dose (mJ/cm$^2$) for comparative compound TPTUM (experimental conditions: exposure wavelength: 460 nm; reflection-type recording (single beam); film thickness: 50 μm; monomer loading: 15 wt %).

Example 2: Synthesis of 4-(9-(4-methoxyphenyl)-9H-fluoren-9-yl)phenol

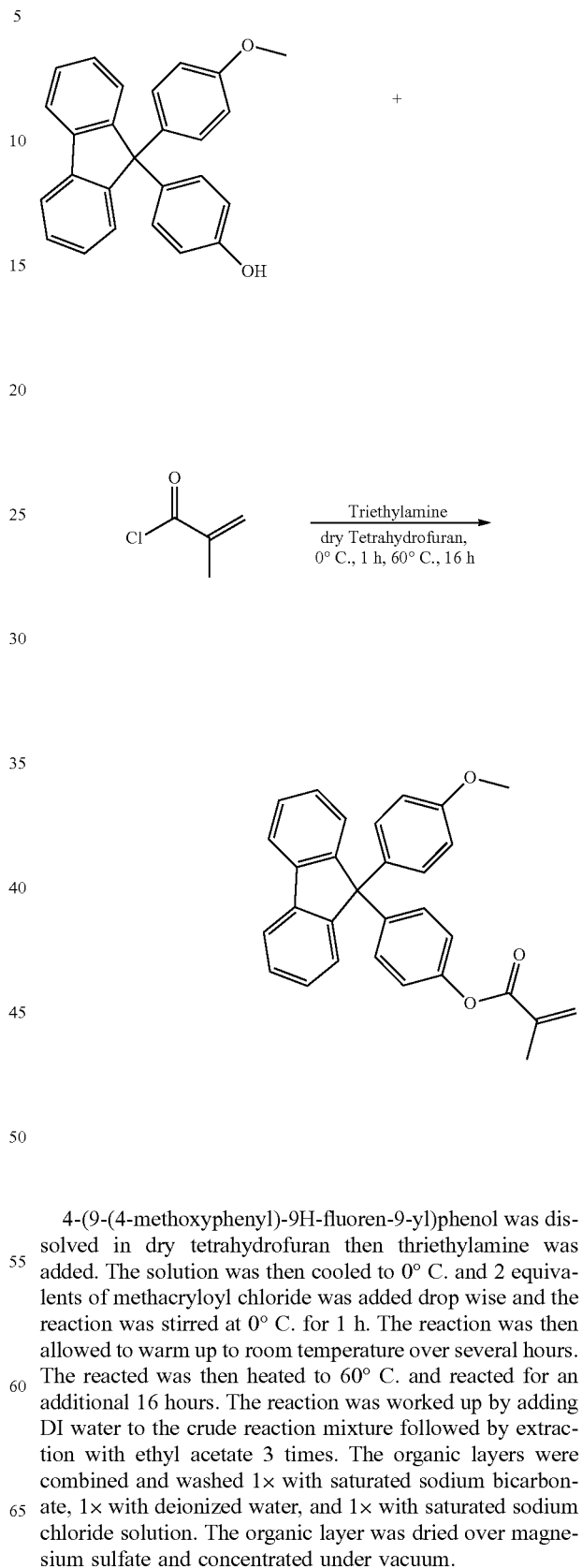

4,4'-(9H-fluorene-9,9-diyl)diphenol was dissolved in tetrahydrofuran then 1 equivalents of triethylamine was added. 1 equivalent of iodomethane was slowly added to the solution at room temperature to control the potential exotherm. The solution was the heated to 60° C. and left to react overnight. The reaction was worked up by adding water to the crude reaction mixture followed by extraction with ethyl acetate 3 times. The organic layers were combined and washed 1× with saturated sodium bicarbonate, 1× with deionized water, and 1× with saturated sodium chloride solution. The organic layer was dried over magnesium sulfate and concentrated under vacuum.

Example 3: Synthesis of 4-(9-(4-methoxyphenyl)-9H-fluoren-9-yl)phenyl Methacrylate

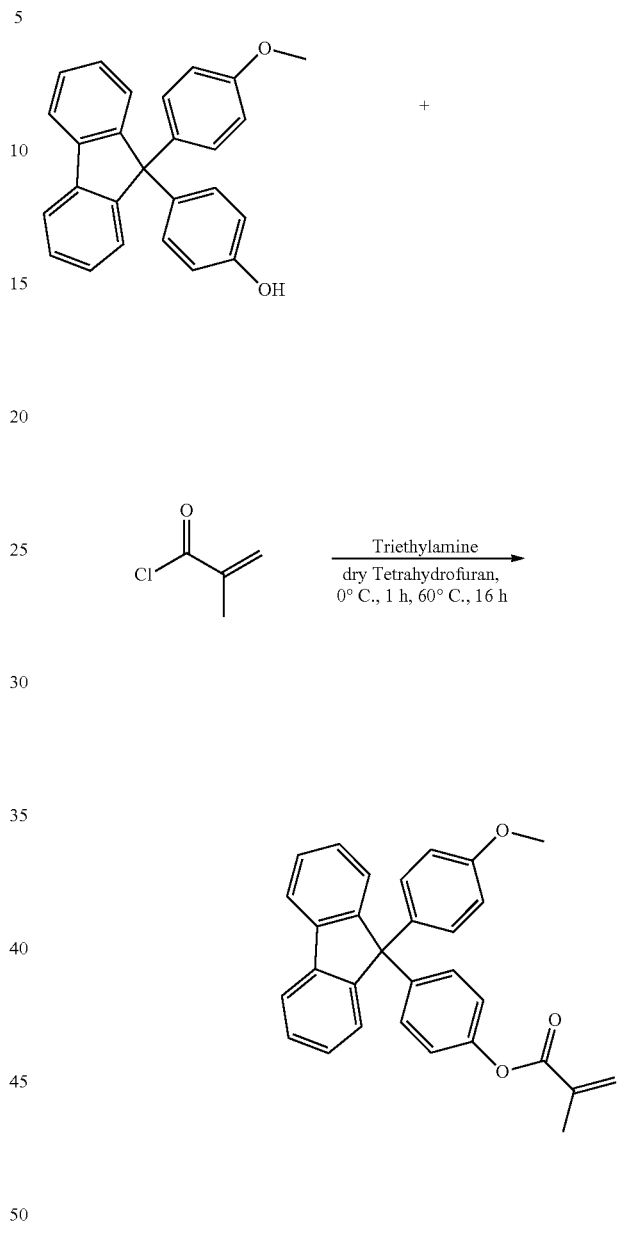

4-(9-(4-methoxyphenyl)-9H-fluoren-9-yl)phenol was dissolved in dry tetrahydrofuran then thriethylamine was added. The solution was then cooled to 0° C. and 2 equivalents of methacryloyl chloride was added drop wise and the reaction was stirred at 0° C. for 1 h. The reaction was then allowed to warm up to room temperature over several hours. The reacted was then heated to 60° C. and reacted for an additional 16 hours. The reaction was worked up by adding DI water to the crude reaction mixture followed by extraction with ethyl acetate 3 times. The organic layers were combined and washed 1× with saturated sodium bicarbonate, 1× with deionized water, and 1× with saturated sodium chloride solution. The organic layer was dried over magnesium sulfate and concentrated under vacuum.

Example 4: Synthesis of 2-((((3,6-dibromo-9-phenyl-9H-fluoren-9-yl)oxy)carbonyl)amino)ethyl Methacrylate

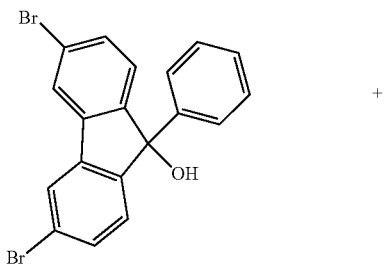

3,6-dibromo-9-phenyl-9H-fluoren-9-ol was dissolved in ethyl acetate then 1.1 equivalents of 2-isocyanatoethyl methacrylate was added to the solution. The solution was then heated to 60° C. and Tin (II) 2-ethylhexanoate was added and the reaction was stirred at 60° C. for 16 hours. The reaction was worked up by adding DI water to the crude reaction mixture followed by extraction with ethyl acetate 3 times. The organic layers were combined and washed 1× with saturated sodium bicarbonate, 1× with deionized water, and 1× with saturated sodium chloride solution. The organic layer was dried over magnesium sulfate and concentrated under vacuum.

Example 5: Synthesis of ((((((9H-fluorene-9,9-diylbis(4,1-phenylene))bis(oxy))bis(ethane-2,1-diyl))bis(oxy))bis(carbonyl))bis(azanediyl))bis(ethane-2,1-diyl) bis(2-methylacrylate)

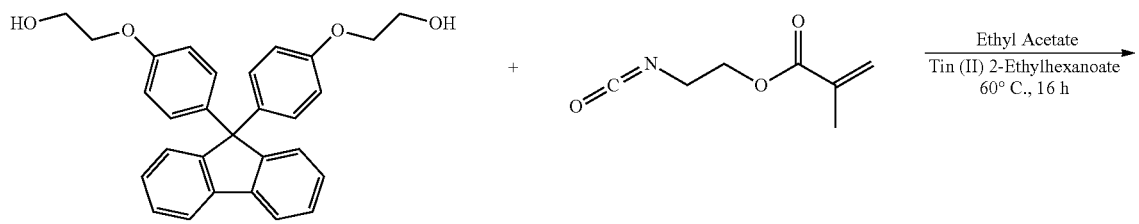

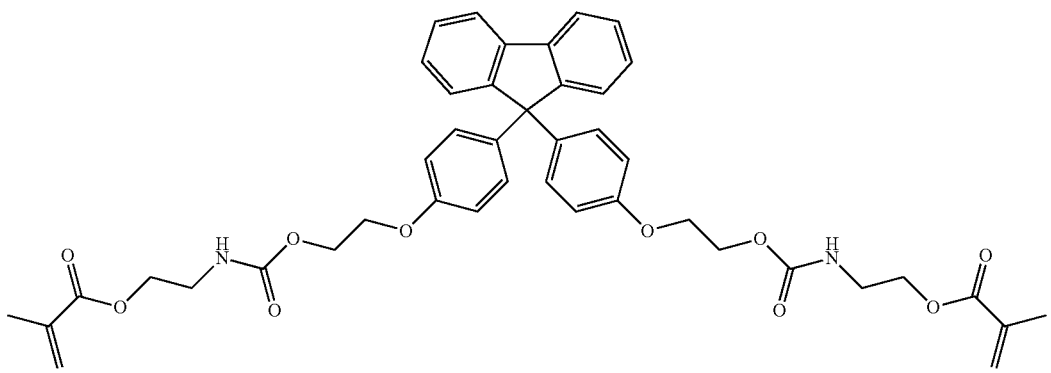

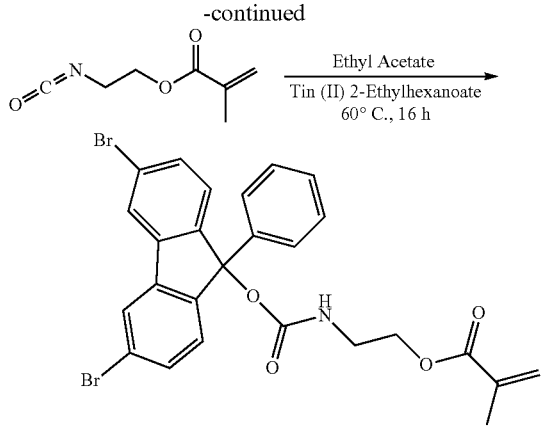

2,2'-(((9H-fluorene-9,9-diyl)bis(4,1-phenylene))bis(oxy))bis(ethan-1-ol) was dissolved in ethyl acetate then 2.05 equivalents of 2-isocyanatoethyl methacrylate was added to the solution. The solution was then heated to 60° C. and Tin (II) 2-ethylhexanoate was added and the reaction was stirred at 60° C. for 16 hours. The reaction was worked up by adding DI water to the crude reaction mixture followed by extraction with ethyl acetate 3 times. The organic layers were combined and washed 1× with saturated sodium bicarbonate, 1× with deionized water, and 1× with saturated sodium chloride solution. The organic layer was dried over magnesium sulfate and concentrated under vacuum.

Example 6: Synthesis of (((((((9H-fluorene-9,9-diylbis(4,1-phenylene))bis(oxy))bis(ethane-2,1-diyl))bis(oxy))bis(carbonyl))bis(azanediyl))bis(ethane-2,1-diyl) Diacrylate

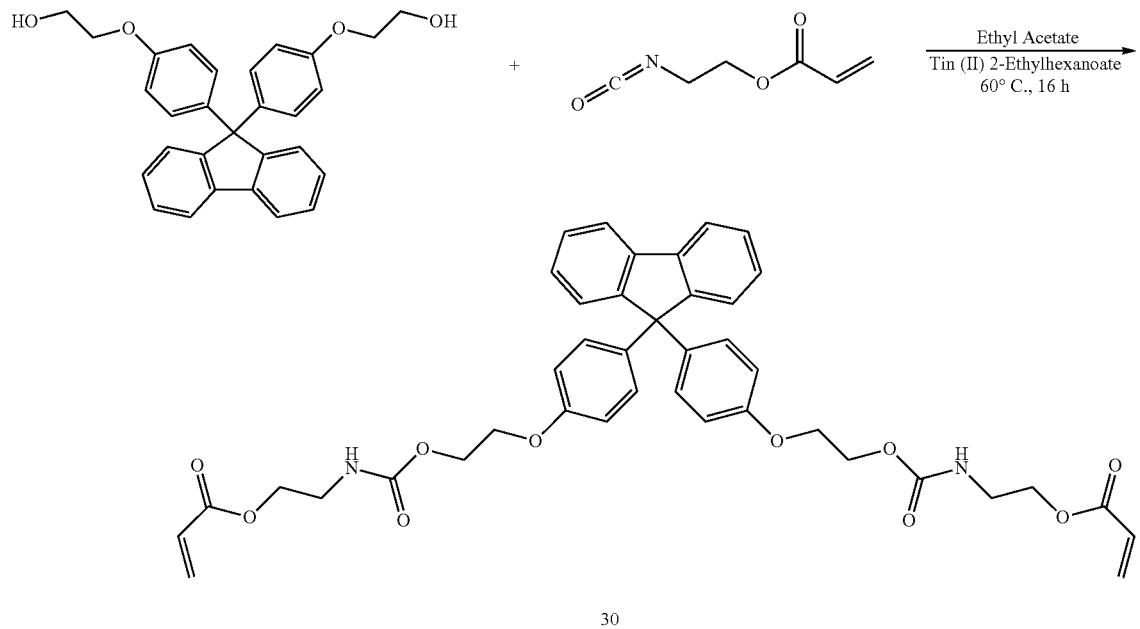

2,2'-(((9H-fluorene-9,9-diyl)bis(4,1-phenylene))bis(oxy))bis(ethan-1-ol) was dissolved in ethyl acetate then 2.05 equivalents of 2-isocyanatoethyl methacrylate was added to the solution. The solution was then heated to 60° C. and Tin (II) 2-ethylhexanoate was added and the reaction was stirred at 60° C. for 16 hours. The reaction was worked up by adding DI water to the crude reaction mixture followed by extraction with ethyl acetate 3 times. The organic layers were combined and washed 1× with saturated sodium bicarbonate, 1× with deionized water, and 1× with saturated sodium chloride solution. The organic layer was dried over magnesium sulfate and concentrated under vacuum.

Example 7: Synthesis 3,3'-(((9H-fluorene-9,9-diyl)bis(4,1-phenylene))bis(oxy))bis(1-(phenylthio)propan-2-ol)

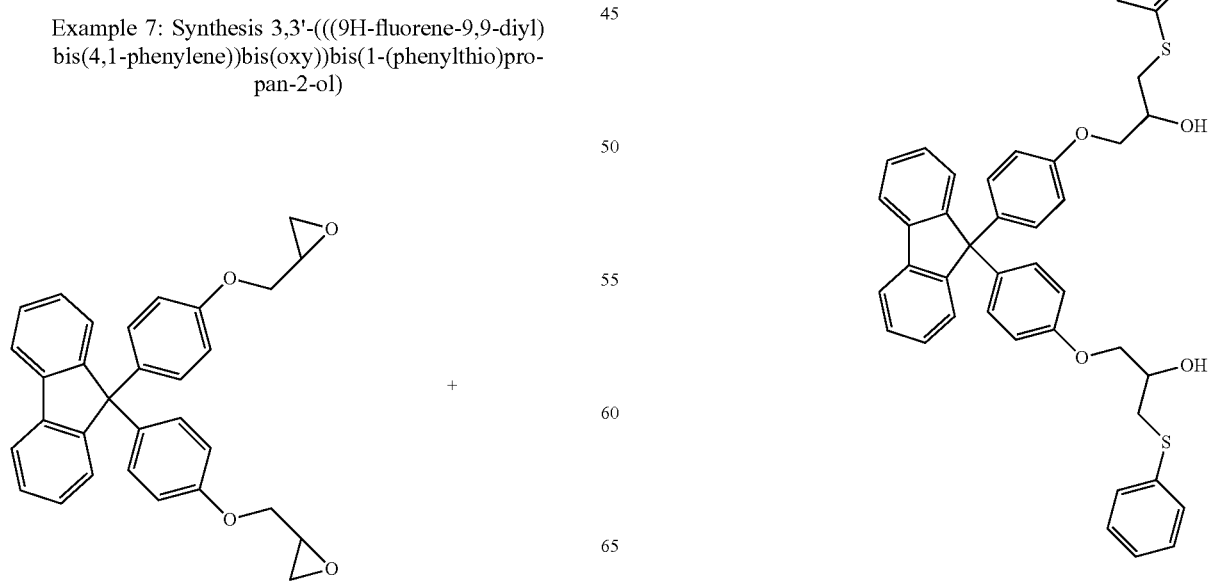

2,2'-((((9H-fluorene-9,9-diyl)bis(4,1-phenylene))bis(oxy))bis(methylene))bis(oxirane) was dissolved in tetrahydrofuran followed by addition of 2 equivalent thiophenol. 2 equivalents of triethylamine was then added slowly to control potential exotherm. The solution was the heated to 65° C. and left to react overnight. The reaction was worked up by adding water to the crude reaction mixture followed by extraction with ethyl acetate 3 times. The organic layers were combined and washed 1× with saturated sodium bicarbonate, 1× with deionized water, and 1× with saturated sodium chloride solution. The organic layer was dried over magnesium sulfate and concentrated under vacuum.

Example 8: Synthesis 3 (((((((9H-fluorene-9,9-diyl-bis(4,1-phenylene))bis(oxy))bis(3-(phenylthio)propane-1,2-diyl))bis(oxy))bis(carbonyl))bis(azanediyl))bis(ethane-2,1-diyl) bis(2-methylacrylate)

-continued

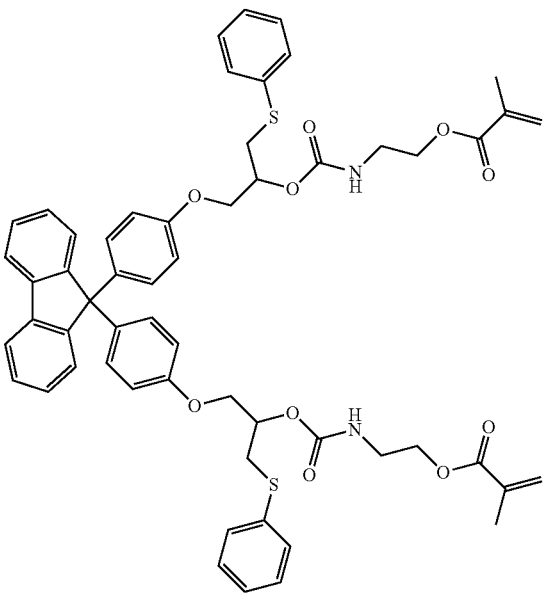

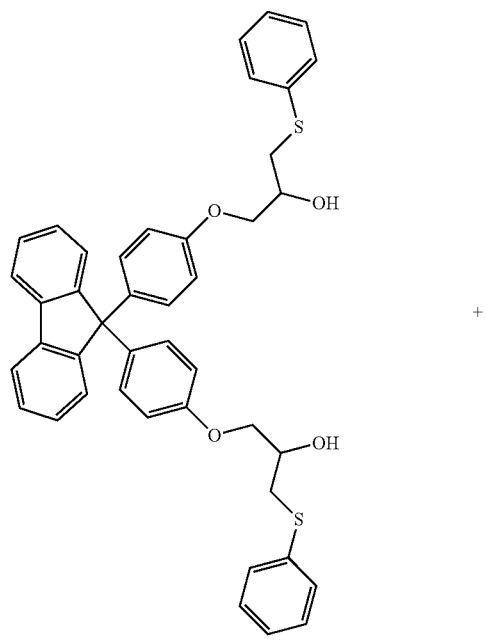

+

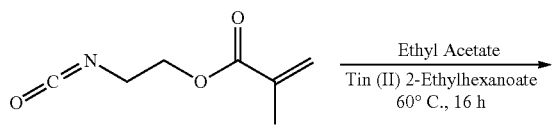

3,3'-(((9H-fluorene-9,9-diyl)bis(4,1-phenylene))bis(oxy))bis(1-(phenylthio)propan-2-ol) was dissolved in ethyl acetate then 2.05 equivalents of 2-isocyanatoethyl methacrylate was added to the solution. The solution was then heated to 60° C. and Tin (II) 2-ethylhexanoate was added and the reaction was stirred at 60° C. for 16 hours. The reaction was worked up by adding DI water to the crude reaction mixture followed by extraction with ethyl acetate 3 times. The organic layers were combined and washed 1× with saturated sodium bicarbonate, 1× with deionized water, and 1× with saturated sodium chloride solution. The organic layer was dried over magnesium sulfate and concentrated under vacuum.

The invention claimed is:

1. A recording material for writing a volume Bragg grating, the material comprising a transparent support, a polyurethane matrix, and a photopolymerizable imaging precursor compound of Formula II(b):

Formula II(b)

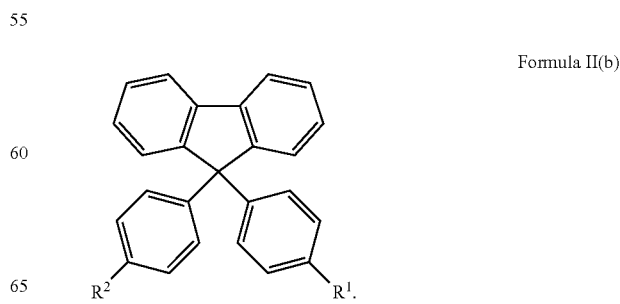

wherein in Formula II(b):
at least one of $R^1$ and $R^2$ comprises a group selected from

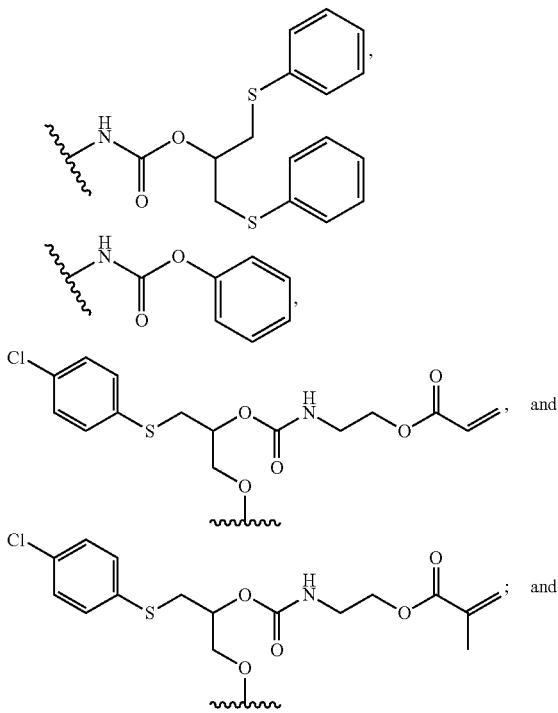

at least one of $R^1$ and $R^2$ comprises a polymerizable or crosslinkable group selected from optionally substituted alkenyl, optionally substituted cycloalkenyl, optionally substituted alkynyl, optionally substituted acrylate, optionally substituted methacrylate, optionally substituted styrene, optionally substituted epoxide, optionally substituted thiirane, optionally substituted glycidyl, optionally substituted lactone, optionally substituted lactam, and optionally substituted carbonate.

2. The recording material of claim 1, wherein the material has a thickness of between 1 μm and 500 μm.

3. The recording material of claim 1, wherein the at least one of $R^1$ and $R^2$ comprises a polymerizable or crosslinkable group selected from optionally substituted alkenyl, optionally substituted alkynyl, optionally substituted epoxide, optionally substituted glycidyl, optionally substituted acrylate, and optionally substituted methacrylate.

4. The recording material of claim 1, wherein the at least one of $R^1$ and $R^2$ comprises a polymerizable or crosslinkable group selected from optionally substituted alkenyl and optionally substituted alkynyl.

5. The recording material of claim 1, wherein the at least one of $R^1$ and $R^2$ comprises a polymerizable or crosslinkable group selected from optionally substituted epoxide and optionally substituted glycidyl.

6. The recording material of claim 1, wherein the at least one of $R^1$ and $R^2$ comprises a polymerizable or crosslinkable group selected from optionally substituted acrylate and optionally substituted methacrylate.

7. A volume Bragg grating recorded on the recording material of claim 1, wherein the grating is characterized by a Q parameter equal to or greater than 5, wherein $$Q = \frac{2\pi\lambda_0 d}{n_0 \Lambda^2}$$

and wherein $\lambda_0$ is a recording wavelength, d is the thickness of the recording material, $n_0$ is a refractive index of the recording material, and $\Lambda$ is a grating constant.

* * * * *